(12) United States Patent
Tegzes et al.

(10) Patent No.: US 12,229,953 B2
(45) Date of Patent: Feb. 18, 2025

(54) SYSTEM AND METHOD FOR VISUALIZING PLACEMENT OF A MEDICAL TUBE OR LINE

(71) Applicant: GE Precision Healthcare LLC, Wauwatosa, WI (US)

(72) Inventors: Pal Tegzes, Budapest (HU); Zita Herczeg, Szeged (HU); Tao Tan, Nuenen (NL); Balazs Peter Cziria, Budapest (HU); Alec Joseph Baenen, Hartland, WI (US); Gireesha Chintharnani Rao, Pewaukee, WI (US); Lehel Ferenczi, Budapest (HU); Gopal Biligeri Avinash, Concord, CA (US); Zoltan Kiss, Budapest (HU); Hongxu Yang, Utrecht (NL); Beth Ann Heckel, Waukesha, WI (US)

(73) Assignee: GE Precision Healthcare LLC, Wauwatosa, WI (US)

( * ) Notice: Subject to any disclaimer, the term of this patent is extended or adjusted under 35 U.S.C. 154(b) by 124 days.

(21) Appl. No.: 17/951,281

(22) Filed: Sep. 23, 2022

(65) Prior Publication Data
US 2023/0162352 A1 May 25, 2023

Related U.S. Application Data

(60) Provisional application No. 63/282,814, filed on Nov. 24, 2021.

(51) Int. Cl.
*G06T 7/00* (2017.01)
*G16H 50/20* (2018.01)

(52) U.S. Cl.
CPC .......... *G06T 7/0012* (2013.01); *G16H 50/20* (2018.01); *G06T 2207/20081* (2013.01)

(58) Field of Classification Search
CPC ....... G06T 7/0012; G06T 11/00; G06T 11/60; G06T 2207/20081; G16H 50/20; G16H 30/20; G06N 3/08
(Continued)

(56) References Cited

U.S. PATENT DOCUMENTS 7,630,531 B2 12/2009 Chui
8,862,209 B2 * 10/2014 Whitman ............... A61B 17/02
600/478

(Continued)

OTHER PUBLICATIONS

EP application 22207340.5 filed Nov. 14, 2022—extended Search Report issued on Apr. 21, 2023, 13 pages.
(Continued)

*Primary Examiner* — Prabodh M Dharia
(74) *Attorney, Agent, or Firm* — Fletcher Yoder, P.C.

(57) ABSTRACT

An image processing system is provided. The image processing system includes a display, a processor, and a memory. The memory stores processor-executable code that when executed by the processor causes receiving an image of a region of interest of a patient with an enteric tube or line disposed within the region of interest, detecting the medical tube or line within the image, generating a combined image by superimposing graphical markers on the image that indicate placement or misplacement of the enteric tube or line, and displaying the combined image on a display. In further aspects, a classification of the enteric tube or line (e.g., correctly placed tube present, malpositioned tube present, and so forth) may be determined and communicated to one or more clinicians. Additionally, the outputs of the image processing system may also be provided to facilitate triage of patients, helping prioritize which tube placements require further attention and in what order.

20 Claims, 34 Drawing Sheets

(58) Field of Classification Search
USPC .......................................... 345/418; 604/264
See application file for complete search history.

(56) References Cited

U.S. PATENT DOCUMENTS

| | | | |
|---|---|---|---|
| 9,471,973 B2 | 10/2016 | Enzmann et al. | |
| 9,717,461 B2 | 8/2017 | Yu et al. | |
| 11,020,016 B2* | 6/2021 | Wallace | A61B 90/37 |
| 11,410,341 B2 | 8/2022 | Baenen et al. | |
| 11,529,070 B2* | 12/2022 | Silverstein | A61B 5/283 |
| 11,730,342 B2* | 8/2023 | Ries | A61B 1/012 |
| | | | 600/104 |
| 2012/0184924 A1* | 7/2012 | Ejike | A61M 39/08 |
| | | | 604/264 |
| 2016/0361121 A1* | 12/2016 | Reicher | G06F 3/0482 |
| 2017/0215762 A1* | 8/2017 | Burnside | A61B 5/6848 |
| 2019/0021677 A1* | 1/2019 | Grbic | G06T 7/11 |
| 2019/0313986 A1* | 10/2019 | Do | A61B 6/12 |
| 2021/0059607 A1 | 3/2021 | Gormley et al. | |

OTHER PUBLICATIONS

Harris Robert J et al: "Measurement of Endotracheal Tube Positioning on Chest X-Ray Using Object Detection" Journal of Digital Imaging, vol. 34, No. 4, Jul. 28, 2021, pp. 846-852, XP037568368, ISSN: 0897-1889, DOI: 10.1007/S10278-021-00495-6 [retrieved on Jul. 28, 2021].

Sirazitdinov Ilyas et al: "Landmark Constellation Models for Central Venous Catheter Malposition Detection", 2021 IEEE 18th International Symposium on Biomedical Imaging (ISBI), IEEE, Apr. 13, 2021, pp. 1132-1136, XP033917816, DOI: 10.1109/ISBI48211.2021.9434022 [retrieved on May 17, 2021].

"QXR: AI for Detection of Abnormal Findings on a Chest X-Ray," Qure AI | AI to Enable Accessible, Affordable & Timely Care across the Globe, Dec. 27, 2022, https://qure.ai/product/qxr/.

"Annalise Enterprise CXR Comprehensive Medical Imaging AI," USA.annalise.ai, Nov. 17, 2022, https://usa.annalise.ai/solutions/annalise-cxr/.

"FDA Clears Software to Rapidly, Accurately Confirm Placement of Lifesaving Medical Devices on X-Ray," Imaging Technology News, Oct. 3, 2021, https://www.itnonline.com/content/fda-clears-software-rapidly-accurately-confirm-placement-lifesaving-medical-devices-x-ray.

Raiqc, https://www.raiqc.com/, Feb. 2024.

"Placement of Enteric Tube," American College of Radiology, https://www.acrdsi.org/DSI-Services/Define-AI/Use-Cases/Placement-of-Enteric-Tube, Jul. 2024.

D.H. Mallon et al., "Automated detection of enteric tubes misplaced in the respiratory tract on chest radiographs using deep learning with two centre validation," Clinical Radiology, 2022, pp. e758-e764, vol. 77, Issue 10.

Gongbo Liang et al., "Development of CNN Models for the Enteral Feeding Tube Positioning Assessment on a Small Scale Data Set," BMC Medical Imaging, 2022, vol. 22, No. 1, https://doi.org/10.1186/s12880-022-00766-w.

Varun Singh et al., "Assessment of Critical Feeding Tube Malpositions on Radiographs Using Deep Learning," Journal of Digital Imaging, 2019, pp. 651-655, vol. 32, No. 4, https://doi.org/10.1007/s10278-019-00229-9.

Xin Yi et al., "Automatic catheter detection in pediatric X-ray images using a scale-recurrent network and synthetic data," 1st Conference on Medical Imaging with Deep Learning, 2018, pp. 1-10, Amsterdam, The Netherlands.

Matthew Harwood et al. "Prediction Model for Correct Enteric Feeding Tube Placement," SiiM19 Annual Meeting, Jun. 26-28, Denver, CO.

Andres Chacon Martinez et al., "Pitfalls and Failures in Creating an Ng/Et Tube Detection Tool via CXR and Machine Learning," Chest, 2020, vol. 158, No. 4, https://doi.org/10.1016/j.chest.2020.08.1253.

Xin Yi et al., "Computer-Aided Assessment of Catheters and Tubes on Radiographs: How Good Is Artificial Intelligence for Assessment?," Radiology: Artificial Intelligence, 2020, vol. 2, No. 1, https://doi.org/10.1148/ryai.2020190082.

Hyunkwang Lee et al., "Machine Intelligence for Accurate X-ray Screening and Read-out Prioritization: PICC line Detection Study," SIIM 2017 Scientific Session, Jun. 1.

Matthew Brown et al., "Device Placement Confirmation System Aims to Bring AI into Clinical Setting," p. 3.

"Ranzcr Clip—Catheter and Line Position Challenge," Kaggle, https://www.kaggle.com/c/ranzcr-clip-catheter-line-classification.

U.S. Appl. No. 17/993,612, filed Nov. 23, 2022, Pal Tegzes.

* cited by examiner

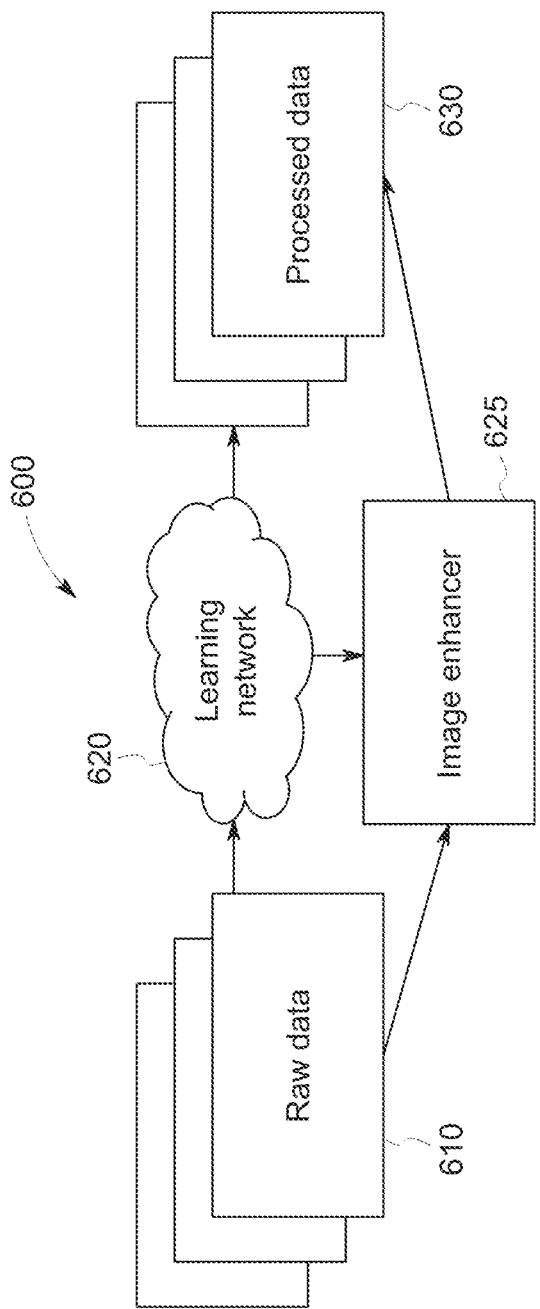
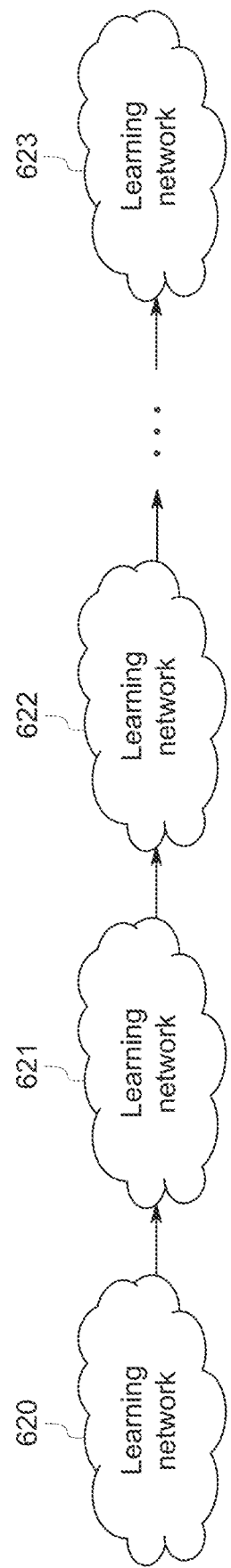
FIG. 6A
FIG. 6B

SYSTEM AND METHOD FOR VISUALIZING PLACEMENT OF A MEDICAL TUBE OR LINE

CROSS-REFERENCE TO RELATED APPLICATION

This application claims priority to and the benefit of U.S. Provisional Application No. 63/282,814, entitled "SYSTEM AND METHOD FOR VISUALIZING PLACEMENT OF A MEDICAL TUBE OR LINE", filed Nov. 24, 2021, which is herein incorporated by reference in its entirety for all purposes.

TECHNICAL FIELD

The subject matter disclosed herein relates to medical image processing, and more particularly to systems and methods for visualizing placement of a medical tube or line, such as an enteric tube (e.g., a nasogastric tube).

BACKGROUND

Medical imaging may be utilized to visualize medically placed tubes or lines (e.g., chest tube, a nasogastric tube, an enteric tube, endotracheal tube, vascular line, a peripherally inserted central catheter (PICC), a catheter, etc.). However, it may be difficult for medical personnel (e.g., doctor, radiologist, technician, etc.) to visualize these medically placed tubes or lines. In addition, the medical personnel may be untrained or inexperienced, which may hinder their ability to identify the medically placed tube or line and to determine if it is properly placed. Further, medical personnel may have to manually make measurements (which may be time consuming) to determine if a medically placed tube or line is properly placed. If a medically placed tube or line is misplaced, prompt information of such misplacement may be desirable in order to take corrective action.

BRIEF DESCRIPTION

A summary of certain embodiments disclosed herein is set forth below. It should be understood that these aspects are presented merely to provide the reader with a brief summary of these certain embodiments and that these aspects are not intended to limit the scope of this disclosure. Indeed, this disclosure may encompass a variety of aspects that may not be set forth below.

In certain embodiments, in determining whether a medically placed tube or line (e.g., an enteric tube or line) is placed properly (e.g., via the deep learning networks models), a technique is provided includes comparing a measured distance between the surface and/or end of the tube or line and a reference or anatomical landmark to a desired threshold and determining if the distance (which may be measured, for example, as the geometrical distance of two points (e.g., along a straight line) or as a distance measured along the tube curve) is acceptable. The desired threshold may represent an acceptable range for the distance between the tube or line and the reference or anatomical landmark for the tube or line to be correctly placed. For example, for a nasogastric tube, the desired threshold may be a range of distance below the gastroesophageal junction. If the measured distance is not acceptable, the techniques may include providing a user-perceptible indication of misplacement on a display. The indication may be provided on the display where the combined image is displayed or provided on another device (e.g., the user's device). The indication may be text stating that the tube or line is misplaced. In certain embodiments, the text may be more specific and state the tube or line is too high or too low or otherwise improper. In certain embodiments, the text may provide further instructions (e.g., to raise or lower the end of the tube or line a certain distance). In some embodiments, the text may be color coded (e.g., in orange or red) to further indicate the misplacement. In some embodiments, the indication may be provided via color coding of one or more graphical markers or the tube or line displayed on the combined image. For the example, one or more of the graphical markers (e.g., for the end of tube or line, for the reference or anatomical landmark, and/or the indication of the measured distance there between) and/or the tube or line may be color coded a specific color (e.g., red or orange) to indicate the misplacement. Alternatively or in addition, one or more of the graphical markers may flash or otherwise be visually highlighted if the tube or line is misplaced. If the measured distance is acceptable, the techniques may include providing a user-perceptible indication of proper placement of the tube or line. The indication may be provided on the display where the combined image is displayed or provided on another device (e.g., the user's device). The indication for proper placement may be text stating the tube or line is properly placed. In certain embodiments, the indication for proper placement may be provided via color coding one or more graphical markers of the tube or line displayed on the combined image (e.g., all the graphical markers and/or the tube or line may be color coded green). In certain embodiments, the indication of proper placement or misplacement may be written into a standard or private information tag (e.g., DICOM) and made visible in subsequent information systems that the image is sent too (e.g., PACS). In certain embodiments, the determination as to whether the medically placed tube or line is properly placed or positioned may be manually done by the medical personnel viewing the displayed combined image.

In the context of a nasogastric tube which may be described herein as an example, with respect to proper placement, a nasogastric tube may be inserted so as to bisect the airways and diaphragm on the X-ray projection (e.g., to be positioned substantially on the midline with respect to the airway). The inserted tip (i.e., distal tip) and side ports (if present) are below the diaphragm when properly placed, typically positioned toward the patient's left hand side. Proper insertion and placement of the tube avoids or mitigates possible risks, such as the risk of insertion into the lungs (with the associated risk of substances entering the lungs), the risk of the tube placement being too high, e.g., in the esophagus, and the risk that loops or kinks in the inserted tube may disturb the flow and/or irritate the patient.

As discussed herein, and in the context of the preceding discussion, the presently described techniques utilize an AI-based feature to facilitate and assess the placement of enteric tubes, including but not limited to nasogastric tubes. The AI-based feature may be used to detect and/or characterize the placed tube, to provide a graphical summary showing the tube with respect to relevant anatomical features (e.g., in the actual anatomical context), and to classify the tube as being placed correctly or needing adjustment. Use of the AI-based feature may, therefore, increase the confidence of the bedside team when placing tubes. Use of the Ai-based feature may also facilitate prioritization of potentially misplaced tubes for review, such as by a radiologist, and may speed up the review process, thereby helping to avoid complications associated with misplaced tubes.

Features and benefits provided by the techniques described herein include, but are not limited to: the ability to localize particular features (e.g., the tube tip, side port, end port, and so forth) of the enteric tube; the ability to localize relevant anatomical features and context (e.g., diaphragm, airways, carina, lungs, patient midline, and so forth); the ability to localize other relevant devices that may be potentially confounding with enteric tubes (e.g., probes, peripherally inserted central catheter (PICC) lines, electrocardiogram (ECG) leads or lines, endotracheal (ET) tube, and so forth); the ability to assess the tube position and to provide explanation or commentary about the assessment (e.g., explaining specific problems with current tube placement, such as "the side port location is too high relative to the diaphragm"); the ability to assess the tube position and to provide explanation or commentary regarding aspects of the placement verified to be correct or satisfactory (e.g., that the tube correctly bisects the diaphragm near the midline); the ability to provide automated measurements that are relevant for the tube assessment (e.g. the length of the tube below the diaphragm, the distance of the side port from the diaphragm, the measured tube diameter, etc.); the ability to show the detected tubes, the tube features, and relevant anatomical features and measurements in a graphical summary and the ability to highlight potentially problematic (or non-problematic) areas within the graphical summary); the ability to perform triage based on the tube placement classification, allowing prioritization of attention to potentially misplaced tubes; the ability to save the graphical summary in various formats (secondary capture, structure report, Integrating the Healthcare Enterprise (IHE) AI Results (AIR), and so forth); and the ability to allow the user to edit, modify, and/or annotate the graphical summary.

In accordance with an embodiment, a medical image processing system is provided. In accordance with this embodiment, the medical image processing system may comprising: a display; a processor; and a memory storing processor-executable code. The processor-executable code, when executed by the processor, causes acts to be performed comprising: receiving one or both of a chest or abdominal image of a patient with an enteric tube or line disposed within the region of interest; detecting the enteric tube or line within the image or images; generating a combined image by superimposing one or more graphical markers on the image or images wherein the one or more graphical markers indicate one or more features of enteric tube in an anatomic context; and displaying the combined image on the display.

BRIEF DESCRIPTION OF THE DRAWINGS

These and other features, aspects, and advantages of the present subject matter will become better understood when the following detailed description is read with reference to the accompanying drawings in which like characters represent like parts throughout the drawings, wherein:

FIG. 6A is a schematic diagram of an embodiment of a configuration to apply a learning network to process and/or otherwise evaluate an image;

FIG. 6B is a schematic diagram of an embodiment of a combination of a plurality of learning networks;

DETAILED DESCRIPTION

Figure 1:
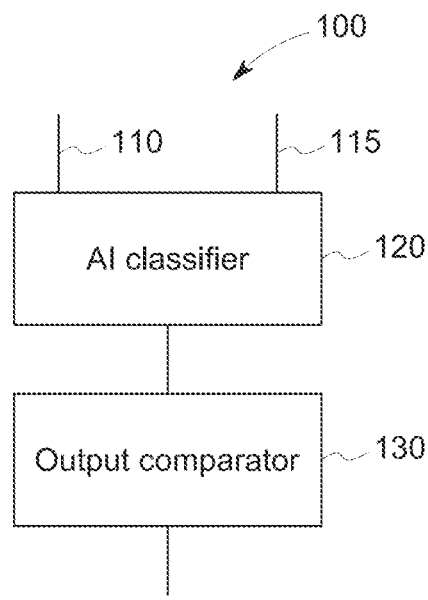
FIG. 1 is a schematic diagram of an embodiment of a condition comparator.

One or more specific embodiments will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present subject matter, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

Imaging devices (e.g., gamma cameras, positron emission tomography (PET) scanners, computed tomography (CT) scanners, X-Ray machines, fluoroscopy machines, magnetic resonance (MR) imaging machines, ultrasound scanners, etc.) generate medical images (e.g., native Digital Imaging and Communications in Medicine (DICOM) images) representative of the parts of the body (e.g., organs, tissues, etc.) for various clinical purposes, such as to diagnose and/or treat diseases. Medical images may include volumetric data including voxels associated with the part of the body captured in the medical image. Medical image visualization software allows a clinician to segment, annotate, measure, and/or report functional or anatomical characteristics on various locations of a medical image. In some examples, a clinician may utilize the medical image visualization software to identify regions of interest within the medical image.

Acquisition, processing, quality control, analysis, and storage of medical image data play an important role in diagnosis and treatment of patients in a healthcare environment. A medical imaging workflow and devices involved in the workflow can be configured, monitored, and updated throughout operation of the medical imaging workflow and devices. Machine and/or deep learning can be used to help configure, monitor, and update the medical imaging workflow and devices.

Certain examples discussed herein provide and/or facilitate the use of imaging devices to provide improved clinical services and outcomes. Certain examples facilitate improved or modified image reconstruction and/or presentation and further processing to provide improved data and analytics for certain clinical procedures, namely insertion and placement of a medical line or tube, such as an enteric tube (e.g., a nasogastric tube).

Certain examples provide an image processing apparatus including an artificial intelligence classifier. The classifier can detect, segment, and quantify anatomic features and/or medical devices, for example. The classifier can be a discrete output of positive or negative for a finding, a segmentation, etc. For example, the classifier can instantiate machine learning and/or other artificial intelligence to detect, segment, and analyze a presence of a medical device (e.g., medically placed tube or line). By way of example, the classifier can instantiate machine learning and/or other artificial intelligence to detect an end of a medically placed tube or line (such as an enteric tube), detect a reference or anatomical landmark, determine a position of the medically placed tube or line relative to the reference or anatomical landmark, measure a distance between the end of the medically placed tube or line and the reference landmark, and determine whether the tube or line is properly placed.

Machine learning techniques, whether deep learning networks or other experiential/observational learning system, can be used to locate an object in an image, understand speech and convert speech into text, and improve the relevance of search engine results, for example. Deep learning is a subset of machine learning that uses a set of algorithms to model high-level abstractions in data using a deep graph with multiple processing layers including linear and non-linear transformations. While many machine learning systems are seeded with initial features and/or network weights to be modified through learning and updating of the machine learning network, a deep learning network trains itself to identify "good" features for analysis. Using a multilayered architecture, machines employing deep learning techniques can process raw data better than machines using conventional machine learning techniques. Examining data for groups of highly correlated values or distinctive themes is facilitated using different layers of evaluation or abstraction.

Throughout the specification and claims, the following terms take the meanings explicitly set forth herein, unless the context dictates otherwise. The term "deep learning" is a machine learning technique that utilizes multiple data processing layers to recognize various structures in data sets and classify the data sets with high accuracy. A deep learning network can be a training network (e.g., a training network model or device) that learns patterns based on a plurality of inputs and outputs. A deep learning network can be a deployed network (e.g., a deployed network model or device) that is generated from the training network and provides an output in response to an input.

The term "supervised learning" is a deep learning training method in which the machine is provided already classified data from human sources. The term "unsupervised learning" is a deep learning training method in which the machine is given data that has not been previously classified for training. Such unsupervised learning techniques may be suitable for training that is directed to abnormality detection. The term "semi-supervised learning" is a deep learning training method in which the machine is provided a small amount of classified data from human sources compared to a larger amount of unclassified data available to the machine.

The term "representation learning" is a field of methods for transforming raw data into a representation or feature that can be exploited in machine learning tasks. In supervised learning, features are learned via labeled input.

The term "convolutional neural networks" or "CNNs" are biologically inspired networks of interconnected data used in deep learning for detection, segmentation, and recognition of pertinent objects and regions in datasets. CNNs evaluate raw data in the form of multiple arrays, breaking the data into a series of stages and examining the data for learned features.

The term "transfer learning" is a process of a machine storing the information used in properly or improperly solving one problem to solve another problem of the same or similar nature as the first. Transfer learning may also be known as "inductive learning". Transfer learning can make use of data from previous tasks, for example.

The term "active learning" is a process of machine learning in which the machine selects a set of examples for which to receive training data, rather than passively receiving examples chosen by an external entity. For example, as a machine learns, the machine can be allowed to select examples that the machine determines will be most helpful for learning, rather than relying only an external human expert or external system to identify and provide examples.

The term "computer aided detection" or "computer aided diagnosis" refer to computers that analyze medical images for the purpose of detecting an anatomic structure of interest, a physiological measurement or event of interest, and/or of suggesting a possible diagnosis.

Certain examples use neural networks and/or other machine learning architectures to implement a new workflow for image and associated patient analysis including generating alerts based on radiological findings that may be generated and delivered at the point of care of a radiology exam. Certain examples use Artificial Intelligence (AI) algorithms to process one or more imaging exams (e.g., an image or set of images), and provide an alert based on the automated exam analysis. The alert(s) (e.g., including notification(s), recommendation(s), other action(s), etc.) may be intended for the technologist performing the exam, clinical team providers (e.g., nurse, doctor, etc.), radiologist, administration, operations, and/or even the patient. The alerts may be provided to indicate a specific, or multiple, quality control issue and/or radiological finding(s) or lack thereof in the exam image data, for example.

In certain examples, the AI algorithm can be (1) embedded within an imaging device, (2) running on a mobile device (e.g., a tablet, smart phone, laptop, other handheld or mobile computing device, etc.), and/or (3) running in a cloud computing architecture (e.g., on premise or off premise) and delivers the alert via a web browser (e.g., which may appear on the radiology system, mobile device, computer, etc.). Such configurations can be vendor neutral and compatible with legacy imaging systems. For example, if the AI processor is running on a mobile device and/or in the "cloud", the configuration can receive the images (A) from the x-ray and/or other imaging system directly (e.g., set up as secondary push destination such as a Digital Imaging and Communications in Medicine (DICOM) node, etc.), (B) by tapping into a Picture Archiving and Communication System (PACS) destination for redundant image access, (C) by retrieving image data via a sniffer methodology (e.g., to pull a DICOM image off the system once it is generated), etc.

Certain examples provide apparatus, systems, methods, etc., to determine and provide, as discussed herein, clinical feedback relevant to the treatment or care of a patient, such as placement of a clinical line or tube, and/or other patient-relevant conditions based on output of an algorithm instantiated using and/or driven by an artificial intelligence (AI) model, such as a deep learning network model, machine learning network model, etc. For example, the presence of a medically placed tube or line (e.g. chest tube, an enteric tube (such as a nasogastric tube), endotracheal tube, vascular line, a peripherally inserted central catheter, a catheter, etc.) can be determined based on an output of an AI detection algorithm. In addition, the placement of a medical tube or line within a region of interest (e.g., lung, stomach, vascular system, etc.) can be determined based on an output of an AI detection (e.g., whether the medical tube or line is properly placed).

Certain examples discussed and described herein provide systems and method to detect a medically placed tube or line within a region of interest of a patient and whether the tube or line is properly placed within the region of interest based on an AI classification algorithm applied to a patient's data. An example method includes detecting a presence of a medically placed tube or line in an image; detecting an one or more a terminal end and/or surface contours of the medically placed tube or line in the image; detecting a reference one or more anatomical landmarks in the image; determining whether the medically placed tube or line is properly placed relative to the reference or anatomical landmark(s); and/or providing a notification for a caregiver as to whether the medically placed tube or line is properly placed relative to the reference or anatomical landmark(s). In certain embodiments, the AI classification algorithm may detect the presence of the medically placed line or tube; graphically mark the medically placed line or tube with a visual (e.g., color or color-coded) graphical overlay; detect a surface and/or end (e.g., distal end) of the medically placed line or tube; graphically mark the surface and/or end of the medically placed tube or line; detect one or more reference or anatomical landmarks (e.g., for determining the proper placement of the tube or line relative to the landmark(s)); graphically mark the reference or anatomical landmark(s); calculate a distance between the surface and/or end of the medically placed tube or line; and/or calculate and provide a confidence metric or other metric (e.g., for the calculated distance, for the determination of the presence of the medically placed tube or line, for an accuracy in detecting the end of the tube or line, for an accuracy in detecting the reference or anatomical landmark, etc.). The AI classification algorithm is trained based on images with or without medically placed tubes or lines, images with properly placed tubes or lines, images with misplaced tubes or lines, images with the reference or anatomical landmark, and/or images without the reference or anatomical landmark.

For example, patients in a critical care setting receive x-rays (e.g., chest sx-rays) to monitor the placement of a medically placed tube or line. If a tube or line is misplaced, the medical team may need to conduct an intervention to properly place the medical tube or line. An artificial intelligence classifier can detect a presence of the medically placed tube or line, detect the surface and/or terminal end of the medically placed tube or line, detect a reference or anatomical landmark, and evaluate whether the tube or line is properly placed. An alert can be generated and output at a point of care, such as on a device (e.g., an imaging device, an imaging workstation, etc.), to notify and/or otherwise provide instructions (e.g., notification that a tube is or is not properly placed or instruction to remove the tube or line, shift the tube or line in a certain direction, etc.) to a clinical care team, for example.

The techniques describe herein provide a quick means to determine if a medically placed tube or line is improperly placed. This enables a faster intervention to ensure the tube or line is in an appropriate location for patient care. In addition, it relieves some of the burden on the medical team providing assistance to the patient (especially those personnel who may be untrained or inexperienced).

Deep learning is a class of machine learning techniques employing representation learning methods that allows a machine to be given raw data and determine the representations needed for data classification. Deep learning ascertains structure in data sets using backpropagation algorithms which are used to alter internal parameters (e.g., node weights) of the deep learning machine. Deep learning machines can utilize a variety of multilayer architectures and algorithms. While machine learning, for example, involves an identification of features to be used in training the network, deep learning processes raw data to identify features of interest without the external identification.

Deep learning in a neural network environment includes numerous interconnected nodes referred to as neurons. Input neurons, activated from an outside source, activate other neurons based on connections to those other neurons which are governed by the machine parameters. A neural network behaves in a certain manner based on its own parameters. Learning refines the machine parameters, and, by extension, the connections between neurons in the network, such that the neural network behaves in a desired manner.

Deep learning that utilizes a convolutional neural network segments data using convolutional filters to locate and identify learned, observable features in the data. Each filter or layer of the CNN architecture transforms the input data to increase the selectivity and invariance of the data. This abstraction of the data allows the machine to focus on the features in the data it is attempting to classify and ignore irrelevant background information.

Deep learning operates on the understanding that many datasets include high level features which themselves include low level features. While examining an image, for example, rather than looking for an object, it is more efficient to look for edges which form motifs which form parts, which form the object being sought. These hierarchies of features can be found in many different forms of data such as speech and text, etc.

Learned observable features include objects and quantifiable regularities learned by the machine during supervised learning. A machine provided with a large set of well classified data is better equipped to distinguish and extract the features pertinent to successful classification of new data.

A deep learning machine that utilizes transfer learning may properly connect data features to certain classifications affirmed by a human expert. Conversely, the same machine can, when informed of an incorrect classification by a human expert, update the parameters for classification. Settings and/or other configuration information, for example, can be guided by learned use of settings and/or other configuration information, and, as a system is used more (e.g., repeatedly and/or by multiple users), a number of variations and/or other possibilities for settings and/or other configuration information can be reduced for a given situation.

An example deep learning neural network can be trained on a set of expert classified data, classified and further annotated for object localization, for example. This set of data builds the first parameters for the neural network, and this would be the stage of supervised learning. During the stage of supervised learning, the neural network can be tested whether the desired behavior has been achieved.

Once a desired neural network behavior has been achieved (e.g., a machine has been trained to operate according to a specified threshold, etc.), the machine can be deployed for use (e.g., testing the machine with "real" data, etc.). During operation, neural network classifications can be confirmed or denied (e.g., by an expert user, expert system, reference database, etc.) to continue to improve neural network behavior. The example neural network is then in a state of transfer learning, as parameters for classification that determine neural network behavior are updated based on ongoing interactions. In certain examples, the neural network can provide direct feedback to another process. In certain examples, the neural network outputs data that is buffered (e.g., via the cloud, etc.) and validated before it is provided to another process.

Deep learning machines using convolutional neural networks (CNNs) can be used for image analysis. Stages of CNN analysis can be used for facial recognition in natural images, computer-aided diagnosis (CAD), etc.

High quality medical image data can be acquired using one or more imaging modalities, such as x-ray, computed tomography (CT), molecular imaging and computed tomography (MICT), magnetic resonance imaging (MRI), etc. Medical images are largely interpreted by physicians, but these interpretations can be subjective, affected by the condition of the physician's experience in the field and/or fatigue. Image analysis via machine learning can support a healthcare practitioner's workflow.

Deep learning machines can provide computer aided detection support to improve their image analysis with respect to image quality and classification, for example. However, issues facing deep learning machines applied to the medical field often lead to numerous false classifications. Deep learning machines must overcome small training datasets and require repetitive adjustments, for example.

Deep learning machines, with minimal training, can be used to determine the quality of a medical image, for example. Semi-supervised and unsupervised deep learning machines can be used to quantitatively measure qualitative aspects of images. For example, deep learning machines can be utilized after an image has been acquired to determine if the quality of the image is sufficient for diagnosis. Supervised deep learning machines can also be used for computer aided diagnosis. Supervised learning can help reduce susceptibility to false classification, for example.

Deep learning machines can utilize transfer learning when interacting with physicians to counteract the small dataset available in the supervised training. These deep learning machines can improve their computer aided diagnosis over time through training and transfer learning.

FIG. 1 illustrates an example condition comparator apparatus 100 including a plurality of inputs 110, 115, an artificial intelligence (AI) classifier 120, and an output comparator 130. Each input 110, 115 is provided to the AI classifier 120, which classifies image data and/or other information in the respective input 110, 115 to identify a condition in the input 110, 115 and to generate an indication of the identified condition based on the input 110, 115. In certain embodiments, the AI classifier 120 may classify images and/or other information in the respective input 110, 115 to identify a medically placed tube or line (e.g., chest tube, enteric tube, endotracheal tube, vascular line, a peripherally inserted central catheter, a catheter, etc.) and to identify a reference or anatomical landmark relevant to the type or line and its desired placement. Using the example comparator apparatus 100, it can be determined whether the tube or line is properly placed within a region of interest of the patient relative to a reference or anatomical landmark. In particular, both surfaces and/or an end of the tube or line as well as a reference or anatomical landmark may be located and a determination made as to whether the tube or line is properly placed relative to the reference or anatomical landmark. A distance may be measured between the end of the tube or line and the reference or anatomical landmark in determining whether the end of the tube or line is properly placed. A confidence metric (e.g., for the calculated distance, for the determination of the presence of the medically placed tube or line, for an accuracy in detecting the end of the tube or line, for an accuracy in detecting the reference or anatomical landmark, etc.) may be calculated and/or provided via user-perceptible notification or stored for further reference. Further, a notification or alert may be provided as to whether or not the medically placed tube or line is properly placed. If the tube or line is not properly placed, further instructions may be provided via a notification or alert (e.g., related to moving the tube or line in a certain direction).

Figure 2:
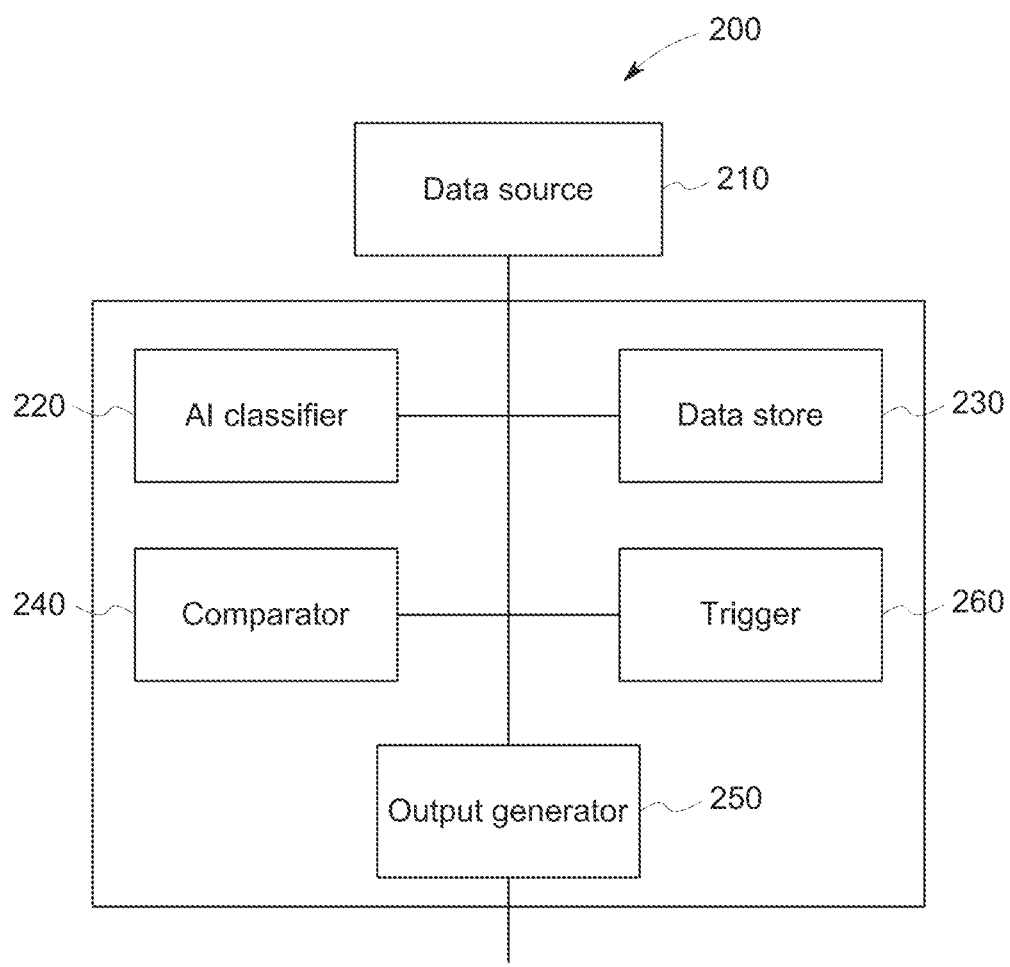
FIG. 2 is a schematic diagram of an embodiment of a clinical analysis apparatus.

FIG. 2 illustrates an example clinical progression analysis apparatus 200 that can be constructed based on the example condition comparator 100 of FIG. 1. The example apparatus 200 includes a data source 210, an artificial intelligence (AI) classifier 220, a data store 230, a comparator 240, an output generator 250, and a trigger 260. Input 110, 115 can be provided by the data source 210 (e.g., a storage device, an imaging device, etc., incorporated in and/or otherwise connected to the apparatus 200, etc.) to the AI classifier 220.

The example classifier 220 processes input over time to correlate input from the data source 210 with a classification. Thus, the AI classifier 220 processes input image data and/or other data to identify a condition in the input data and classify that condition according to one or more states (e.g., tube or line present, tube or line not present, reference or anatomical landmark present, reference or anatomical landmark not present, tube or line placed correctly, tube or line misplaced) as specified by an equation, a threshold, and/or other criterion. In certain embodiments, the AI classifier 220 processes input image data and/or other data to detect a medically placed tube or line and to determine whether an end of the medically placed tube or line is properly placed. Output of the AI classifier 220 can be stored in the data store 230, for example.

Over time, classifications made by the AI classifier 220 with respect to the same type of input 110, 115 from the data source 210 (e.g., lung MR images of the same patient taken at times t0 and t1, etc.) can be generated and stored in the data store 230. The classifications are provided to the comparator 240, which compares a classification at two or more different times (e.g., prior to insertion of the tube or line and after the insertion of the tube or line) to identify the medically placed tube or line and determine whether the medically placed tube or line is properly placed. For example, at time t0 the tube or line may not present in the region of interest and at time t1 or a later time the tube or line may be placed in a location (which may or may not be properly placed) within the region of interest.

The comparator 240 provides a result indicative of the trend/progression. In certain embodiments, the comparator 240 provides a result indicative of a placement of a medically placed tube or line. The output generator 250 transforms that result into an output that can be displayed, stored, provided to another system for further processing such as an alert, a notification or order, an adjustment in patient care, (e.g., a point of care alert system, an imaging/radiology workstation, a computer-aided diagnosis (CAD) processor, a scheduling system, a medical device, etc.), etc.

The trigger 260 coordinates actions among the data source 210, the AI classifier 220, the data store 230, the comparator 240, and the output generator 250. The trigger 260 can initiate input of data from the data source 210 to the classifier 220, comparison of results from the data store 230 by the comparator 240, output by the output generator 250. Thus, the trigger 260 serves as a coordinator among elements of the apparatus 200.

Figure 3:
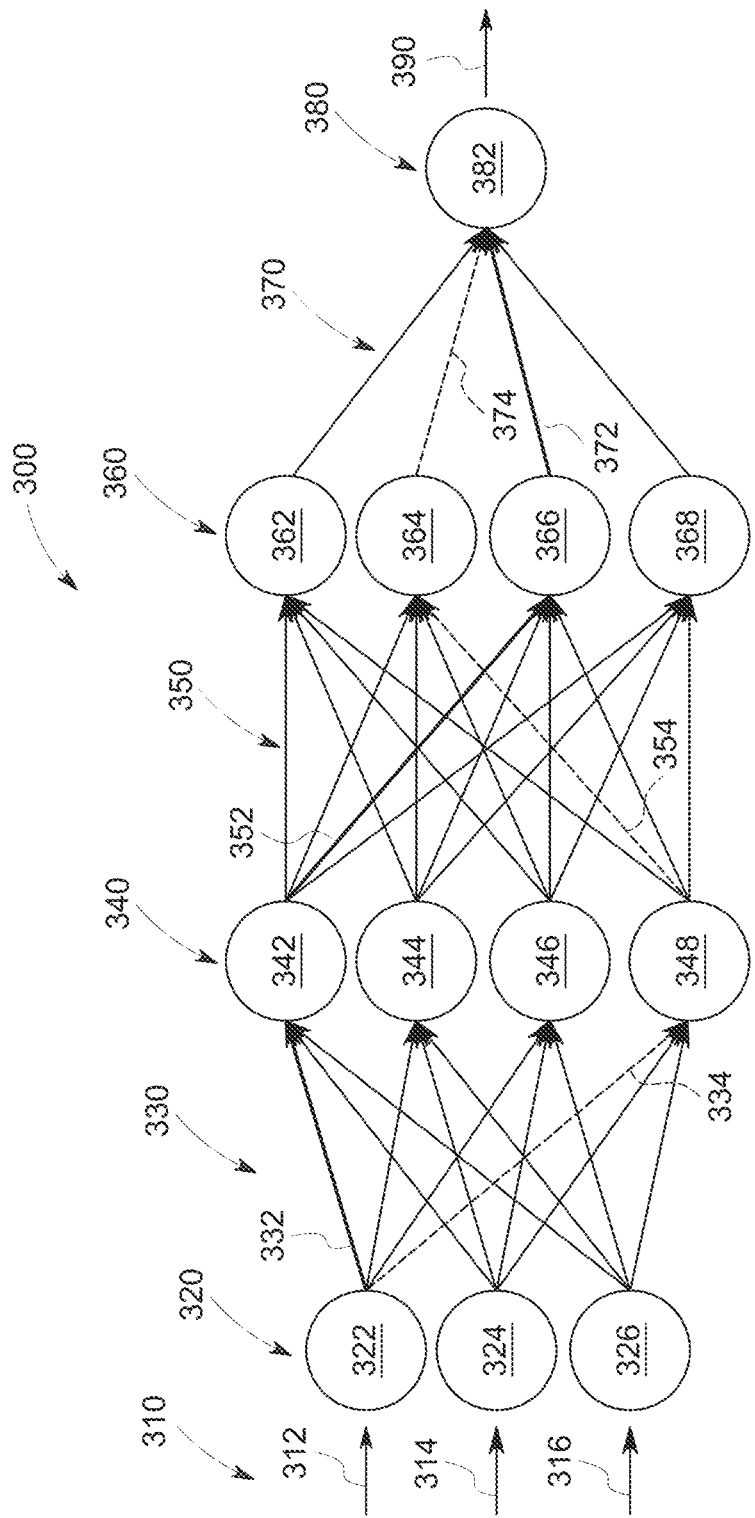
FIG. 3 is a schematic diagram of an embodiment of a learning neural network.

FIG. 3 is a representation of an example learning neural network 300. The example neural network 300 includes layers 320, 340, 360, and 380. The layers 320 and 340 are connected with neural connections 330. The layers 340 and 360 are connected with neural connections 350. The layers 360 and 380 are connected with neural connections 370. Data flows forward via inputs 312, 314, 316 from the input layer 320 to the output layer 380 and to an output 390.

The layer 320 is an input layer that, in the example of FIG. 3, includes a plurality of nodes 322, 324, 326. The layers 340 and 360 are hidden layers and include, in the example of FIG. 3, nodes 342, 344, 346, 348, 362, 364, 366, 368. The neural network 300 may include more or less hidden layers 340 and 360 than shown. The layer 380 is an output layer and includes, in the example of FIG. 3, a node 382 with an output 390. Each input 312-316 corresponds to a node 322-326 of the input layer 320, and each node 322-326 of the input layer 320 has a connection 330 to each node 342-348 of the hidden layer 340. Each node 342-348 of the hidden layer 340 has a connection 350 to each node 362-368 of the hidden layer 360. Each node 362-368 of the hidden layer 360 has a connection 370 to the output layer 380. The output layer 380 has an output 390 to provide an output from the example neural network 300.

Of connections 330, 350, and 370 certain example connections 332, 352, 372 may be given added weight while other example connections 334, 354, 374 may be given less weight in the neural network 300. Input nodes 322-326 are activated through receipt of input data via inputs 312-316, for example. Nodes 342-348 and 362-368 of hidden layers 340 and 360 are activated through the forward flow of data through the network 300 via the connections 330 and 350, respectively. Node 382 of the output layer 380 is activated after data processed in hidden layers 340 and 360 is sent via connections 370. When the output node 382 of the output layer 380 is activated, the node 382 outputs an appropriate value based on processing accomplished in hidden layers 340 and 360 of the neural network 300.

Figure 4:
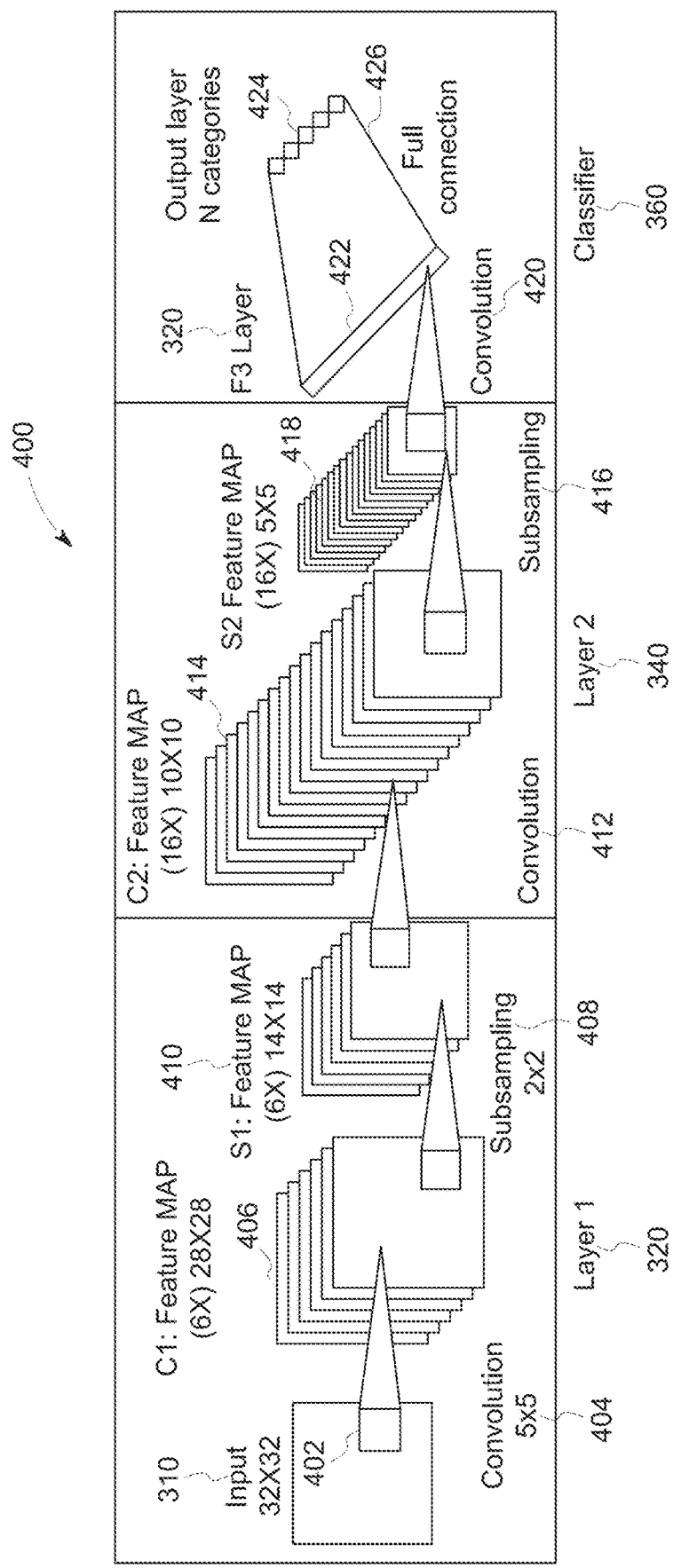
FIG. 4 is a schematic diagram of an embodiment of a particular implementation of the neural network in FIG. 3 as a convolutional neural network.

FIG. 4 illustrates a particular implementation of the example neural network 300 as a convolutional neural network 400. As shown in the example of FIG. 4, an input 310 is provided to the first layer 320 which processes and propagates the input 310 to the second layer 340. The input 310 is further processed in the second layer 340 and propagated to the third layer 360. The third layer 360 categorizes data to be provided to the output layer 380. More specifically, as shown in the example of FIG. 4, a convolution 404 (e.g., a 5×5 convolution, etc.) is applied to a portion or window (also referred to as a "receptive field") 402 of the input 310 (e.g., a 32×32 data input, etc.) in the first layer 320 to provide a feature map 406 (e.g., a (6×) 28×28 feature map, etc.). The convolution 404 maps the elements from the input 310 to the feature map 406. The first layer 320 also provides subsampling (e.g., 2×2 subsampling, etc.) to generate a reduced feature map 410 (e.g., a (6×) 14×14 feature map, etc.). The feature map 410 undergoes a convolution 412 and is propagated from the first layer 320 to the second layer 340, where the feature map 410 becomes an expanded feature map 414 (e.g., a (16×) 10×10 feature map, etc.). After subsampling 416 in the second layer 340, the feature map 414 becomes a reduced feature map 418 (e.g., a (16×) 4×5 feature map, etc.). The feature map 418 undergoes a convolution 420 and is propagated to the third layer 360, where the feature map 418 becomes a classification layer 422 forming an output layer of N categories 424 with connection 426 to the convoluted layer 422, for example.

Figure 5:
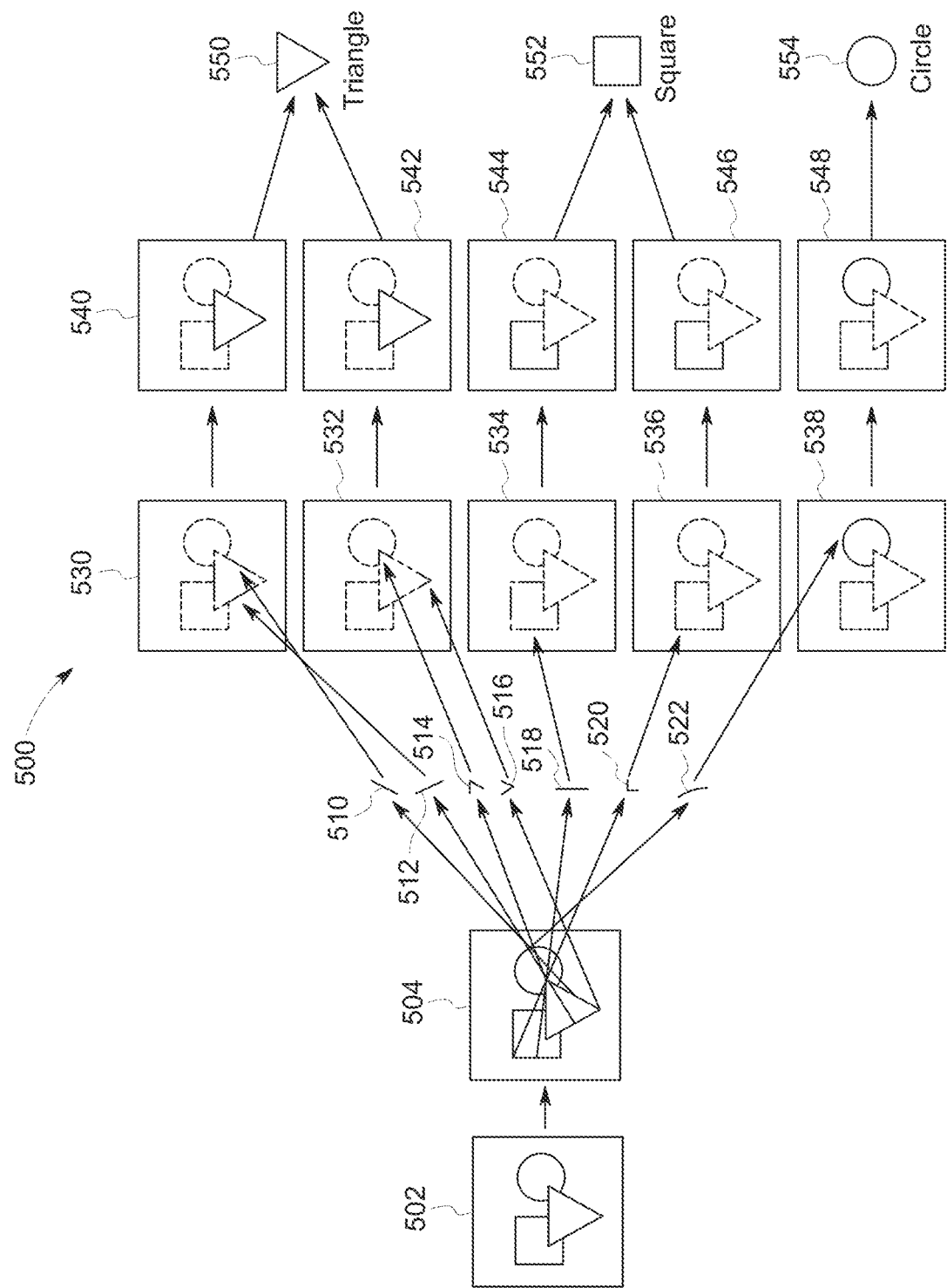
FIG. 5 is a schematic diagram of an embodiment of an image analysis convolutional neural network.

FIG. 5 is a representation of an example implementation of an image analysis convolutional neural network 500. The convolutional neural network 500 receives an input image 502 and abstracts the image in a convolution layer 504 to identify learned features 510-522. In a second convolution layer 530, the image is transformed into a plurality of images 530-538 in which the learned features 510-522 are each accentuated in a respective sub-image 530-538. The images 530-538 are further processed to focus on the features of interest 510-522 in images 540-548. The resulting images 540-548 are then processed through a pooling layer which reduces the size of the images 540-548 to isolate portions 550-554 of the images 540-548 including the features of interest 510-522. Outputs 550-554 of the convolutional neural network 500 receive values from the last non-output layer and classify the image based on the data received from the last non-output layer. In certain examples, the convolutional neural network 500 may contain many different variations of convolution layers, pooling layers, learned features, and outputs, etc.

FIG. 6A illustrates an example configuration 600 to apply a learning (e.g., machine learning, deep learning, etc.) network to process and/or otherwise evaluate an image. Machine learning can be applied to a variety of processes including image acquisition, image reconstruction, image analysis/diagnosis, etc. As shown in the example configuration 600 of FIG. 6A, raw data 610 (e.g., raw data 610 such as sonogram raw data, etc., obtained from an imaging scanner such as an x-ray, computed tomography, ultrasound, magnetic resonance, etc., scanner) is fed into a learning network 620. The learning network 620 processes the data 610 to correlate and/or otherwise combine the raw data 620 into processed data 630 (e.g., a resulting image, etc.) (e.g., a "good quality" image and/or other image providing sufficient quality for diagnosis, etc.). The learning network 620 includes nodes and connections (e.g., pathways) to associate raw data 610 with the processed data 630. The learning network 620 can be a training network that learns the connections and processes feedback to establish connections and identify patterns, for example. The learning network 620 can be a deployed network that is generated from a training network and leverages the connections and patterns established in the training network to take the input raw data 610 and generate the resulting image 630, for example.

Once the learning 620 is trained and produces good images 630 from the raw image data 610, the network 620 can continue the "self-learning" process and refine its performance as it operates. For example, there is "redundancy" in the input data (raw data) 610 and redundancy in the network 620, and the redundancy can be exploited.

If weights assigned to nodes in the learning network 620 are examined, there are likely many connections and nodes with very low weights. The low weights indicate that these connections and nodes contribute little to the overall performance of the learning network 620. Thus, these connections and nodes are redundant. Such redundancy can be evaluated to reduce redundancy in the inputs (raw data) 610. Reducing input 610 redundancy can result in savings in scanner hardware, reduced demands on components, and also reduced exposure dose to the patient, for example.

In deployment, the configuration 600 forms a package including an input definition 610, a trained network 620, and an output definition 630. The package can be deployed and installed with respect to another system, such as an imaging system, analysis engine, etc. An image enhancer 625 can leverage and/or otherwise work with the learning network 620 to process the raw data 610 and provide a result (e.g., processed image data and/or other processed data 630, etc.). The pathways and connections between nodes of the trained learning network 620 enable the image enhancer 625 to process the raw data 610 to form the image and/or other processed data result 630, for example.

As shown in the example of FIG. 6B, the learning network 620 can be chained and/or otherwise combined with a plurality of learning networks 621-623 to form a larger learning network. The combination of networks 620-623 can be used to further refine responses to inputs and/or allocate networks 620-623 to various aspects of a system, for example.

In some examples, in operation, "weak" connections and nodes can initially be set to zero. The learning network 620 then processes its nodes in a retaining process. In certain examples, the nodes and connections that were set to zero are not allowed to change during the retraining. Given the redundancy present in the network 620, it is highly likely that equally good images will be generated. As illustrated in FIG. 6B, after retraining, the learning network 620 becomes DLN 621. The learning network 621 is also examined to identify weak connections and nodes and set them to zero. This further retrained network is learning network 622. The example learning network 622 includes the "zeros" in learning network 621 and the new set of nodes and connections.

The learning network 622 continues to repeat the processing until a good image quality is reached at a learning network 623, which is referred to as a "minimum viable net (MVN)". The learning network 623 is a MVN because if additional connections or nodes are attempted to be set to zero in learning network 623, image quality can suffer.

Once the MVN has been obtained with the learning network 623, "zero" regions (e.g., dark irregular regions in a graph) are mapped to the input 610. Each dark zone is likely to map to one or a set of parameters in the input space. For example, one of the zero regions may be linked to the number of views and number of channels in the raw data. Since redundancy in the network 623 corresponding to these parameters can be reduced, there is a highly likelihood that the input data can be reduced and generate equally good output. To reduce input data, new sets of raw data that correspond to the reduced parameters are obtained and run through the learning network 621. The network 620-623 may or may not be simplified, but one or more of the learning networks 620-623 is processed until a "minimum viable input (MVI)" of raw data input 610 is reached. At the MVI, a further reduction in the input raw data 610 may result in reduced image 630 quality. The MVI can result in reduced complexity in data acquisition, less demand on system components, reduced stress on patients (e.g., less breath-hold or contrast), and/or reduced dose to patients, for example.

By forcing some of the connections and nodes in the learning networks 620-623 to zero, the network 620-623 builds "collaterals" to compensate. In the process, insight into the topology of the learning network 620-623 is obtained. Note that network 621 and network 622, for example, have different topologies since some nodes and/or connections have been forced to zero. This process of effectively removing connections and nodes from the network extends beyond "deep learning" and can be referred to as "deep-deep learning", for example.

In certain examples, input data processing and deep learning stages can be implemented as separate systems. However, as separate systems, neither module may be aware of a larger input feature evaluation loop to select input parameters of interest/importance. Since input data processing selection matters to produce high-quality outputs, feedback from deep learning systems can be used to perform input parameter selection optimization or improvement via a model. Rather than scanning over an entire set of input parameters to create raw data (e.g., which is brute force and can be expensive), a variation of active learning can be implemented. Using this variation of active learning, a starting parameter space can be determined to produce desired or "best" results in a model. Parameter values can then be randomly decreased to generate raw inputs that decrease the quality of results while still maintaining an acceptable range or threshold of quality and reducing runtime by processing inputs that have little effect on the model's quality.

Figure 7:
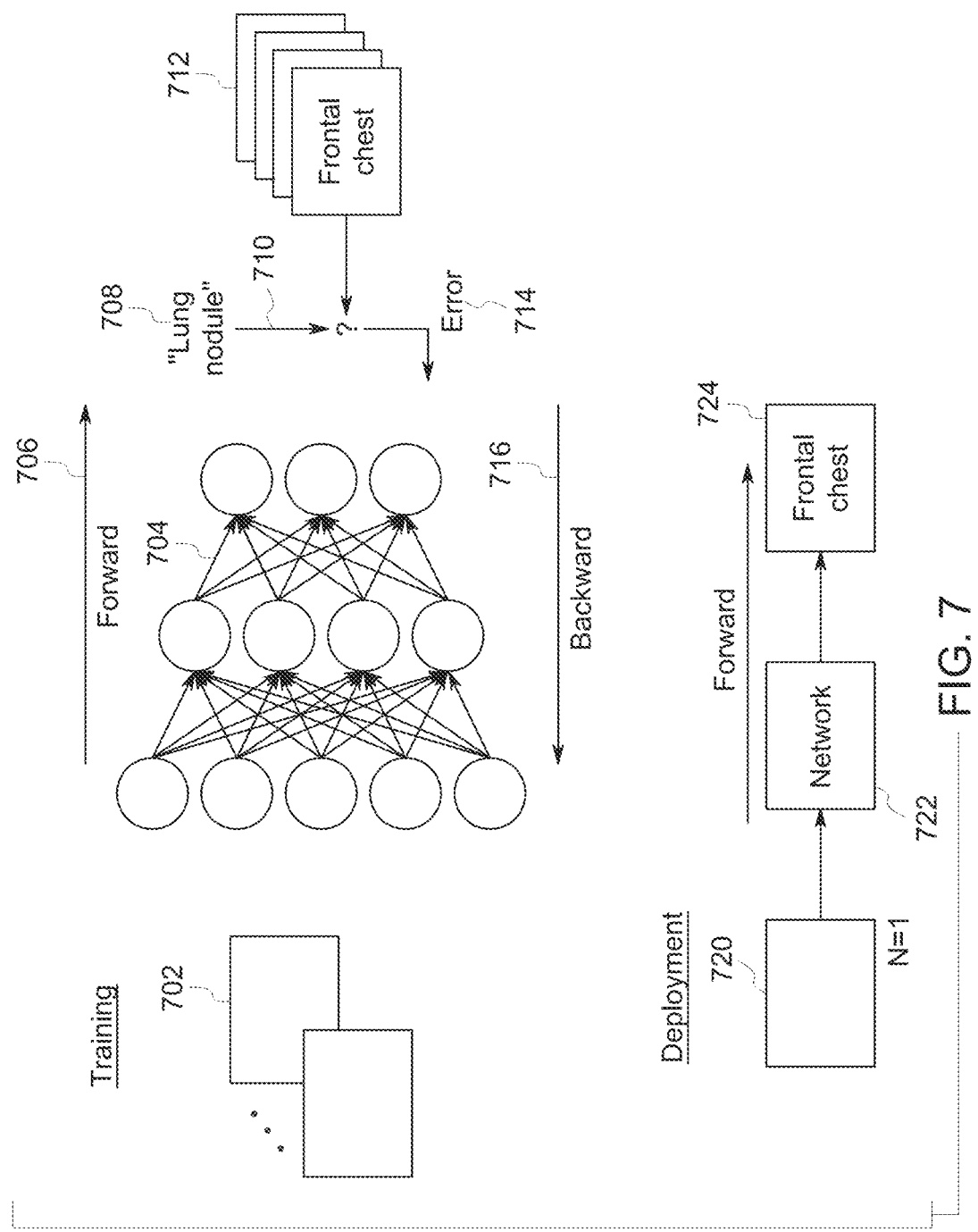
FIG. 7 is a schematic diagram of an embodiment for training and deployment phases of a learning network.

FIG. 7 illustrates example training and deployment phases of a learning network, such as a deep learning or other machine learning network. As shown in the example of FIG. 7, in the training phase, a set of inputs 702 is provided to a network 704 for processing. In this example, the set of inputs 702 can include features of an image to be identified. The network 704 processes the input 702 in a forward direction 706 to associate data elements and identify patterns. The network 704 determines that the input 702 represents a lung nodule 708. In training, the network result 708 is compared 710 to a known outcome 712. In this example, the known outcome 712 is a frontal chest (e.g., the input data set 702 represents a frontal chest identification, not a lung nodule). Since the determination 708 of the network 704 does not match 710 the known outcome 712, an error 714 is generated. The error 714 triggers an analysis of the known outcome 712 and associated data 702 in reverse along a backward pass 716 through the network 704. Thus, the training network 704 learns from forward 706 and backward 716 passes with data 702, 712 through the network 704.

Figure 8:
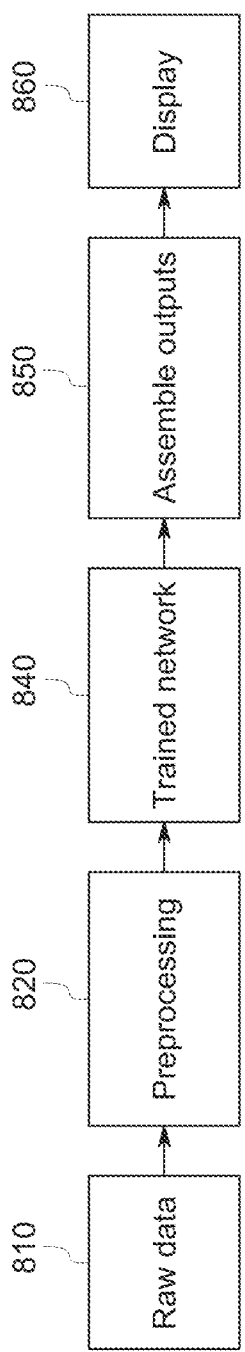
FIG. 8 is a schematic diagram of an embodiment of a product leveraging a trained network package to provide a deep learning product offering.

Once the comparison of network output 708 to known output 712 matches 710 according to a certain criterion or threshold (e.g., matches n times, matches greater than x percent, etc.), the training network 704 can be used to generate a network for deployment with an external system. Once deployed, a single input 720 is provided to a deployed learning network 722 to generate an output 724. In this case, based on the training network 704, the deployed network 722 determines that the input 720 is an image of a frontal chest 724. This same approach may be utilized in determining a tube or line, a reference or anatomical landmark, and/or the proper placement of the tube or line FIG. 8 illustrates an example product leveraging a trained network package to provide a deep and/or other machine learning product offering. As shown in the example of FIG. 8, an input 810 (e.g., raw data) is provided for preprocessing 820. For example, the raw input data 810 is preprocessed 820 to check format, completeness, etc. Once the data 810 has been preprocessed 820, it is fed into a trained network 840 for processing. Based on learned patterns, nodes, and connections, the trained network 840 determines outputs based on the input patches. The outputs are assembled 850 (e.g., combined and/or otherwise grouped together to generate a usable output, etc.). The output is then displayed 860 and/or otherwise output to a user (e.g., a human user, a clinical system, an imaging modality, a data storage (e.g., cloud storage, local storage, edge device, etc.), etc.).

Figure 9A:
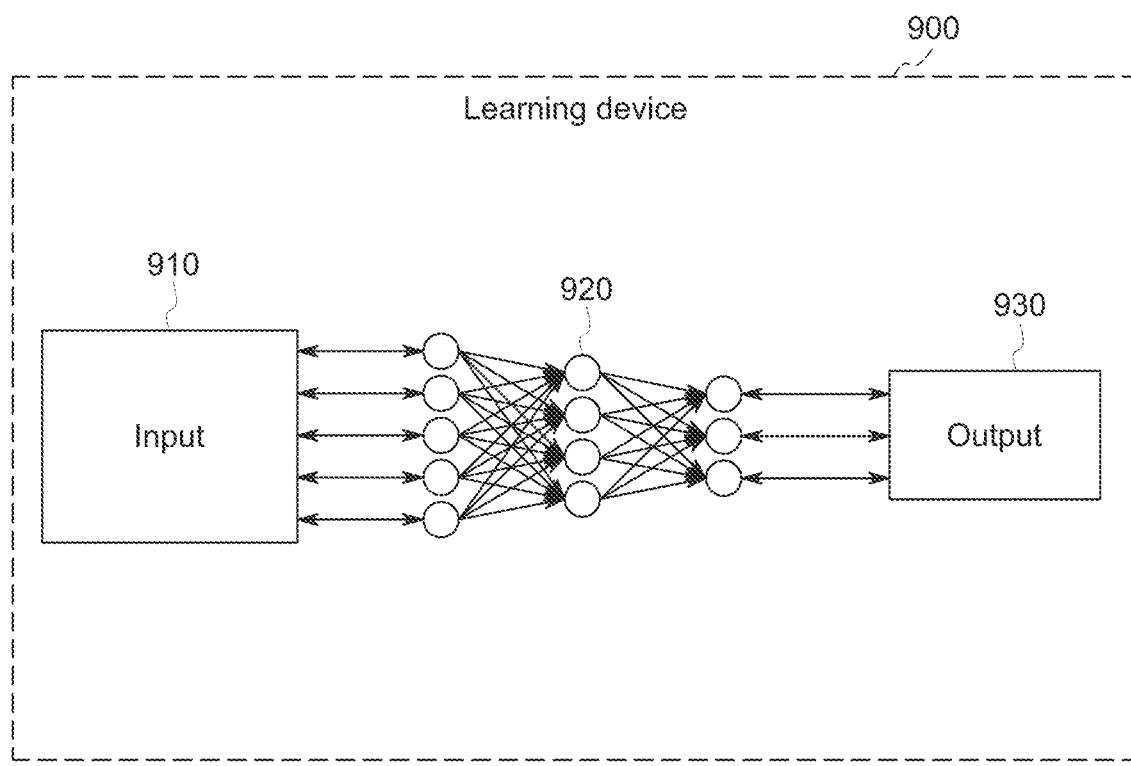
FIGS. 9A-9C are schematic diagrams of respective embodiments of various deep learning device configurations.
Figure 9B:
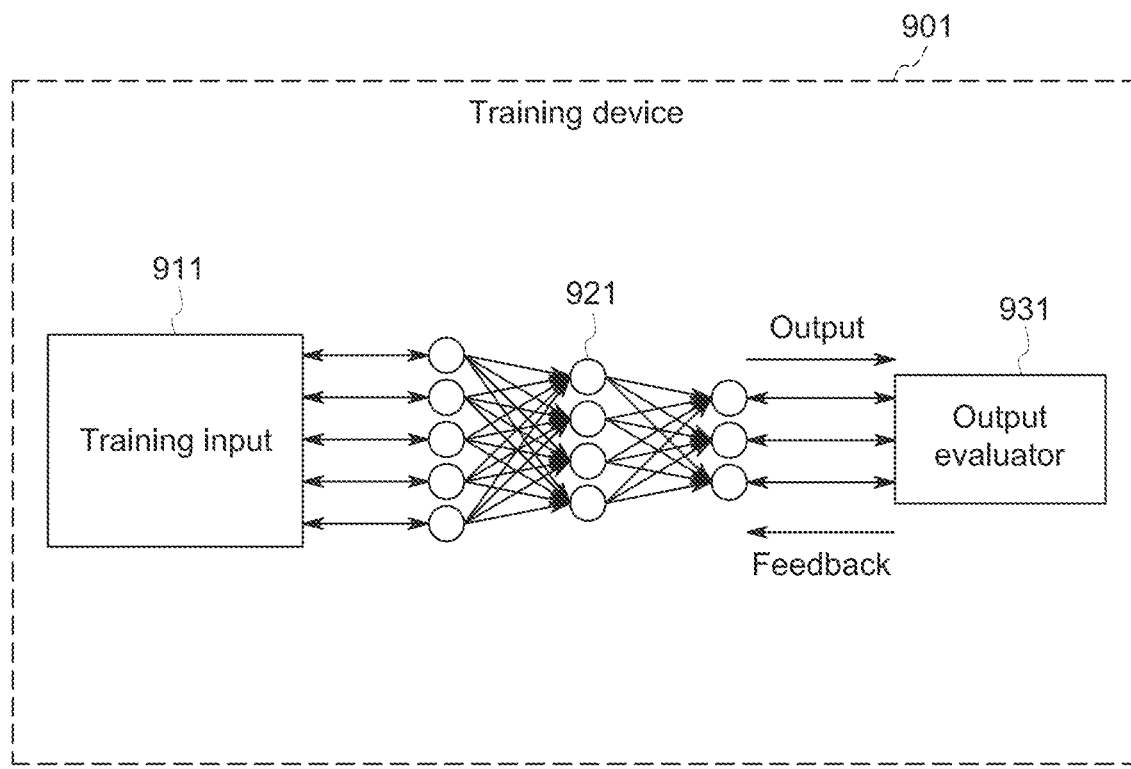
Figure 9C:
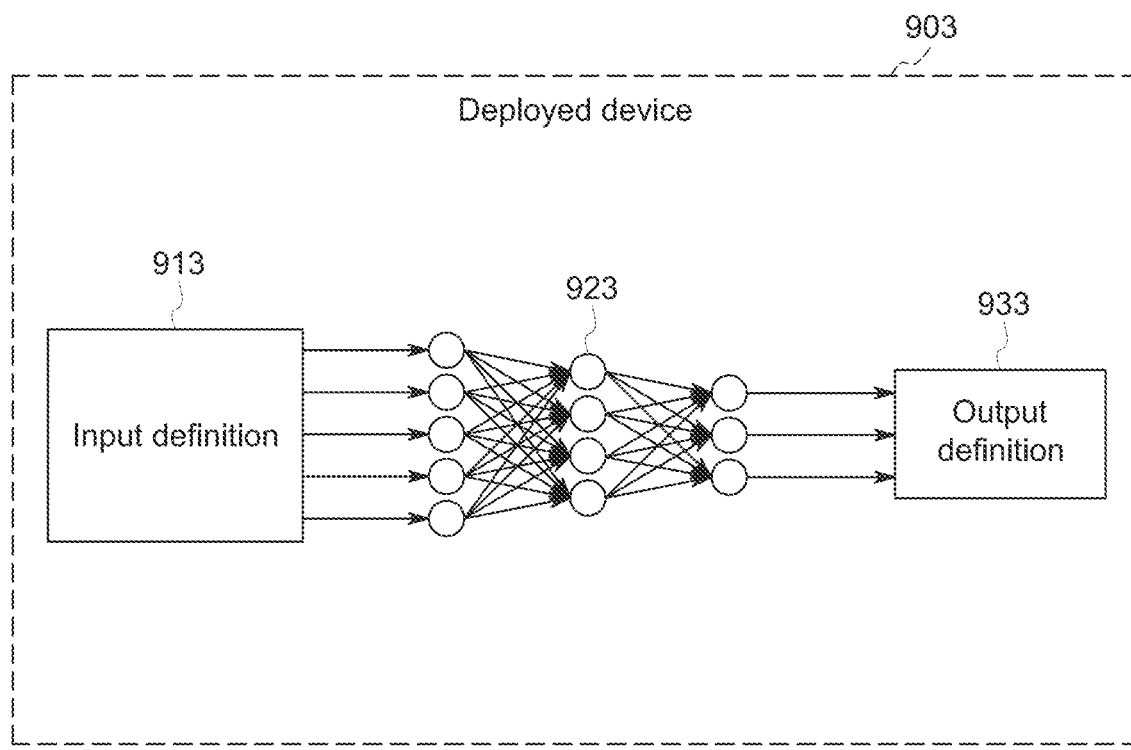

As discussed above, learning networks can be packaged as devices for training, deployment, and application to a variety of systems. FIGS. 9A-9C illustrate various learning device configurations. For example, FIG. 9A shows a general learning device 900. The example device 900 includes an input definition 910, a learning network model 920, and an output definition 930. The input definition 910 can include one or more inputs translating into one or more outputs 930 via the network 920.

FIG. 9B shows an example training device 901. That is, the training device 901 is an example of the device 900 configured as a training learning network device. In the example of FIG. 9B, a plurality of training inputs 911 are provided to a network 921 to develop connections in the network 921 and provide an output to be evaluated by an output evaluator 931. Feedback is then provided by the output evaluator 931 into the network 921 to further develop (e.g., train) the network 921. Additional input 911 can be provided to the network 921 until the output evaluator 931 determines that the network 921 is trained (e.g., the output has satisfied a known correlation of input to output according to a certain threshold, margin of error, etc.).

FIG. 9C depicts an example deployed device 903. Once the training device 901 has learned to a requisite level, the training device 901 can be deployed for use. While the training device 901 processes multiple inputs to learn, the deployed device 903 processes a single input to determine an output, for example. As shown in the example of FIG. 9C, the deployed device 903 includes an input definition 913, a trained network 923, and an output definition 933. The trained network 923 can be generated from the network 921 once the network 921 has been sufficiently trained, for example. The deployed device 903 receives a system input 913 and processes the input 913 via the network 923 to generate an output 933, which can then be used by a system with which the deployed device 903 has been associated, for example.

In certain examples, condition identification (e.g., placement of a tube or line) and progression can be determined through AI-driven analysis of associated image data for a patient.

Figure 10:
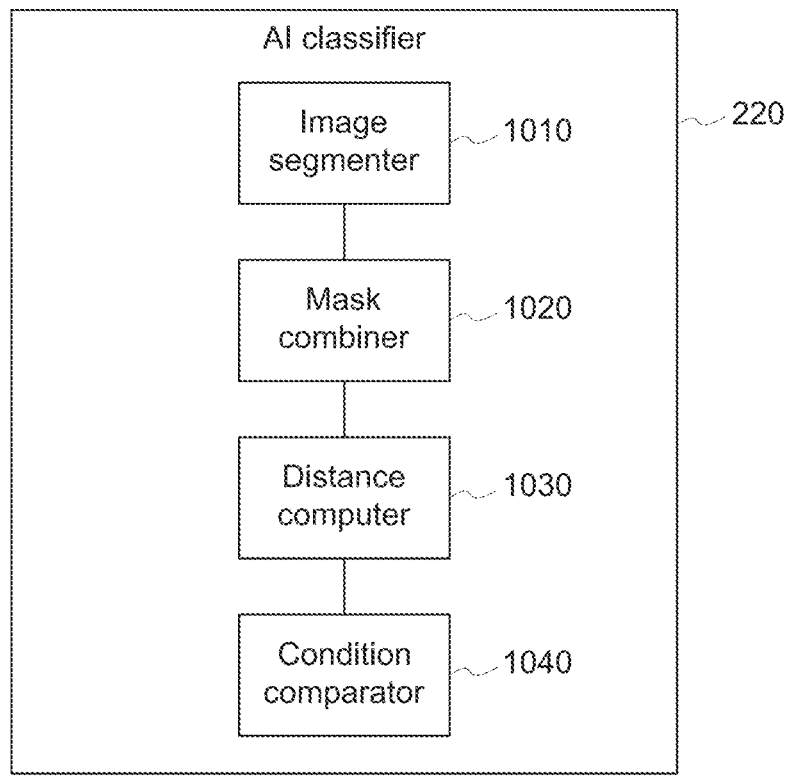
FIG. 10 is a schematic diagram of an embodiment of an implementation of the artificial intelligence classifier of FIG. 2 to process image data to be used by an artificial intelligence model to quantify a condition.

FIG. 10 illustrates an example implementation of the AI classifier 220 to process image data to be used by an AI model to quantify a condition (e.g., placement of a tube or line). The example implementation of the classifier 220 enables annotation of one or more images including an organ region and a region of interest within the organ region. The example classifier 220 of FIG. 10 includes an image segmenter 1010, a mask combiner 1020, and a condition comparator 1040.

The example image segmenter 1010 is to identify a first mask and a second mask in an input image. For example, the image segmenter 1010 processes the image to segment a region of interest within an organ region identified in the image to obtain a first mask. The first mask is a segmentation mask and may be embodied as a filter that includes the region of interest in the image and excludes the remainder of the image. The mask can be applied to image data to exclude all but the region of interest, for example. The mask can be obtained using a convolutional neural network model, for example, such as the network 400, 500 shown in FIGS. 4-5, a generative adversarial network, etc. The image segmenter 1010 further processes the image to segment the organ region according to one or more criterion to obtain a second mask. For example, the second mask can represent the organ region, an area of the organ region outside the region of interest, etc.

For example, if the organ region is a lung (and the surrounding area such as the trachea), and the region of interest is a tube or line identified in the trachea, the first mask is generated to identify the medically placed tube or line, and the second mask is generated to identify the entire organ region. In another embodiment, if the organ region is a stomach, and the region of interest is a tube or line identified in the in the stomach, the first mask is generated to identify the medically placed tube or line, and the second mask is generated to identify the entire organ region. In a further embodiment, if the organ region is a heart (and the surrounding area such as veins or other vasculature), and the region of interest is a tube or line identified in a vein or other vasculature near the heart, the first mask is generated to identify the medically placed tube or line, and the second mask is generated to identify the entire organ region. Thus, in regards to a medically placed tube or line, a first mask is generated for the tube or line and a second mask is generated for the entire organ region where the tube or line is placed (e.g., vasculature system, heart, lung, stomach, trachea, chest, pleural space, etc.).

The example combiner 1020 combines the first mask and the second mask and associated areas with annotation terms in the image. Annotations can be relative qualification terms to produce quantification. For example, mask areas can be combined with descriptive terms such as foggy, patchy, dense, etc., to compute relative density values for the region of interest and organ region in the image. Image areas (e.g., areas of frontal and lateral images, etc.) can be combined to produce a volume metric, for example.

The example distance computer 1030 determines a distance between a surface and/or an end of an identified tube or line and a reference or anatomical landmark (or determines a position of the tube or line relative to the landmark). The example condition comparator 1040 compares the distance or measured positions to a preset distance or desired position for the type of tube or line and/or region of interest where the tube or line is placed (e.g., in accordance with predetermined rules). Based on this comparison, the condition comparator 1040 can determine whether the end of the tube or line is properly placed relative to the reference or anatomical landmark.

Thus, the AI classifier 220 can be configured to annotate a medical image or set of related medical image(s) for AI/machine learning/deep learning/CAD algorithm training, to quantify conditions. Such methods are consistent, repeatable methodologies which could replace common subjective methods of today, enabling automatic, accurate detection of the presence of a medically placed tube or line and its placement.

While example implementations are illustrated in conjunction with FIGS. 1-10, elements, processes and/or devices illustrated in conjunction with FIGS. 1-10 can be combined, divided, re-arranged, omitted, eliminated and/or implemented in any other way. Further, components disclosed and described herein can be implemented by hardware, machine readable instructions, software, firmware and/or any combination of hardware, machine readable instructions, software and/or firmware. Thus, for example, components disclosed and described herein can be implemented by analog and/or digital circuit(s), logic circuit(s), programmable processor(s), application specific integrated circuit(s) (ASIC(s)), programmable logic device(s) (PLD(s)) and/or field programmable logic device(s) (FPLD(s)). When reading any of the apparatus or system claims of this patent to cover a purely software and/or firmware implementation, at least one of the components is/are hereby expressly defined to include a tangible computer readable storage device or storage disk such as a memory, a digital versatile disk (DVD), a compact disk (CD), a Blu-ray disk, etc. storing the software and/or firmware.

Figure 11:
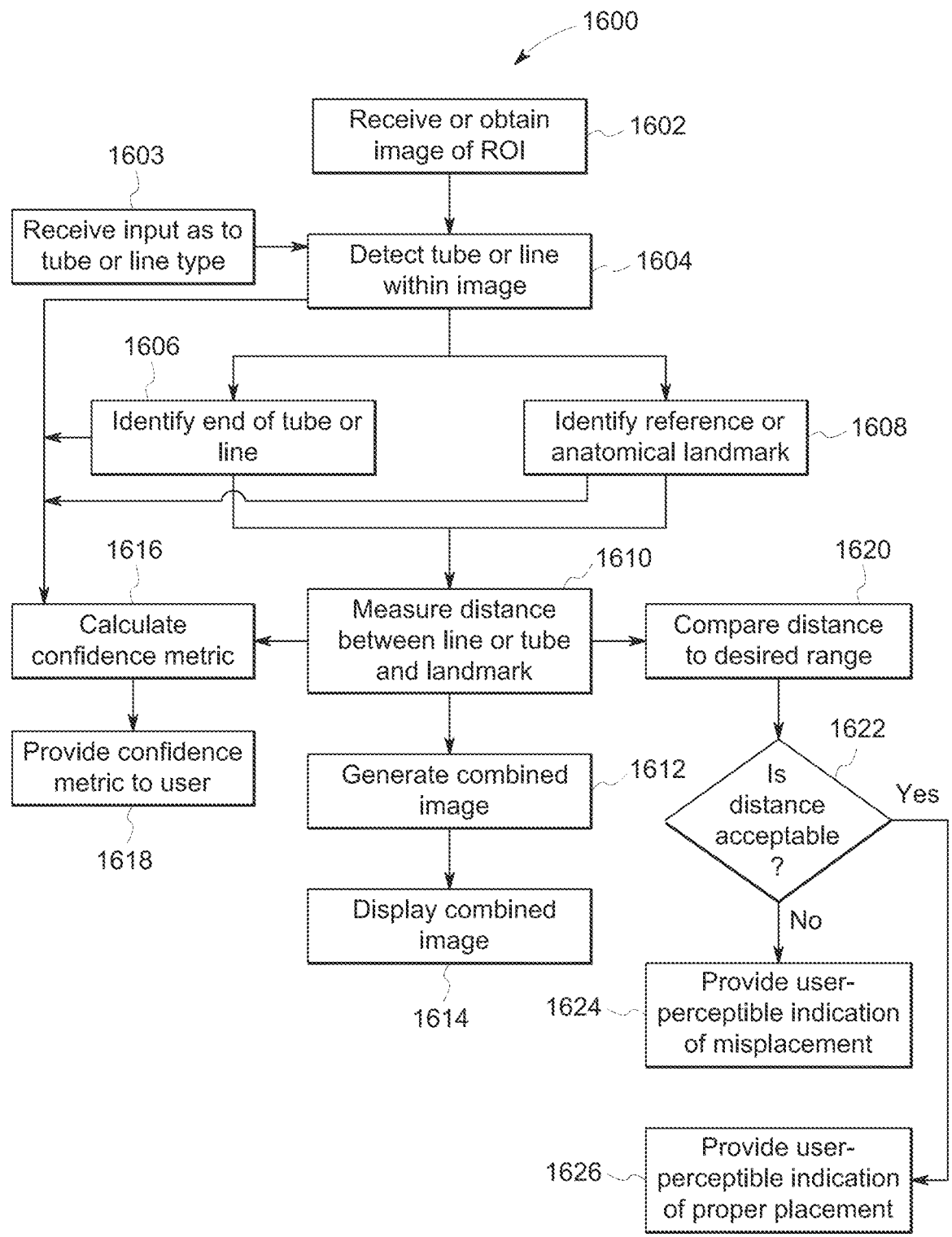
FIG. 11 is a flow diagram of an embodiment of a method for determining a placement of a medically placed tube or line within a region of interest.

A flowchart representative of example machine readable instructions for implementing aspects or embodiments of the presently disclosed techniques described herein are shown in conjunction with at least FIG. 11. In the examples, the machine readable instructions include a program for execution by a processor such as the processor 1312 shown in the example processor platform 1300 discussed below in connection with FIG. 35. The program may be embodied in machine readable instructions stored on a tangible computer readable storage medium such as a CD-ROM, a floppy disk, a hard drive, a digital versatile disk (DVD), a Blu-ray disk, or a memory associated with the processor 1312, but the entire program and/or parts thereof could alternatively be executed by a device other than the processor 1312 and/or embodied in firmware or dedicated hardware. Further, although the example program is described with reference to the flowchart illustrated in conjunction with at least FIG. 11, many other methods of implementing the components disclosed and described herein may alternatively be used. For example, the order of execution of the blocks may be changed, and/or some of the blocks described may be changed, eliminated, or combined. Although the flowchart of at least FIG. 11 depicts an example operation in an illustrated order, these operations are not exhaustive and are not limited to the illustrated order. In addition, various changes and modifications may be made by one skilled in the art within the spirit and scope of the disclosure. For example, blocks illustrated in the flowchart may be performed in an alternative order or may be performed in parallel.

As mentioned above, the example processes of at least FIG. 11 may be implemented using coded instructions (e.g., computer and/or machine readable instructions) stored on a tangible computer readable storage medium such as a hard disk drive, a flash memory, a read-only memory (ROM), a compact disk (CD), a digital versatile disk (DVD), a cache, a random-access memory (RAM) and/or any other storage device or storage disk in which information is stored for any duration (e.g., for extended time periods, permanently, for brief instances, for temporarily buffering, and/or for caching of the information). As used herein, the term tangible computer readable storage medium is expressly defined to include any type of computer readable storage device and/or storage disk and to exclude propagating signals and to exclude transmission media. As used herein, "tangible computer readable storage medium" and "tangible machine readable storage medium" are used interchangeably. Additionally or alternatively, the example processes of at least FIG. 11 can be implemented using coded instructions (e.g., computer and/or machine readable instructions) stored on a non-transitory computer and/or machine readable medium such as a hard disk drive, a flash memory, a read-only memory, a compact disk, a digital versatile disk, a cache, a random-access memory and/or any other storage device or storage disk in which information is stored for any duration (e.g., for extended time periods, permanently, for brief instances, for temporarily buffering, and/or for caching of the information). As used herein, the term non-transitory computer readable medium is expressly defined to include any type of computer readable storage device and/or storage disk and to exclude propagating signals and to exclude transmission media. As used herein, when the phrase "at least" is used as the transition term in a preamble of a claim, it is open-ended in the same manner as the term "comprising" is open ended. In addition, the term "including" is open-ended in the same manner as the term "comprising" is open-ended.

As mentioned above, these techniques may be utilized to identify a medically placed tube or line and to determine if medically placed tube or line is properly placed. For example, the medically placed tube or line may be an enteric tube and the proper placement of the enteric tube may be determined. Such examples are intended to be non-limiting, and any other tube or line inserted within a region of interest of the body may be identified and its proper placement determined.

FIG. 11 is a flow diagram of an embodiment of a method 1600 for determining a placement of a medically placed tube or line within a region of interest. One or more steps of the method may be performed by the processor platform 1600 in FIG. 35. One or more steps of the depicted steps may be performed simultaneously or in a different order from what is illustrated in FIG. 11. The method 1600 includes receiving or obtaining an image (e.g., chest image) of a patient that includes a region of interest (ROI) (block 1602). The image may include a medically placed tube or line inserted within the region of interest. The image may be provided while the patient has the tube or line inserted. The method 1600 also includes receiving or obtaining an input regarding the type of tube or line to be detected (e.g., a nasogastric or other enteric tube) and/or the region of interest for tube or line to be inserted within (e.g., trachea, stomach, gastrointestinal tract) (block 1603). The input may be a user defined distance or rules for defining the proper placement of the end of the medically placed tube or line relative to a reference or anatomical location. In certain embodiments, the input may simply be the type of tube or line and/or the desired region of interest for the tube or line to be properly placed within. Based on this input, certain defined distances or rules (e.g., left, right, above, and/or below a specific anatomical location) may be utilized that define a proper placement of the end of the specific tube or line within a specific region of interest. The method 1600 also includes detecting the tube or line within the image (block 1604) utilizing the techniques described herein. The method 1600 includes identifying a surface and/or an end (e.g., distal end) of the tube or line within the region of interest in the image (block 1606). The method 1600 also includes identifying a reference or anatomical landmark within the image (block 1608). The reference or anatomical landmark will vary based on the type of tube or line utilized and the region of interest that the tube or line is disposed within. For example, for a nasogastric tube, the reference or anatomical landmark(s) may include, but are not limited to a patient's airway and diaphragm and/or a location within the stomach below the gastroesophageal junction.

Upon identifying the surfaces and/or distal end of the tube or line and the reference or anatomical landmark(s), the method 1600 may include measuring a distance (e.g., between the end of the tube or line and the reference or anatomical landmark) (block 1610) that may be reported to a user and/or used in automated placement evaluation. The method 1600 includes generating a combined image with indications of the tube or line, the reference or anatomical landmark(s), and/or the measured distance (block 1612). Generating the combined image includes superimposing various markers on the received image of the patient. For example, a color coding (e.g., color coded graphical overlay) may be superimposed on the detected tube or line. In certain embodiments, the patient may include more than one tube or line and the tube or line of interest is color coded. A graphical marker may be superimposed on the image to indicate the end of the line or tube. Another graphical marker may be superimposed on the image to indicate the reference or anatomical landmark. The graphical markers may include the same shape or different shapes. Non-limiting examples of the shapes may be an open circle or other elliptical shape, open rectilinear shape, open triangular shape, or another shape. The graphical marker(s) and/or the tube may be color coded with different colors. For example, the graphical marker for the tube or line, the graphical marker for the reference or anatomical landmark, and the tube or line may be green, blue, and yellow, respectively. A graphical marker may also be superimposed on the image indicating a distance between the end of the tube or line and the reference or anatomical landmark when a distance is calculated. The graphical marker for the distance may also include the measurement value. The method 1600 further includes displaying the combined image on a display (block 1614). The combined image may be displayed in real-time to the medical personnel enabling them to adjust the placement of the tube or line if need be. In certain embodiments, the combined image may be displayed as a DICOM image.

In certain embodiments, the method 1600 includes calculating one or more respective confidence metrics (block 1616). The confidence metrics may be for the calculated distance, for the determination of the presence of the medically placed tube or line, for an accuracy in detecting the placement of the tube or line, and/or for an accuracy in detecting the reference or anatomical landmark. The confidence metric may include a confidence level or confidence interval. The confidence metric may be stored for future reference. In certain embodiments, the method 1600 may include providing one or more of the confidence metrics to a user (block 1618). For example, the confidence metrics may be displayed on the combined image or provided on a separate device (e.g., user's device). In certain embodiments, the confidence metrics may be written into a standard or private information tag (e.g., DICOM) and made visible in subsequent information systems that the image is sent too (e.g., PACS).

In certain embodiments, in determining whether the medically placed tube or line is placed properly (e.g., via the deep learning networks models), the method 1600 includes comparing the measured distance between the surface and/or end of the tube or line and the reference or anatomical landmark to a desired threshold (block 1620) and determining if the distance is acceptable (block 1622). The desired threshold may represent an acceptable range for the distance between the tube or line and the reference or anatomical landmark for the tube or line to be correctly placed. For example, for a nasogastric tube, the desired threshold may be a range of distance below the gastroesophageal junction. If the measured distance is not acceptable, the method 1600 includes providing a user-perceptible indication of misplacement (block 1624). The indication may be provided on the display where the combined image is displayed or provided on another device (e.g., the user's device). The indication may be text stating that the tube or line is misplaced. In certain embodiments, the text may be more specific and state the tube or line is too high or too low or otherwise improper. In certain embodiments, the text may provide further instructions (e.g., to raise or lower the end of the tube or line a certain distance). In some embodiments, the text may be color coded (e.g., in orange or red) to further indicate the misplacement. In some embodiments, the indication may be provided via color coding of one or more graphical markers or the tube or line displayed on the combined image. For the example, one or more of the graphical markers (e.g., for the end of tube or line, for the reference or anatomical landmark, and/or the indication of the measured distance there between) and/or the tube or line may be color coded a specific color (e.g., red or orange) to indicate the misplacement. Alternatively or in addition, one or more of the graphical markers may flash or otherwise be visually highlighted if the tube or line is misplaced. If the measured distance is acceptable, the method 1600 includes providing a user-perceptible indication of proper placement of the tube or line (block 1626). The indication may be provided on the display where the combined image is displayed or provided on another device (e.g., the user's device). The indication for proper placement may be text stating the tube or line is properly placed. In certain embodiments, the indication for proper placement may be provided via color coding one or more graphical markers of the tube or line displayed on the combined image (e.g., all the graphical markers and/or the tube or line may be color coded green). In certain embodiments, the indication of proper placement or misplacement may be written into a standard or private information tag (e.g., DICOM) and made visible in subsequent information systems that the image is sent too (e.g., PACS). In certain embodiments, the determination as to whether the medically placed tube or line is properly placed or positioned may be manually done by the medical personnel viewing the displayed combined image.

With the preceding in mind, and by way of a real-world context and example to facilitate explanation, further illustration of an enteric tube implementation is described below. As used herein, enteric tubes may be understood to be thin flexible hollow catheters that course into the stomach and beyond. In practice, such enteric tubes may or may not include a side port. As may be appreciated, the phrase "enteric tube" may be understood to encompass an array of tube types differentiated by their insertion point (e.g., in the nose (naso-) or mouth (oro-) and by their endpoint (e.g., in the stomach (-gastric), in the duodenum (-duodenal), or in the jejunum (-jejunal). For the purpose of illustration, many of the following examples are presented in the context of a nasogastric tube so as to provide a real-world context. However it should be understood that such examples and discussion may be equally applicable to the other types of enteric tubes and, indeed, to other suitable medical tubes in general.

In the context of a nasogastric tube, it may be understood that the use of such tubes may raise particular issues which may be addressed as explained and shown herein. By way of context, such tubes may typically be implemented as plastic (or other biocompatible material) tubes that are designed to be passed through the nose and into the stomach of a patient. Once properly placed, a nasogastric tube may be used to administer nutrients medication, and/or contrast to the patient. In addition or in the alternative, the placed tube may be used to remove liquids and/or air from the stomach.

With respect to proper placement, a nasogastric tube may be inserted so as to bisect the airways and diaphragm on the X-ray projection (e.g., to be positioned substantially on the midline with respect to the airway). The inserted tip (i.e., distal tip) and side ports (if present) are below the diaphragm when properly placed, typically positioned toward the patient's left hand side. Proper insertion and placement of the tube avoids or mitigates possible risks, such as the risk of insertion into the lungs (with the associated risk of substances entering the lungs), the risk of the tube placement being too high, e.g., in the esophagus, and the risk that loops or kinks in the inserted tube may disturb the flow and/or irritate the patient.

As discussed herein, and in the context of the preceding discussion, the presently described techniques utilize an AI-based feature to facilitate and assess the placement of enteric tubes, including but not limited to nasogastric tubes. The AI-based feature may be used to detect and/or characterize the placed tube, to provide a graphical summary showing the tube with respect to relevant anatomical features (e.g., in the actual anatomical context), and to classify the tube as being placed correctly or needing adjustment. Use of the AI-based feature may, therefore, increase the confidence of the bedside team when placing tubes. Use of the Ai-based feature may also facilitate prioritization of potentially misplaced tubes for review, such as by a radiologist, and may speed up the review process, thereby helping to avoid complications associated with misplaced tubes.

Features and benefits provided by the techniques described herein include, but are not limited to: the ability to localize particular features (e.g., the tube tip, side port, end port, and so forth) of the enteric tube; the ability to localize relevant anatomical features and context (e.g., diaphragm, airways, carina, lungs, patient midline, and so forth); the ability to localize other relevant devices that may be potentially confounding with enteric tubes (e.g., probes, peripherally inserted central catheter (PICC) lines, electrocardiogram (ECG) leads or lines, endotracheal (ET) tube, and so forth); the ability to assess the tube position and to provide explanation or commentary about the assessment (e.g., explaining specific problems with current tube placement, such as "the side port location is too high relative to the diaphragm"); the ability to assess the tube position and to provide explanation or commentary regarding aspects of the placement verified to be correct or satisfactory (e.g., that the tube correctly bisects the diaphragm near the midline); the ability to provide automated measurements that are relevant for the tube assessment (e.g. the length of the tube below the diaphragm, the distance of the side port from the diaphragm, the measured tube diameter, etc.); the ability to show the detected tubes, the tube features, and relevant anatomical features and measurements in a graphical summary and the ability to highlight potentially problematic (or non-problematic) areas within the graphical summary); the ability to perform triage based on the tube placement classification, allowing prioritization of attention to potentially misplaced tubes; the ability to save the graphical summary in various formats (secondary capture, structure report, Integrating the Healthcare Enterprise (IHE) AI Results (AIR), and so forth); and the ability to allow the user to edit, modify, and/or annotate the graphical summary.

It may be noted that the present techniques, as applied to enteric tubes, may address additional complexity as compared to approaches that relate primarily to endotracheal tubes or other medical tubes. By way of example, the present techniques as applied to enteric tubes must address or allow for the acquisition and use of both chest and abdominal images (as opposed to only chest images). Further, enteric tubes have a variety of tube types which must be taken into account. By way of example, nasogastric tubes encompass standard nasogastric tubes (e.g., Levin tubes, Ryle's tubes), Salem sump tubes, small-bore silicone rubber feeding tubes (e.g., Keofeed tubes, Duo-tubes, Dobbhoff tubes), and other special purpose tubes (e.g., Ewald tubes, Cantor tubes, Miller-Abbott tubes, Sengstaken-Blakemore tubes, Minnesota tubes, Linton-Nachlas tubes, Nutrivent tubes). In addition, enteric tubes, unlike endotracheal tubes, may form loops and complex curves when inserted and may allow for many potential trajectories. Correspondingly, enteric tubes may have many placement requirements (relative to other medical tube insertions) and may be subject to many and varied types of misplacement. Due to their length, certain types of enteric tubes may also exit and/or re-enter the acquired images, posing a further distinct complexity to be addressed.

Figure 12:
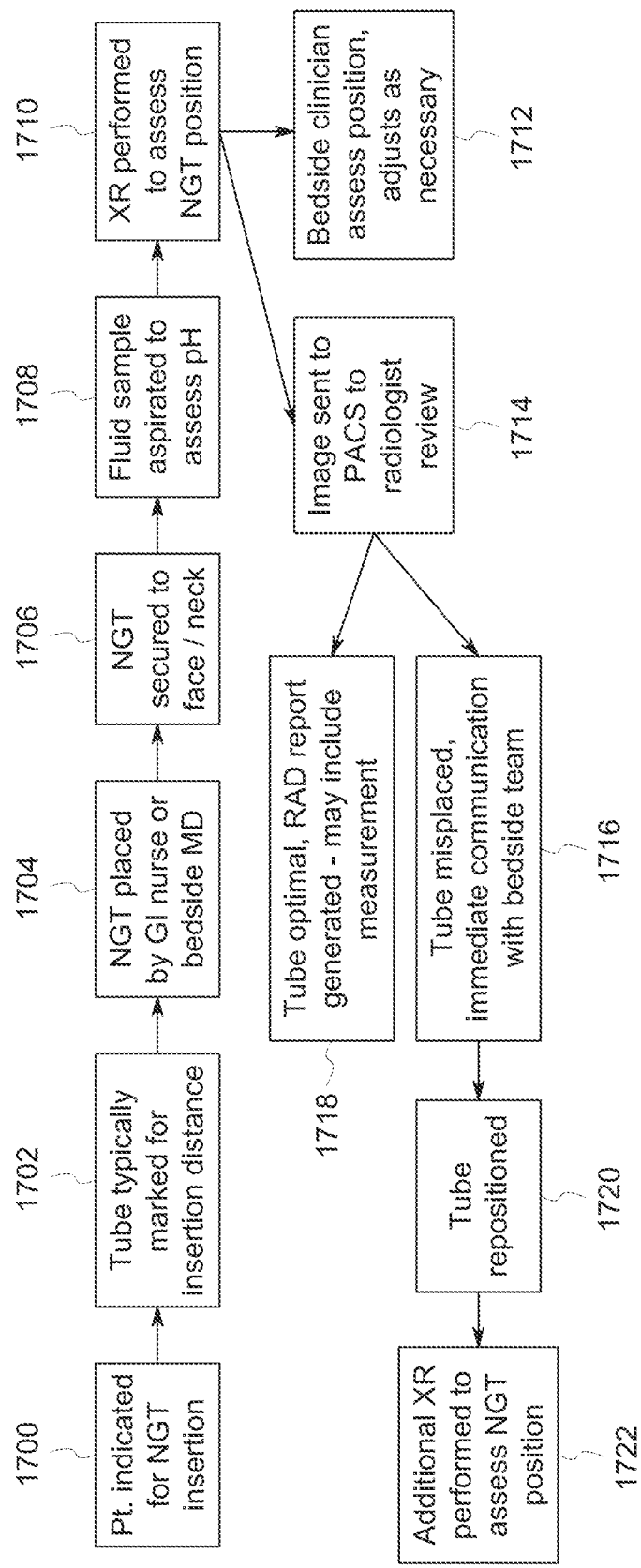
FIG. 12 is an example of a process flow of steps taken in the placement and assessment of a nasogastric tube.

By way of context, a high level workflow for an enteric tube (here a nasogastric tube (NGT)) placement is illustrated in FIG. 12. In this example, at step 1700 a point (e.g., an anatomical point) is indicated for insertion of the nasogastric tube. The nasogastric tube may then be marked for the appropriate insertion distance (step 1702). The nasogastric tube may then be inserted or otherwise placed (step 1704) by medical personnel, such as a gastrointestinal nurse or bedside doctor. Once inserted, the nasogastric tube may be secured (step 1706) to the face and/or neck of the patient. To verify placement in the stomach, a fluid sample may be aspirated and tested for pH (step 1708). An X-ray imaging operation may be performed (step 1710) to assess positioning of the nasogastric tube. The X-ray image data may be assessed and/or presented in accordance with the techniques discussed herein. The outputs of the analysis of the X-ray image data, as shown in FIG. 12 may be provided to the bedsides clinician(s) (step 1712) to assess the position of the nasogastric tube and to make any needed adjustments.

The outputs of the analysis of the X-ray image data, as shown in FIG. 12 may, in addition or in the alterative, be provided (step 1714) to a pictures archiving systems (PACS)

for review by a radiologist. In the depicted example, two outcomes are illustrated with respect to radiologist review. In the first (step 1718), the tube placement is determined to be optimal or satisfactory and a radiologist report is generated to this effect, which may measurement data. In the second (step 1716), the tube is determined to be misplaced and this information is communicated to the bedside team. The tube may then be repositioned (step 1720) by the bedside team and additional X-rays acquired (step 1722) to assess tube placement. Benefits of utilizing the techniques as discussed herein with respect to this workflow include, but are not limited to: providing increased confidence in tube placement, providing alerts as to misplaced tubes and/or suboptimal image quality, prioritizing cases of suspected tube misplacement, providing automated measurements that might not otherwise be generated, and speeding up report creation. Thus, as described herein, the presently described technique helps detect the presence and /or number of enteric tubes, helps determine if the enteric tube is malpositioned, provides an immediate bedside alert for malpositioned tubes, provides PACS prioritization for suspected malpositioned tubes, and provides visualization of the tube and anatomical context and features. In terms of clinical benefits, these may include immediate bedside intervention in critical cases based on the decision of the bedside clinician, faster intervention in critical cases based on the radiology report, and higher confidence for the bedside team for appropriately placed tubes.

Figure 13:
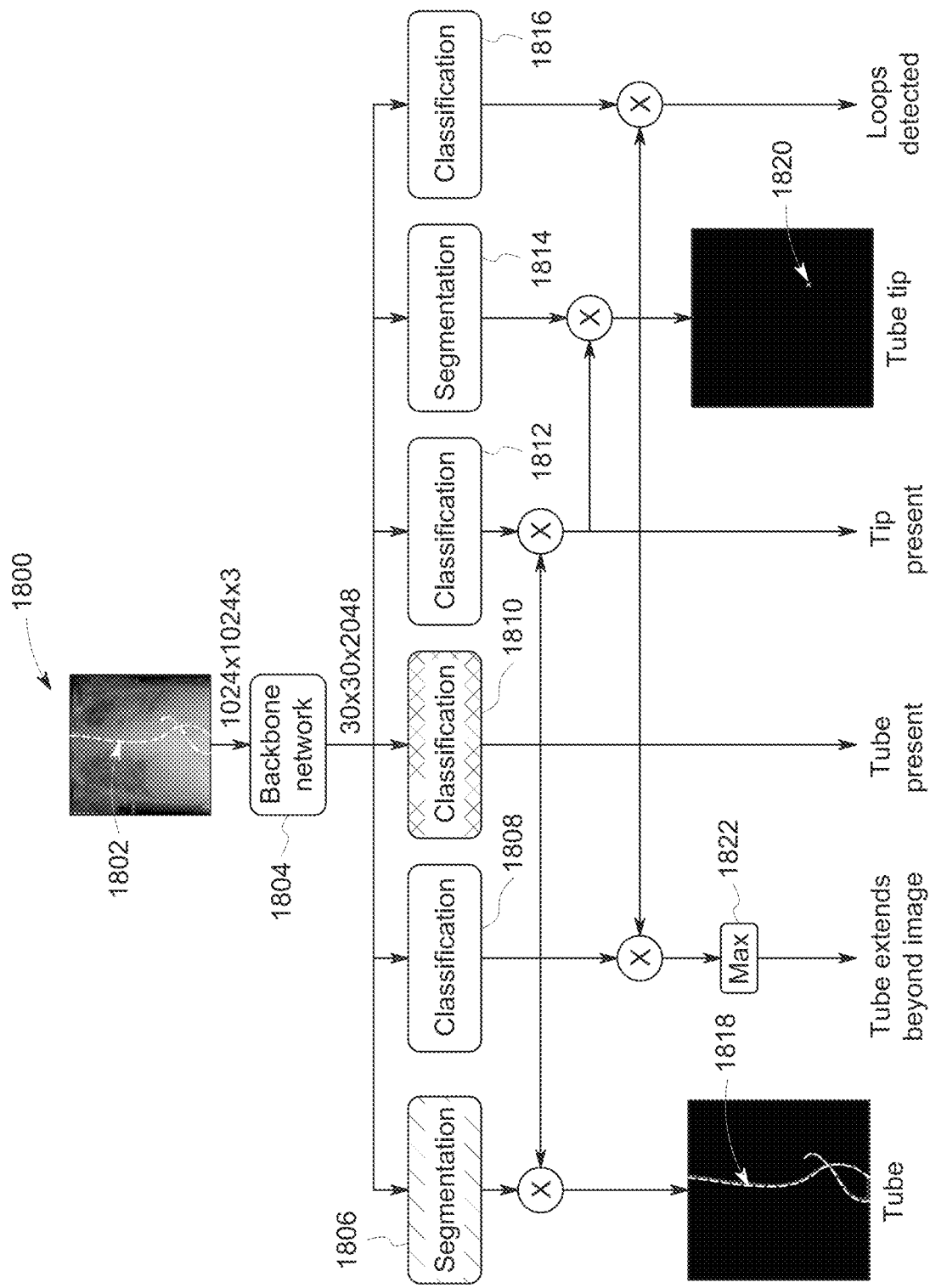
FIG. 13 depicts a model architecture for segmenting and classifying an enteric tube placement.

Turning to FIG. 13, a brief overview of a model architecture for segmenting and classifying an enteric tube (e.g., a nasogastric tube). In this example, an image 1800 or sequence of images of the anatomic region of interest (e.g., chest and abdomen) is acquire and provided to a backbone network 1804. In the depicted example, the image(s) 1800 include an enteric tube 1802 as part of the image. Image data and operations are shown as being performed in the context of the network 1804. A segmentation operation 1806 may be performed to identify and segment the tube 1802 within each image 1800 so as to generate a segmented object or representation 1818 of the tube 1802.

Classification logic (such as AI-based classification operations) may operate on the segmented representation 1818 to generate a series of classification outputs. By way of example, classification logic 1800 may make an initial determination as to whether a tube 1802 is present in the image 1800 based on the provided inputs. In addition, assuming a tube 1802 is determined to be present, further classification logic 1812 and segmentation logic 1814 may be performed to determine if a tube tip is present and, correspondingly, to localize and segment the tube tip 1820 within the image(s) 1800. Further classification logic 1808 may determine, based upon the segmented representation and in combination with a specified maximum value or threshold 1822, whether the tube 1802 extends beyond the image 1800. Classification logic 1816 may also be applied to detect whether loops are present in the tube 1802 based upon the segmented representation 1818. In view of this architecture, each image or sequence of images 1800 may be processed as described herein to provide information to the bedside clinicians and/or to radiologists viewing the images and outputs via PACS.

As discussed herein, outputs of the AI-based logic may be used to assess or otherwise evaluate placement of an enteric tube. For example, outputs of the AI-based logic may be utilized to characterize a placement as expected or satisfactory (e.g., side port okay, no side port long, tip outside long), as having a loop or kink (e.g., loop then down, kink, too deep), as being borderline (e.g., tip outside short, sideport borderline, tube length borderline), as being malpositioned so as to pose an airways risk (e.g., above carina, in airways), as being malpositioned so as to be too high (e.g., in esophagus, no side port short, side port high), as being malpositioned so as to be high with loops (e.g., loop above diaphragm, returns to esophagus), or as having a limited field-of-view or otherwise out-of-scope (e.g., tip outside short, below diaphragm short, below diaphragm exit up). In practice, and with the preceding in mind, there may be a number of varied and suitable options for grouping the potential tube positions into possible classification outputs for a given implementation including, but not limited to: (1) malpositioned tube present/no malpositioned tube present, (2) no tube present/correctly placed tube/malpositioned tube, (3) no tube present/correctly placed tube/tube position needs verification, (4) no tube present/correctly placed tube/malpositioned tube/borderline placement/partially visualized tube/loops or kinks present/out of scope due to limited field of view, (5) no tube present/correctly placed tube/correctly placed tube with side port/malpositioned tube in airways/malpositioned tube in esophagus/malpositioned tube too high/borderline placement/loops or kinks present/partially visualized tube/uncertain/out of scope due to limited field of view/and so forth.

Figure 14:
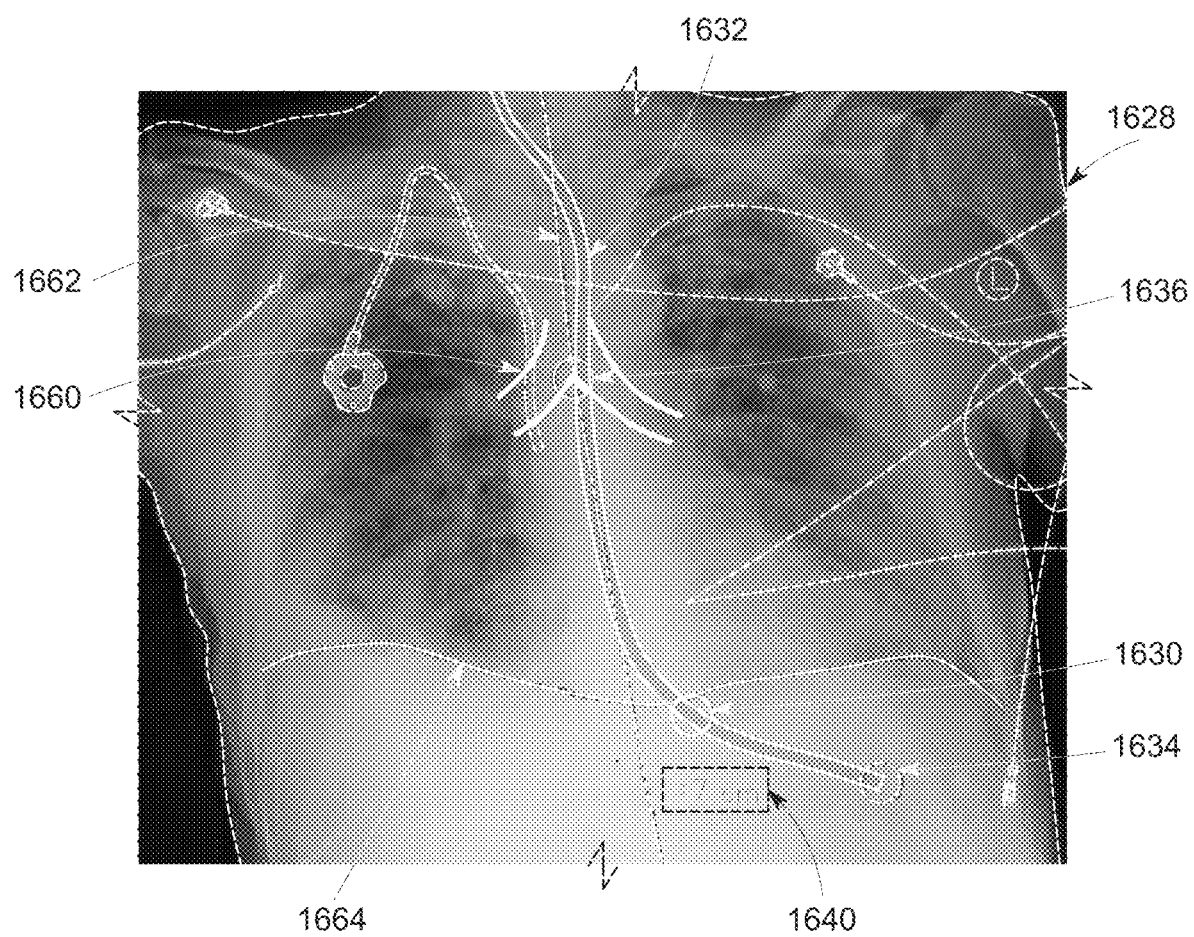
FIG. 14 is an example of a combined image identifying a tube or line within a patient.
Figure 15:
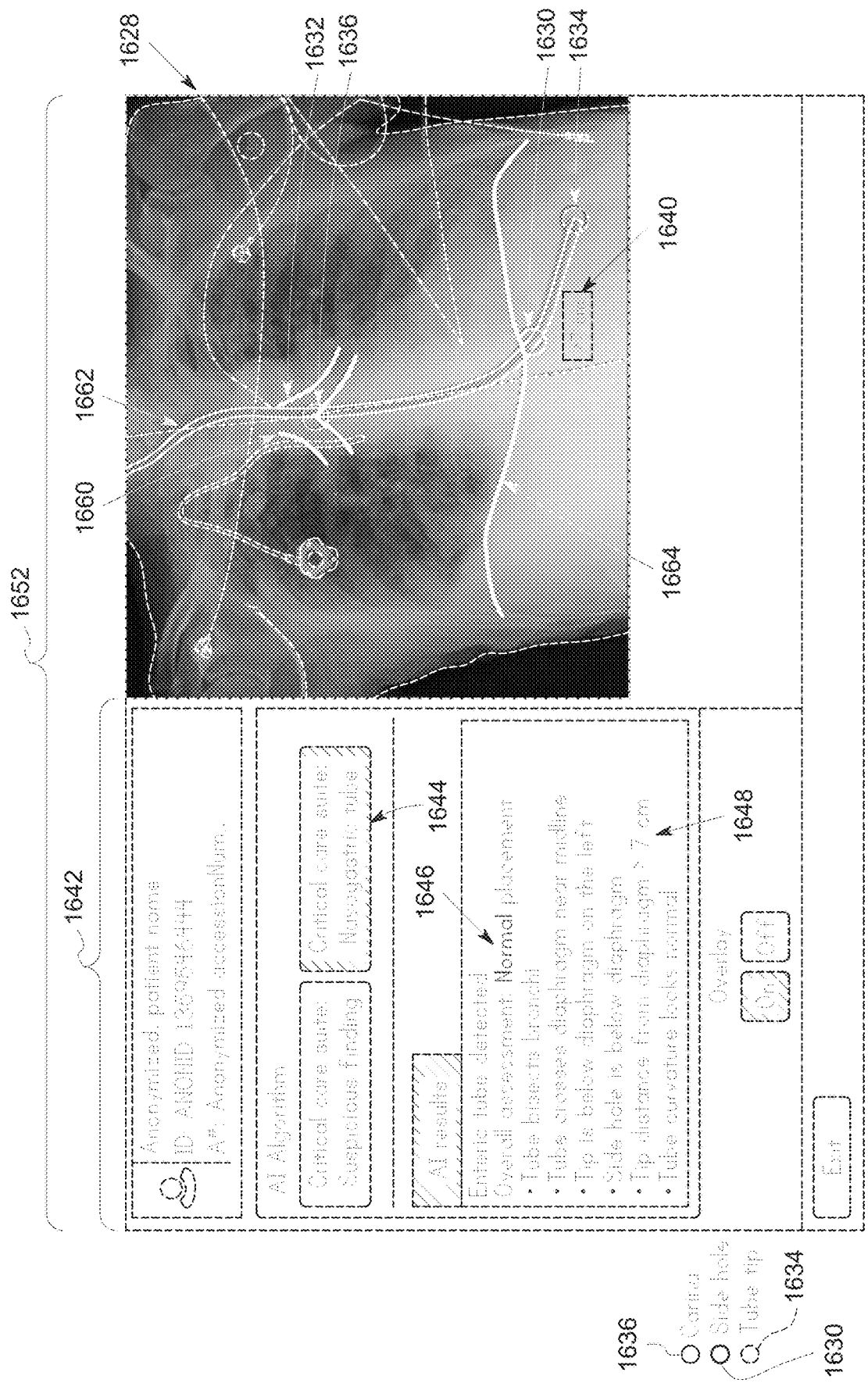
FIG. 15 is a schematic diagram of a user interface having a combined image identifying a tube or line within a patient.

With regard to the presented or displayed information, and turning to FIGS. 14 and 15, an example of a combined image 1628 (e.g., DICOM image) identifying an enteric tube or line within a patient that may be displayed on a display. As depicted, the combined image 1628 of a patient shows a nasogastric tube 1632 positioned within the patient. As part of the combined image, one or more anatomical references or features may be indicated via overlay of dashed lines or other visual references to facilitate user visualization of the tube 1632 relative to the anatomic context. By way of example, in the depicted image dashed line 1660 is overlaid to illustrate the bronchi, dashed line 1662 is overlaid to illustrate the patient midline, and dashed line 1664 is overlaid to illustrate the diaphragm.

In the depicted example, a graphical marker 1634 (e.g., circle or color-coded circle) overlaid on the combined image 1628 indicates the location of the end (i.e., tube tip) of the nasogastric tube 1632. A graphical marker 1636 (e.g., circle or color-coded circle) overlaid on the chest image indicates a reference or anatomical location (e.g., carina). A graphical marker 1630 (e.g., circle, color-coded circle, dashed circle, and so forth) overlaid on the image indicates a side hole or side port, if present, of the nasogastric tube 1632. A numerical value 1640 indicates a measured distance (e.g., a tube length distance) between the tip of the nasogastric tube 1632 and a reference or anatomical location, here the diaphragm. In certain embodiments, a confidence metric in the measured distance generated by the artificial intelligence is also displayed (e.g., as depicted a confidence level). In certain embodiments, the tube 1632, the graphical markers 1630, 1634, and/or 1636 may be color coded (e.g., blue, yellow, green, and red) or otherwise visually coded (e.g., solid line, dashed line, double lines, lines of distinctive thickness).

FIG. 15 is a schematic diagram of a user interface 1652 having a combined image 1628 identifying a tube or line within a patient that may be displayed on a display. As shown in FIG. 15, the combined image 1628 may also include or be displayed alongside a header or other information block or section 1642 that includes information related to the image 1628. For example, as depicted, the information block 1642 (a portion of which is expanded as an inset to improve visibility) includes the type of tube or line 1644 (e.g., a nasogastric tube), whether the placement of the tube is proper or not 1646, and the calculated distance 1648 between the tip of the tube and the reference or anatomical marker.

In certain embodiments, the information block 1642 may include an indication as to whether the tube or line was detected, such as by the AI-based logic discussed herein. In certain embodiments, one or more confidence metrics may be displayed on the image 1628 (e.g., for the calculated distance, for the determination of the presence of the medically placed tube or line, for an accuracy in detecting the tip of the tube or line, and/or for an accuracy in detecting the reference or anatomical landmark). As shown in the example, in certain embodiments the information block may also include other relevant placement information determined by the AI-based logic. By way of example, in the depicted information block of FIG. 15 information about whether the tube 1632 bisect the bronchi, whether the tube crosses the diaphragm near midline, whether the tip is below the diaphragm on the left, whether the side hole is below the diaphragm, the tip distance from the diaphragm, and whether the tube curvature appears normal are all displayed. That is, in certain embodiments, the depicted indication may indicate whether the tube or line is placed properly, misplaced, provide an indication of what is wrong with the placement, or provide instructions for correcting the placement. An option to turn the image overlay on or off is also provided in the depicted example.

Figure 16:
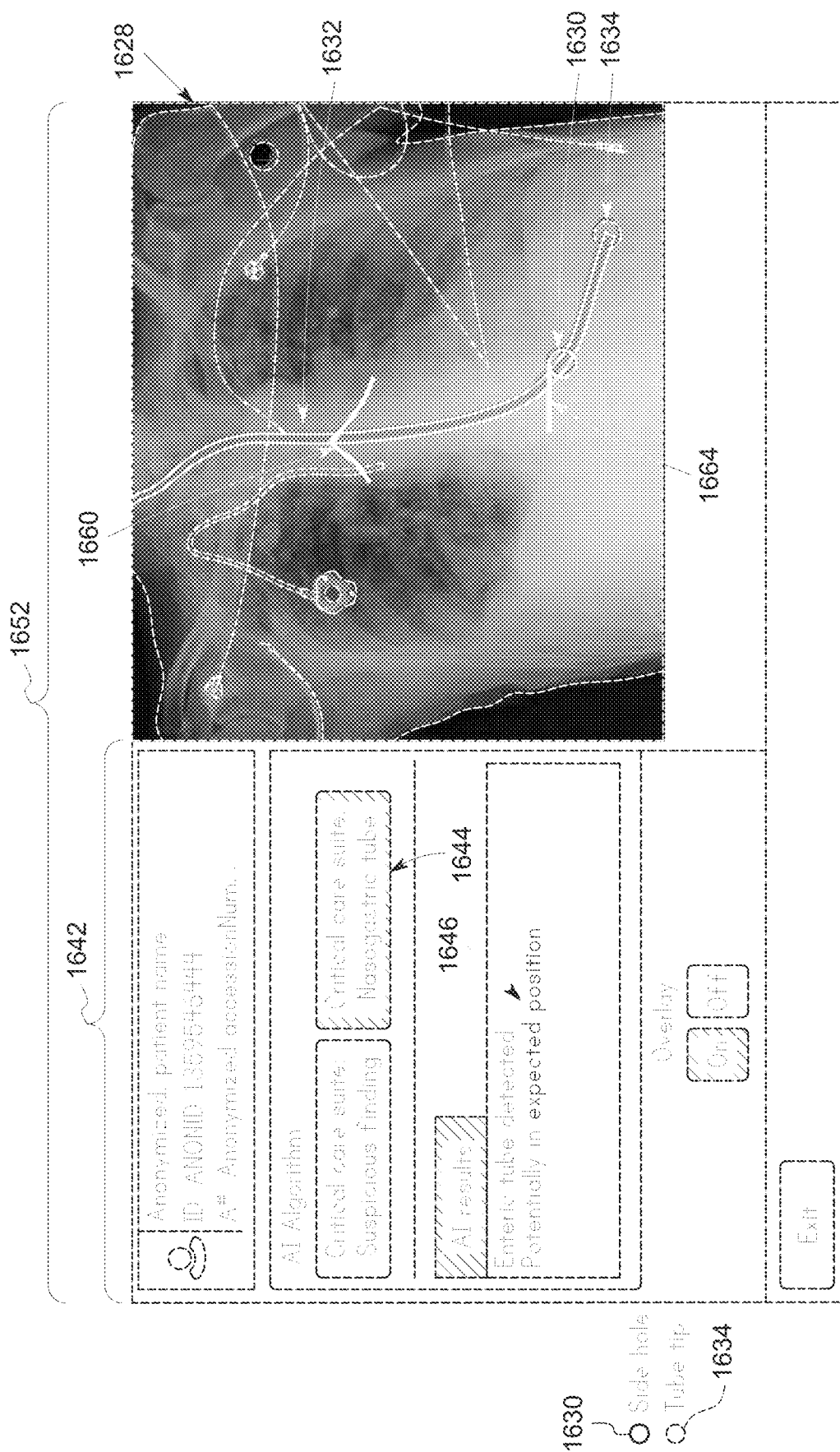
FIGS. 16-20 depict further schematic diagrams of a user interface having a combined image identifying a tube or line within a patient in a context where the tube is in an expected position.
Figure 17:
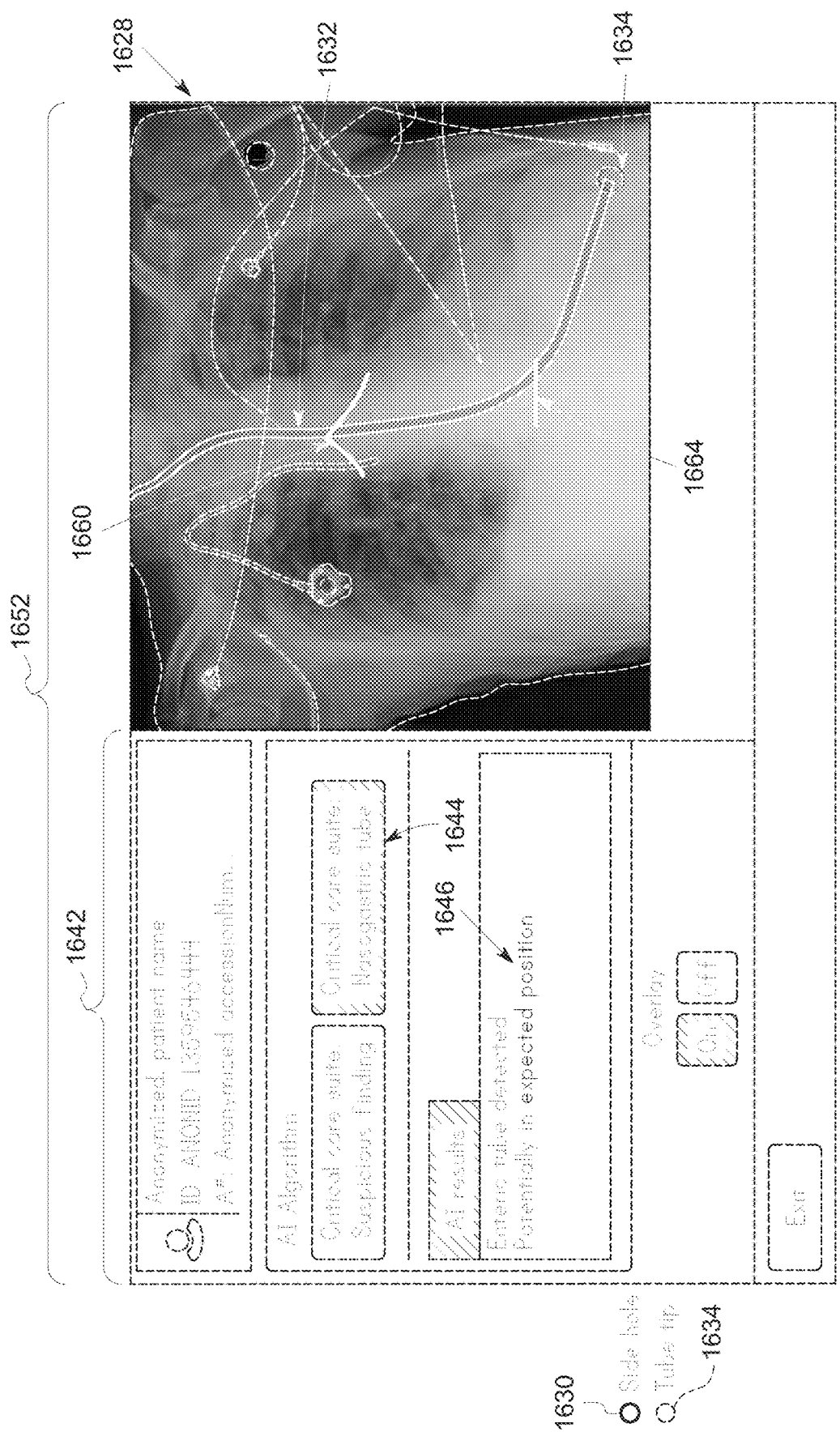
Figure 18:
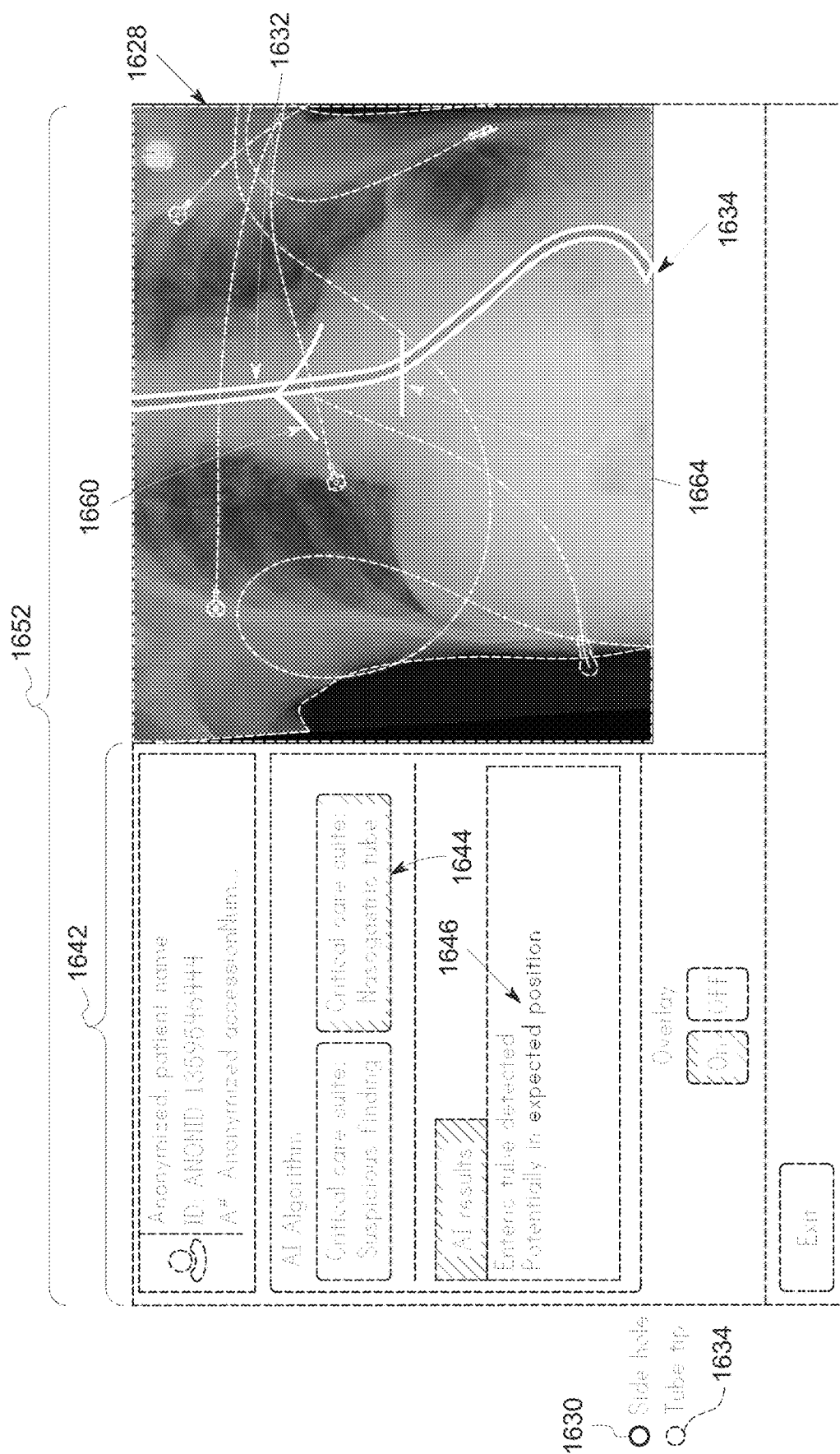
Figure 19:
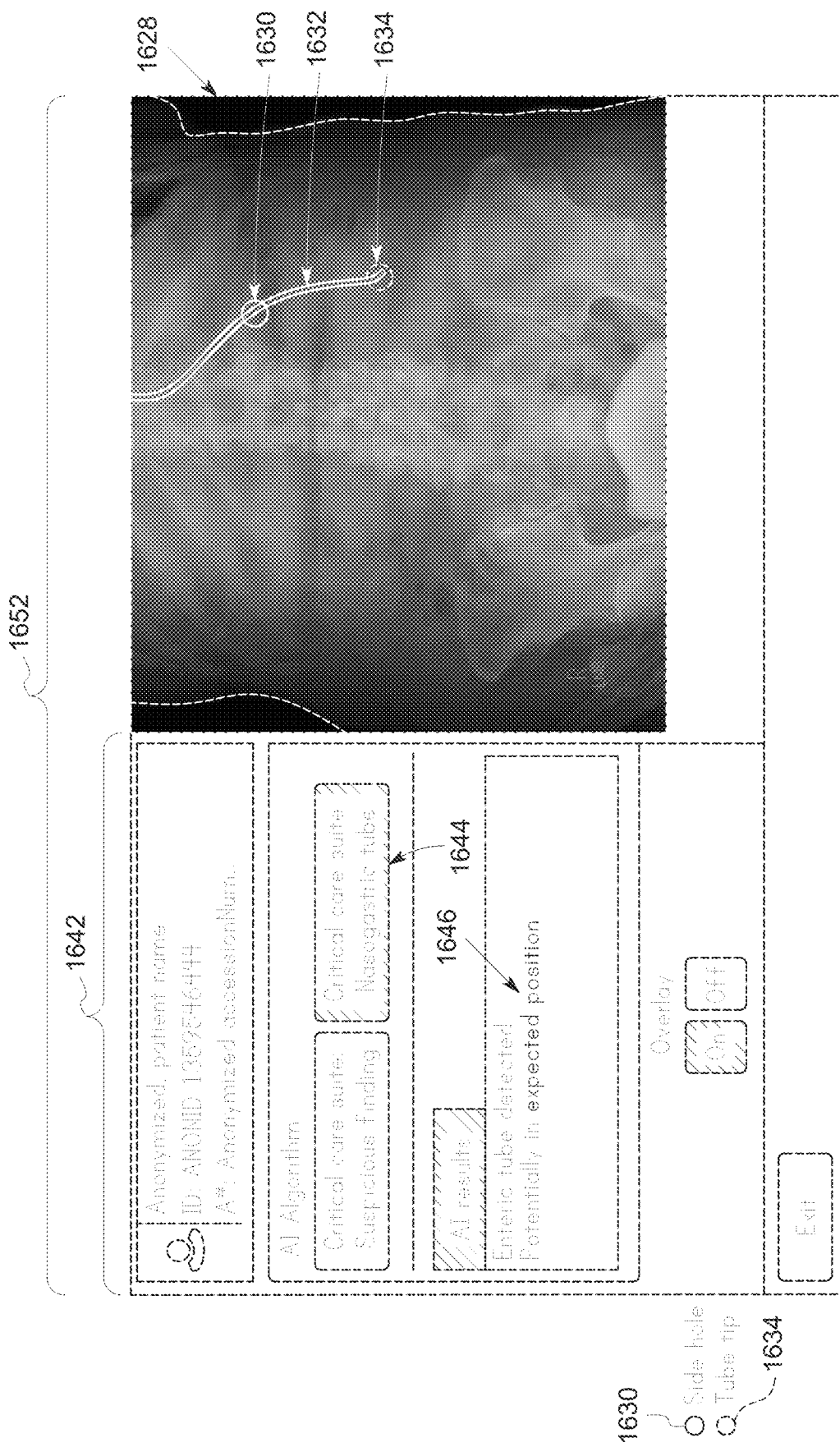
Figure 20:
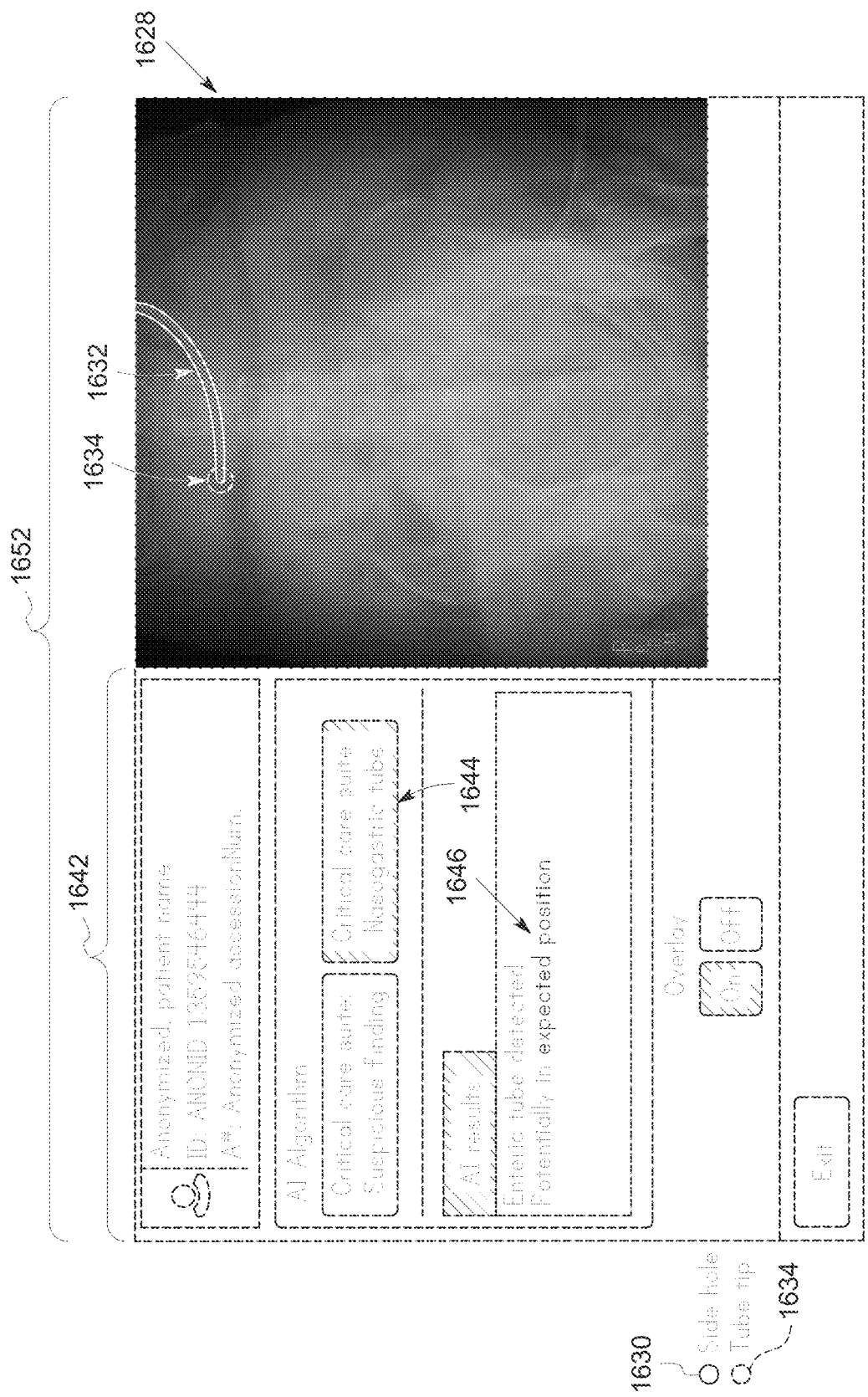

By way of providing further examples, additional user interfaces 1652 are described below that illustrate different tube placements and AI outcomes and how such placements and outcomes might be presented to a user. By way of example, and turning to FIG. 16, an example is displayed of results and visualization provided for a normal or expected tube placement with a side port present. FIG. 17 depicts an example of results and visualization for a normal or expected tube placement where no side port is present and with a long placement with respect to the tip extending beyond the diaphragm. FIG. 18 depicts an example of results and visualization for a normal or expected tube placement where no side port is present and with a long placement where the tip is at the edge of or outside the image. FIG. 19 depicts an example of results and visualization for a normal or expected tube placement where the tube 1632 is in a long placement below the diaphragm. FIG. 20 depicts an example of results and visualization for a normal or expected tube placement where the tube 1632 is placed deep but only a short portion of the tube is visible.

Figure 21:
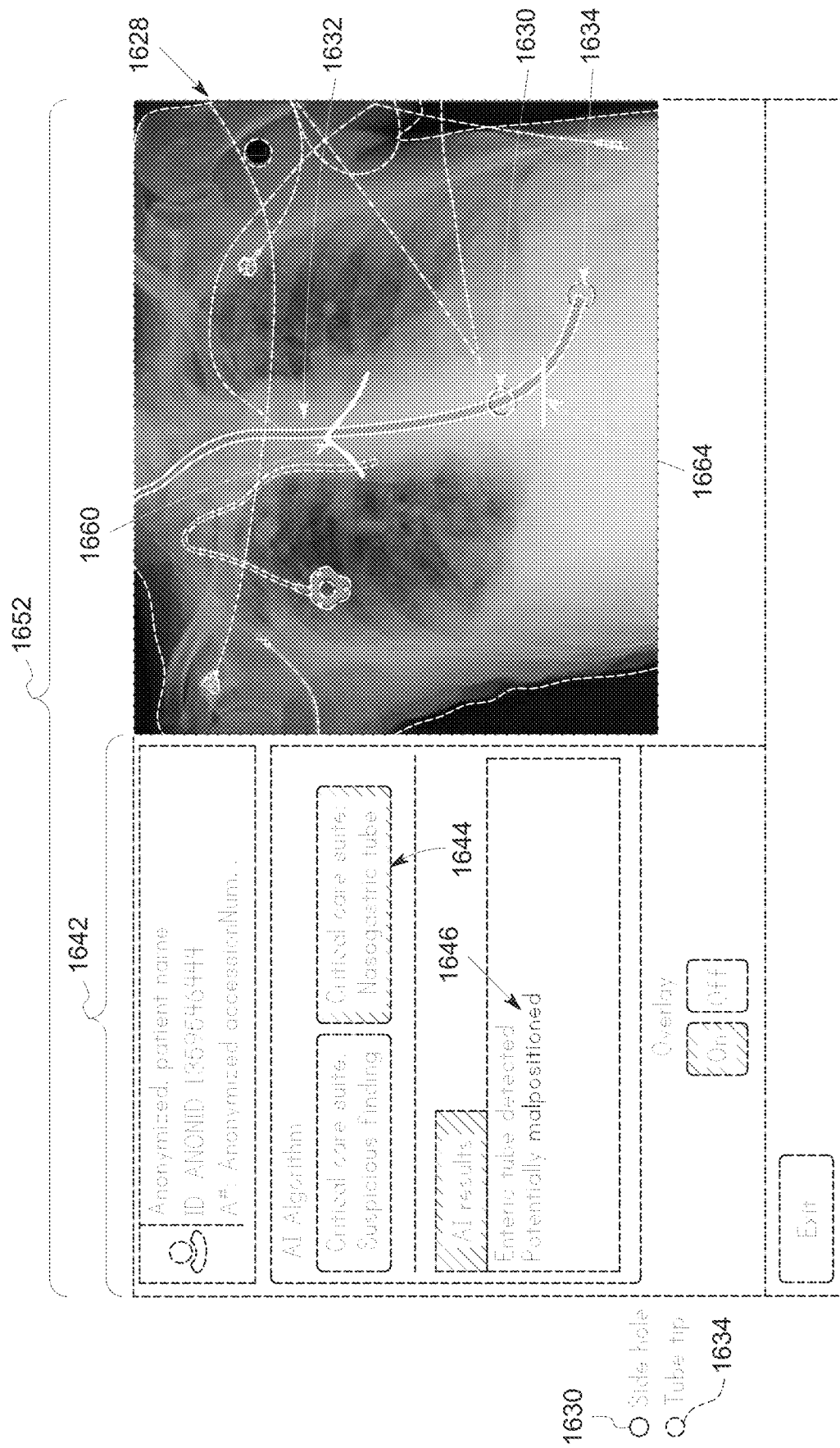
FIGS. 21-28 depict further schematic diagrams of a user interface having a combined image identifying a tube or line within a patient in a context where the tube is malpositioned.
Figure 22:
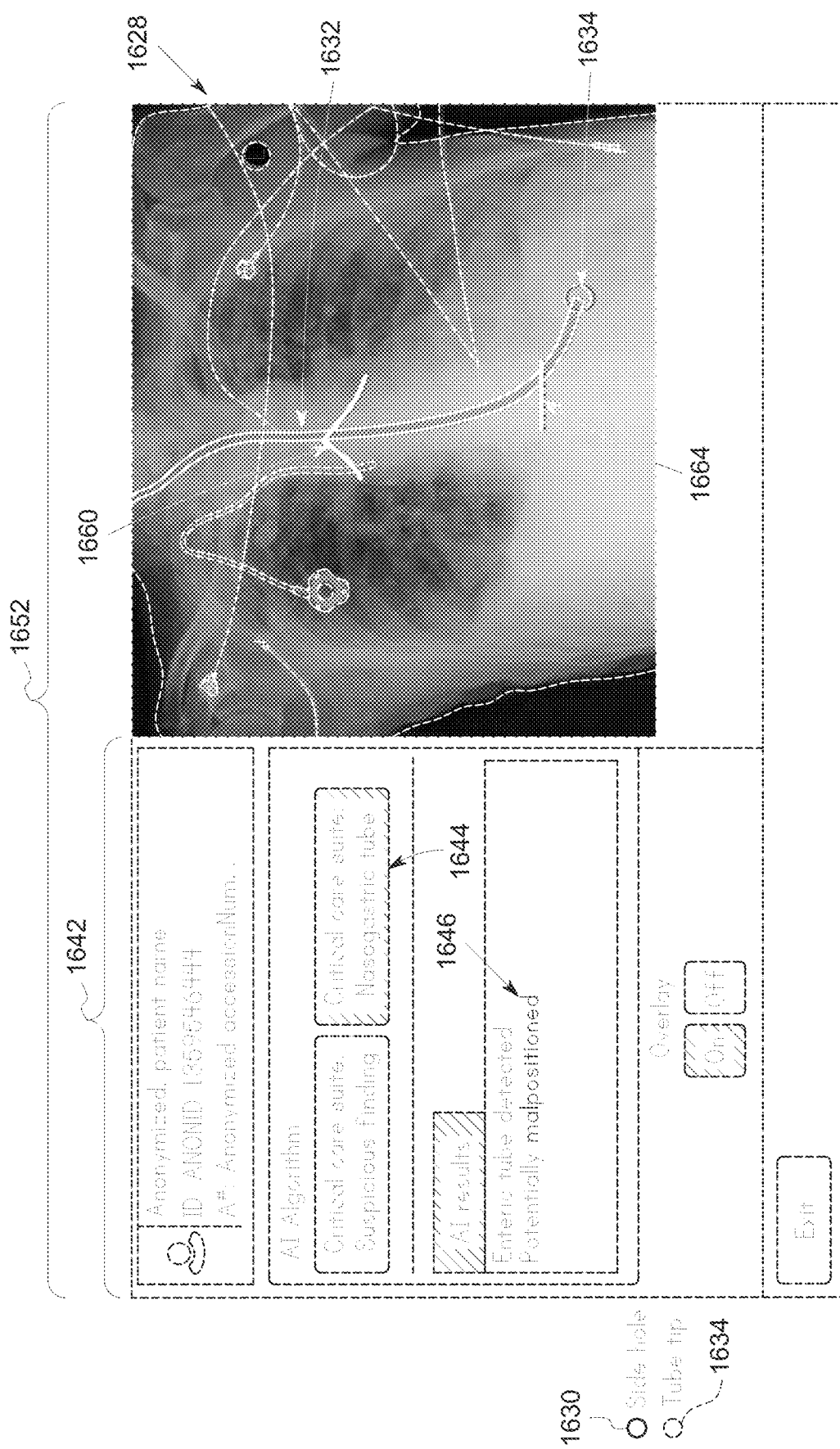
Figure 23:
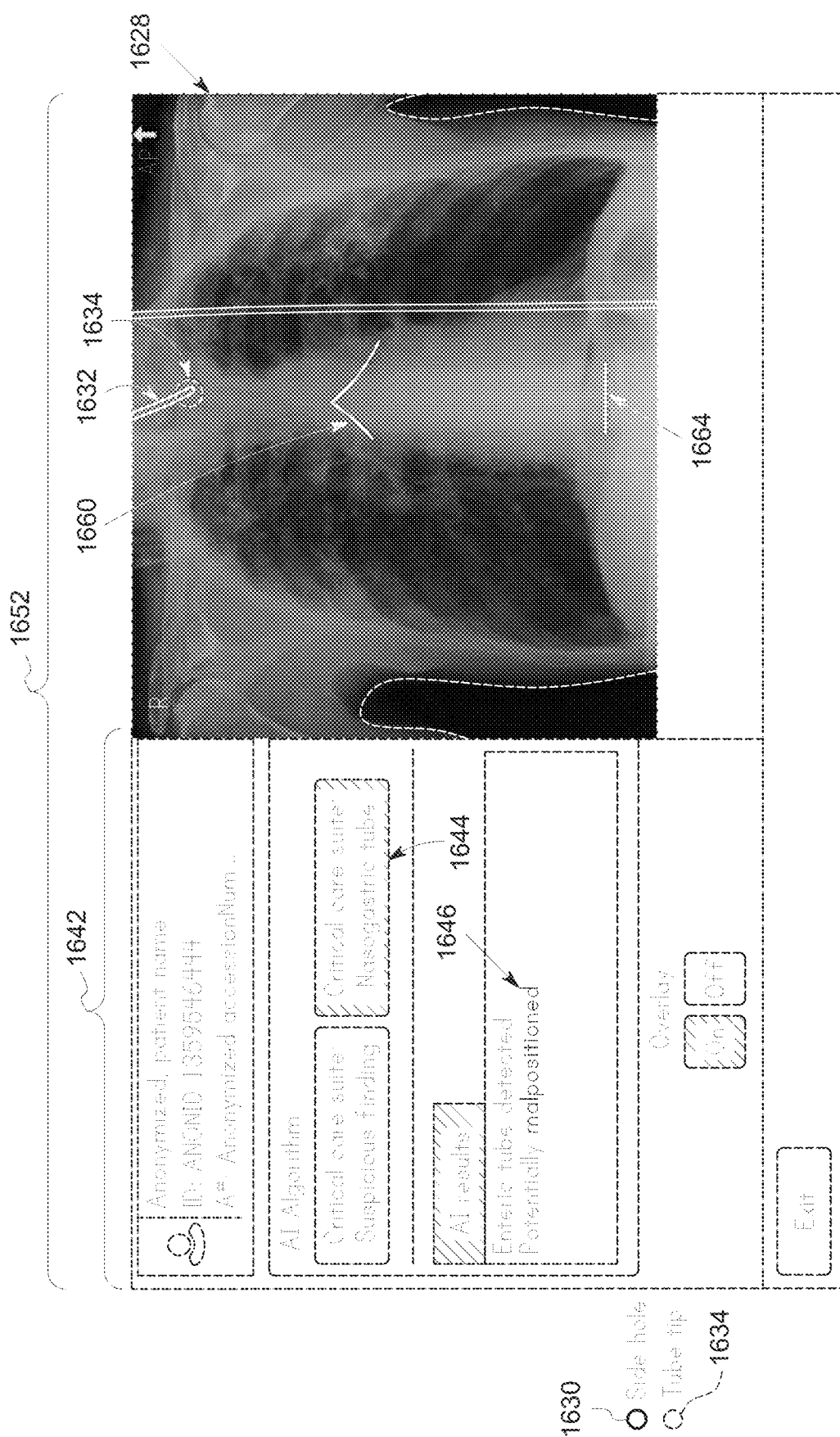
Figure 24:
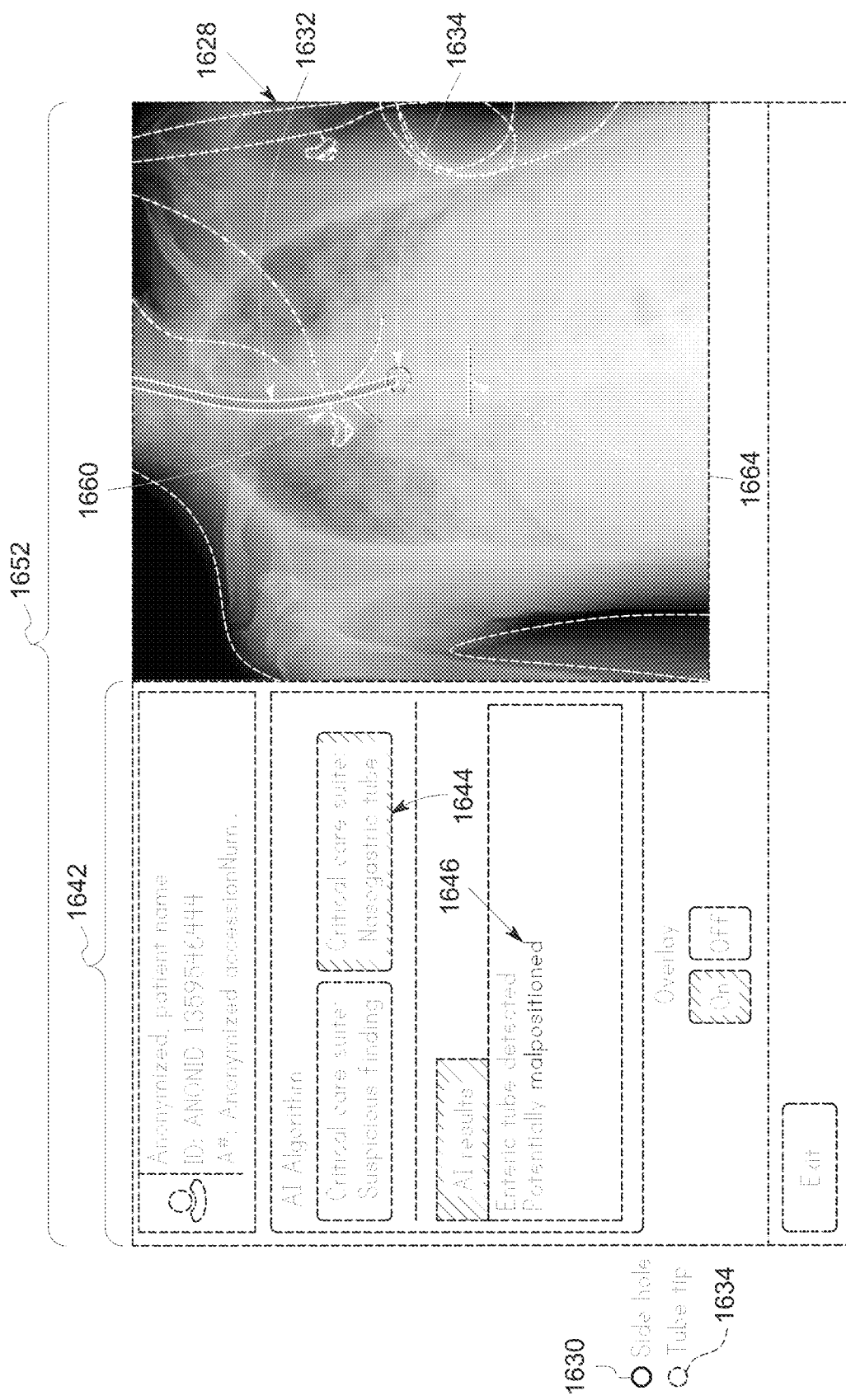
Figure 25:
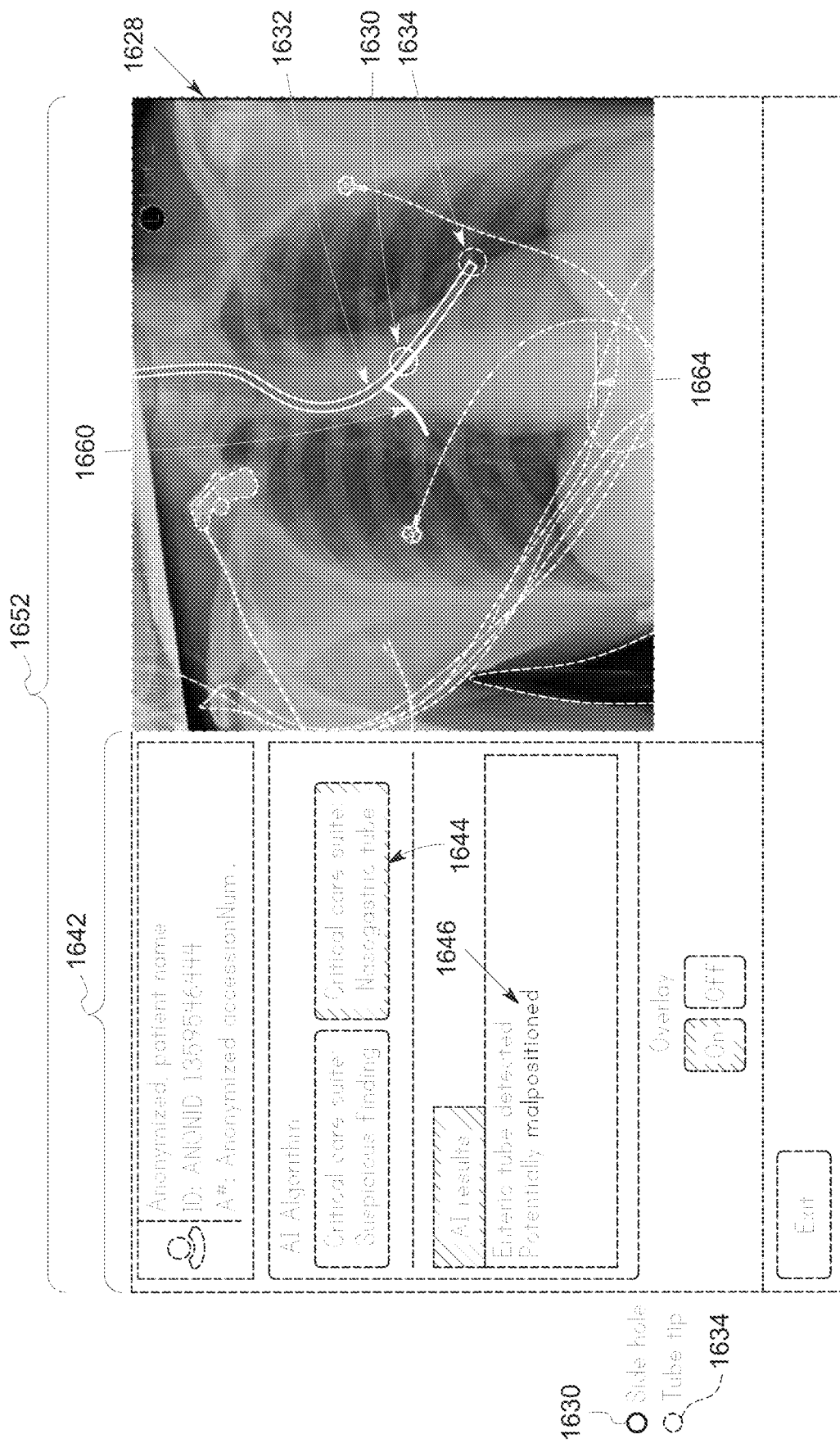
Figure 26:
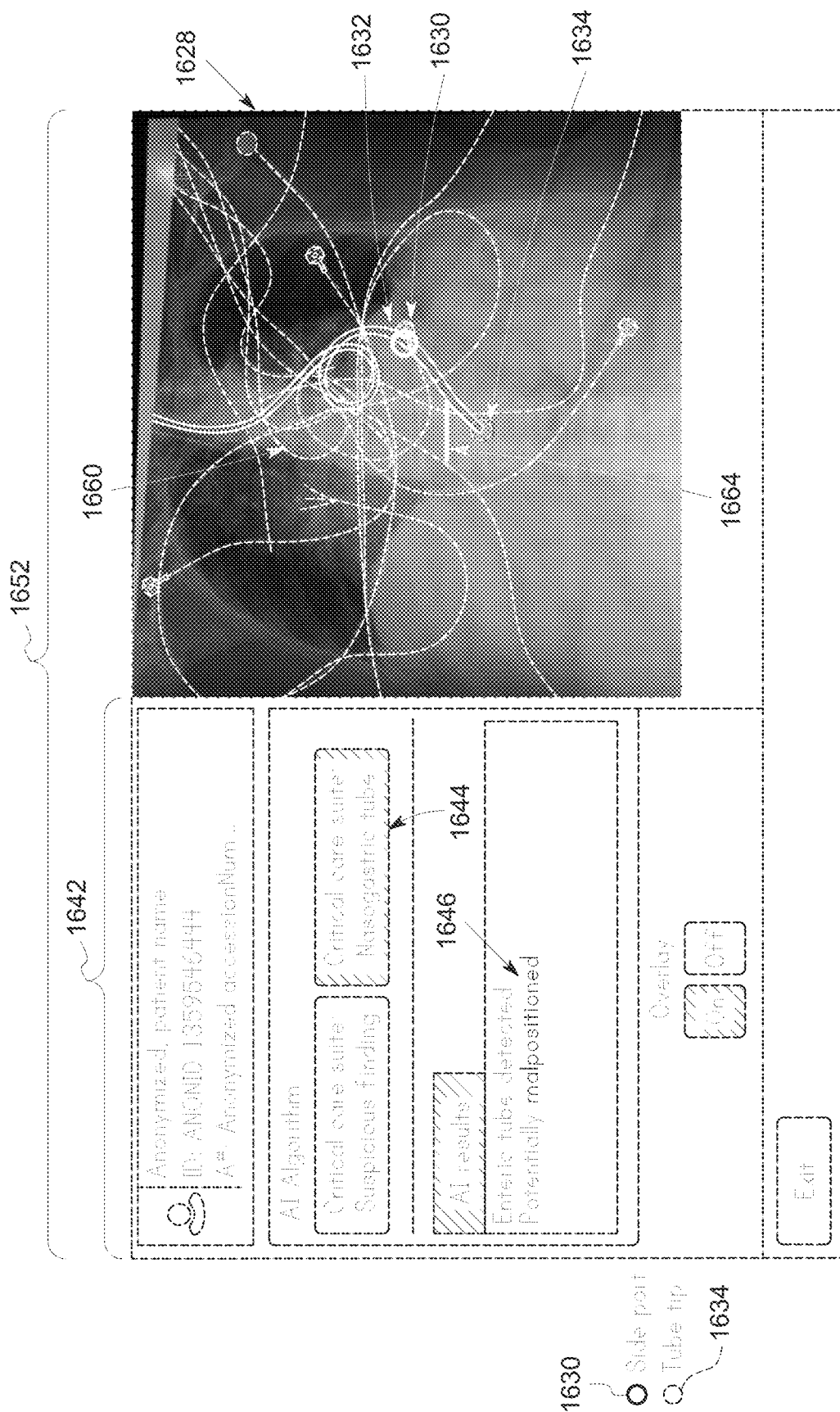
Figure 27:
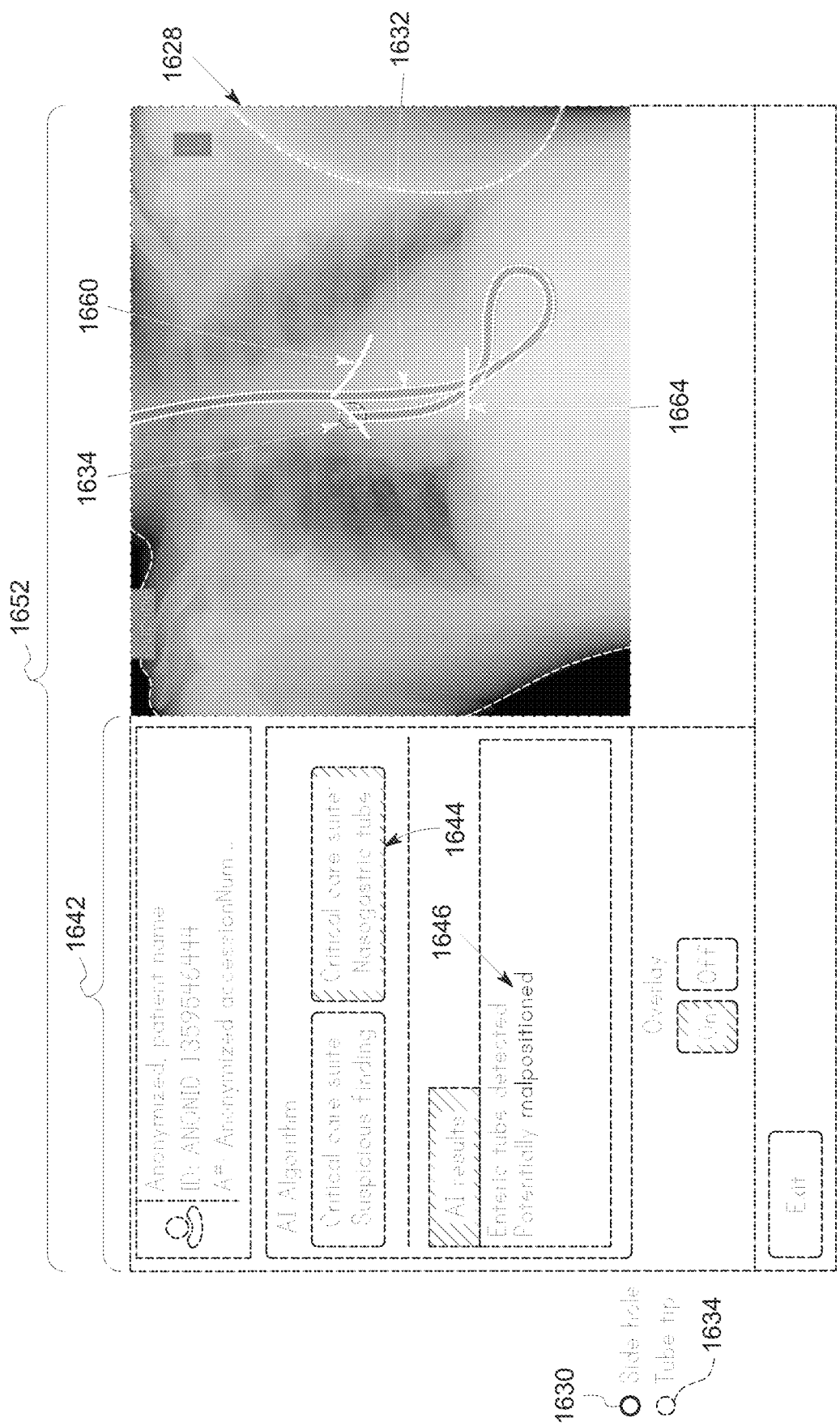
Figure 28:
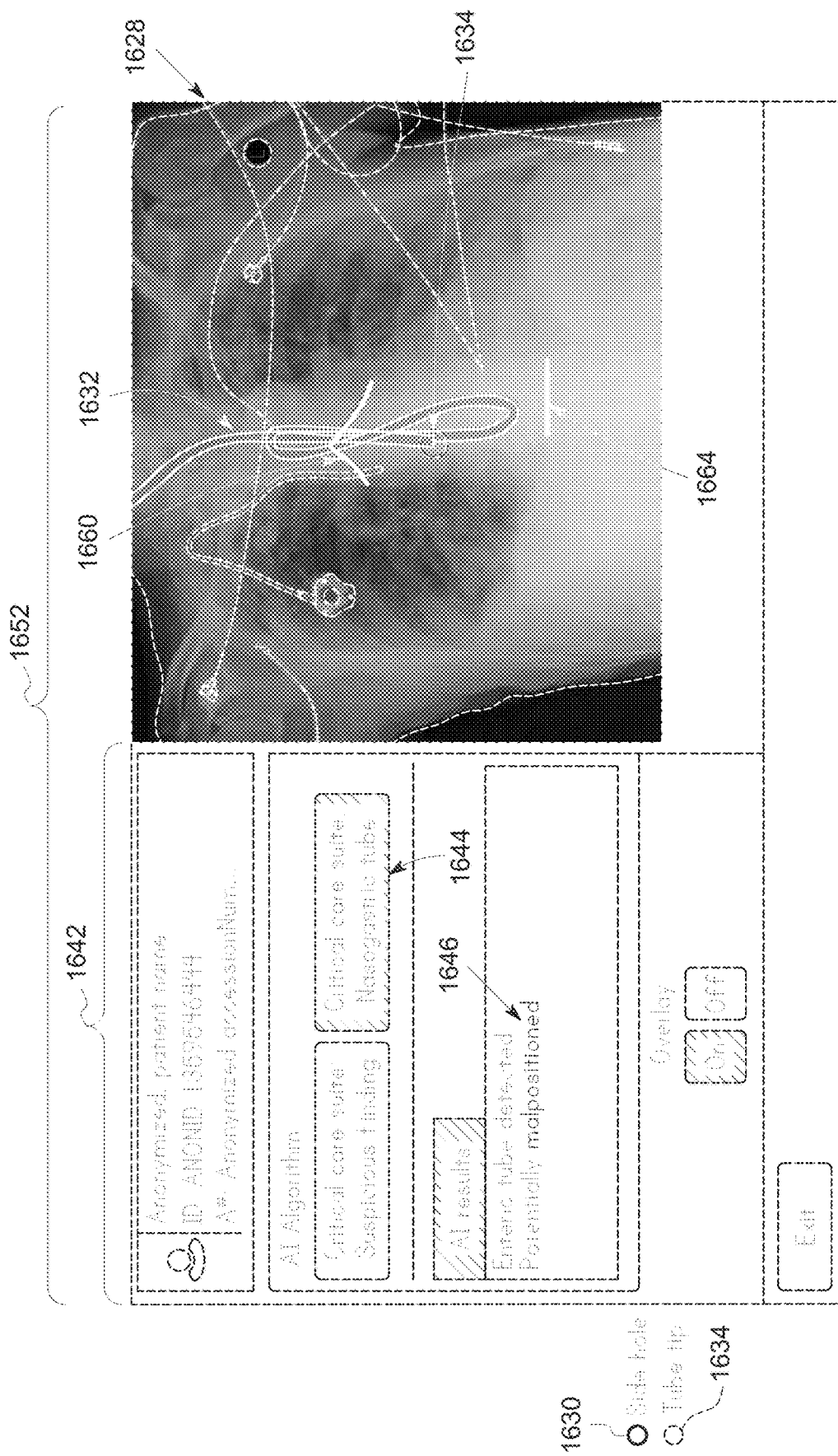

While the preceding examples illustrate expected or acceptable placements, the following examples illustrate malpositioned, borderline, or indeterminate tube placements. Turning to FIG. 21, an example is displayed of results and visualization provided for a malpositioned tube placement in which the side port is high (e.g., positioned above the diaphragm). To facilitate communication of the problematic aspect of the tube placement, one or both of the graphical marker 1630 corresponding to the side port and/or the graphical marker (e.g., dashed line) 1664 corresponding to the diaphragm may be color-coded (e.g., yellow or red). Similarly the text 1646 in the information block 1642 indicating whether the placement of the tube is proper or not may indicate that the tube is malpositioned. This text may also be color-coded (e.g., yellow or red) to indicate a problematic placement. Similarly, FIG. 22 depicts an example of results and visualization for a malpositioned tube placement where no side port is present and with a short placement with respect to the tip extending beyond the diaphragm. FIG. 23 depicts an example of results and visualization for a malpositioned tube placement where the tube tip is positioned above the carina. FIG. 24 depicts an example of results and visualization for a malpositioned tube placement where the tube 1632 is positioned within the esophagus. FIG. 25 depicts an example of results and visualization for a malpositioned tube placement where the tube 1632 is positioned within airways. FIG. 26 depicts an example of results and visualization for a malpositioned tube placement where the tube 1632 is positioned within the pleural cavity. FIG. 27 depicts an example of results and visualization for a malpositioned tube placement where the tube 1632 is positioned so as to return and re-ascend the esophagus. FIG. 28 depicts an example of results and visualization for a malpositioned tube placement where the tube 1632 is positioned so as to loop above the diaphragm.

Figure 29:
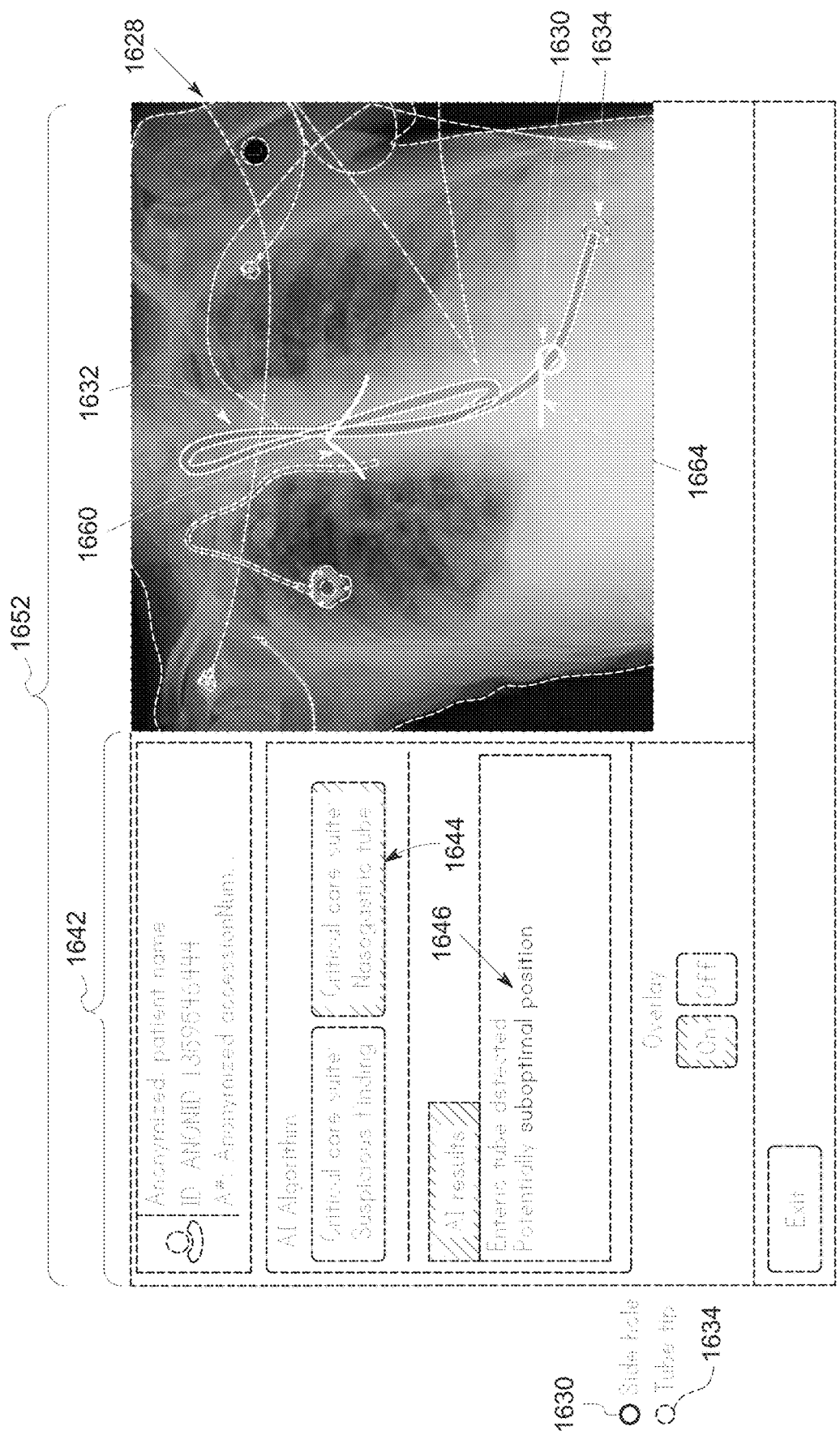
FIGS. 29-31 depict further schematic diagrams of a user interface having a combined image identifying a tube or line within a patient in a context where the tube is in a suboptimal position.
Figure 30:
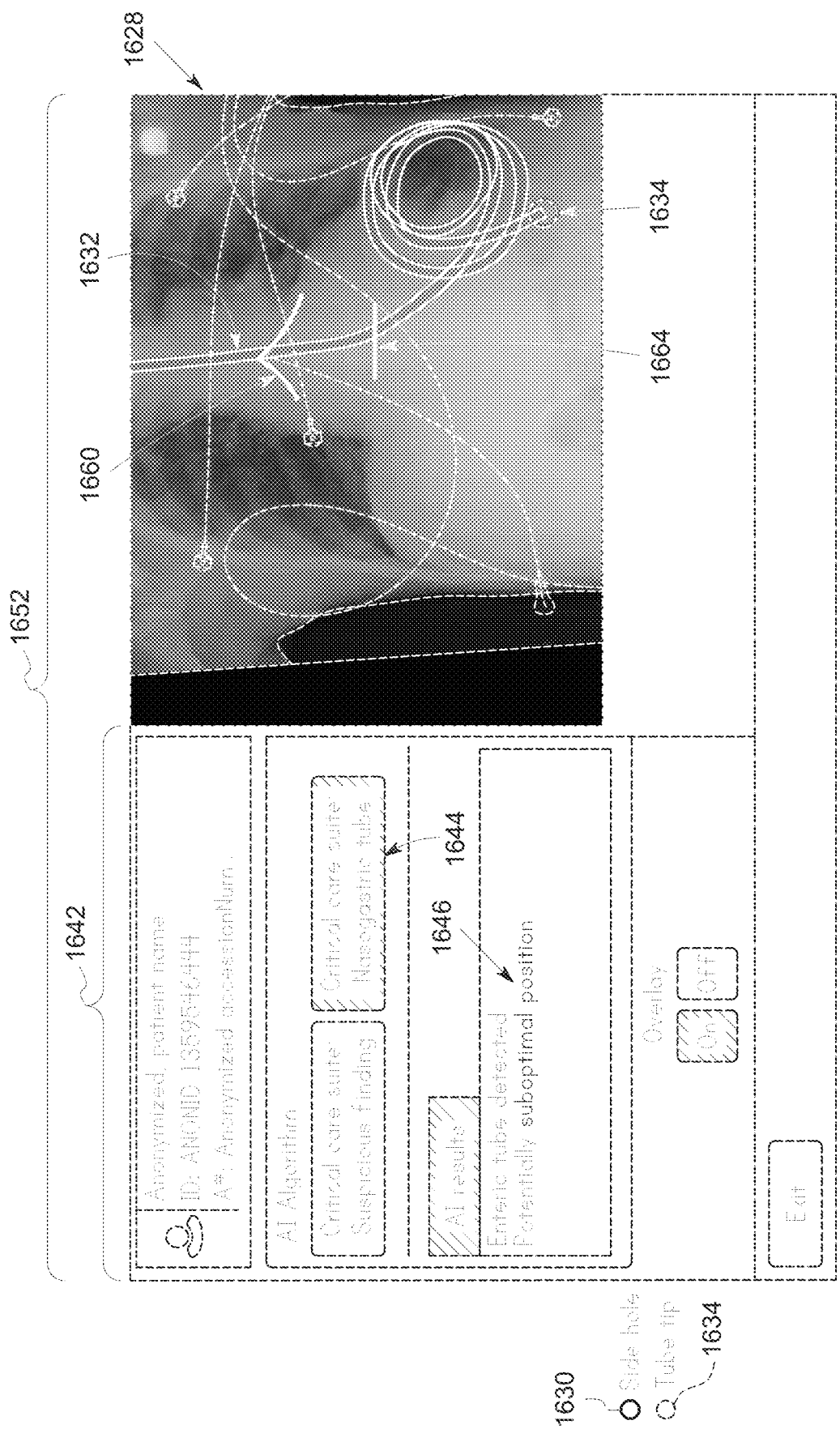
Figure 31:
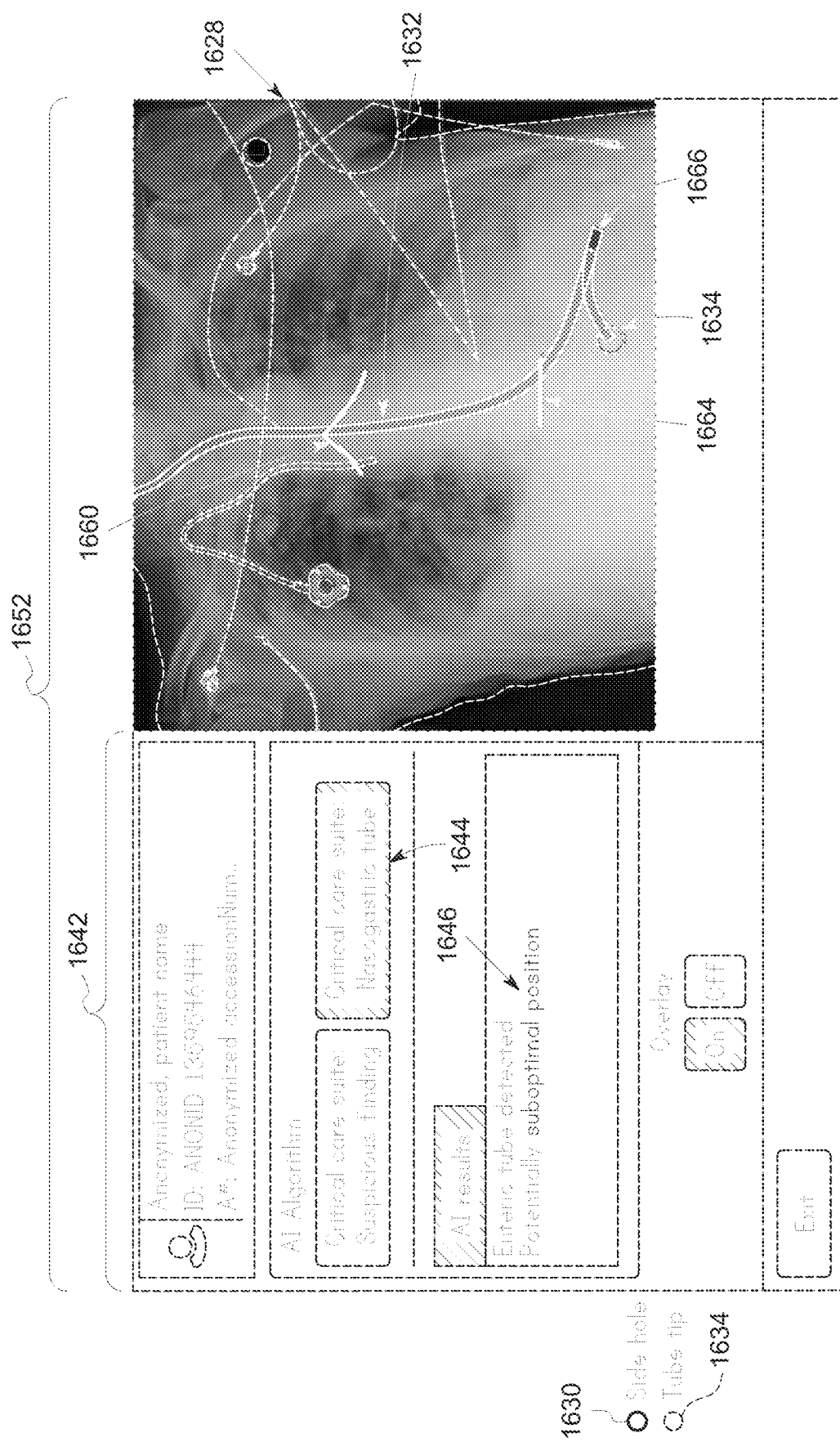

In the following examples, a suboptimal tube placement is illustrated in the context of the AI outputs and provided visualizations. Turning to FIG. 29, an example is displayed of results and visualization provided for one such suboptimal position in which a tube segment above the diaphragm loops, but the side port and tip placement is below the diaphragm. Similarly, FIG. 30 depicts an example of results and visualization for a suboptimal tube placement where a tube segment loops below the diaphragm and the overall tube placement is too deep. FIG. 31 depicts an example of results and visualization for a suboptimal tube placement where a tube segment loops is kinked below the diaphragm. To facilitate communication of the problematic aspect of the tube placement, the problematic segment 1666 of the tube 1632 may be color-coded (e.g., yellow or red).

Figure 32:
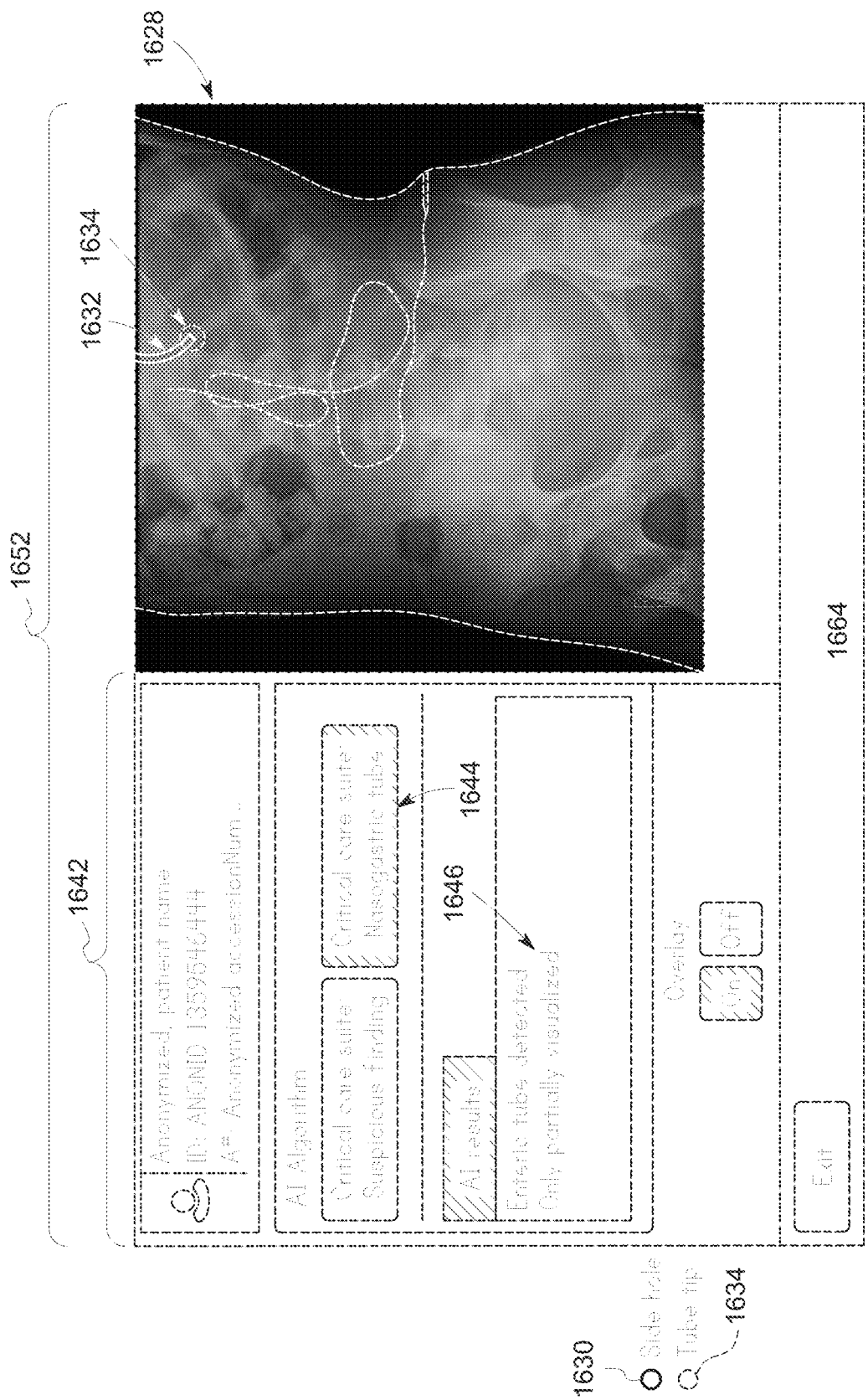
FIGS. 32-34 depict further schematic diagrams of a user interface having a combined image identifying a tube or line within a patient in a context where the tube is partially visualized.
Figure 33:
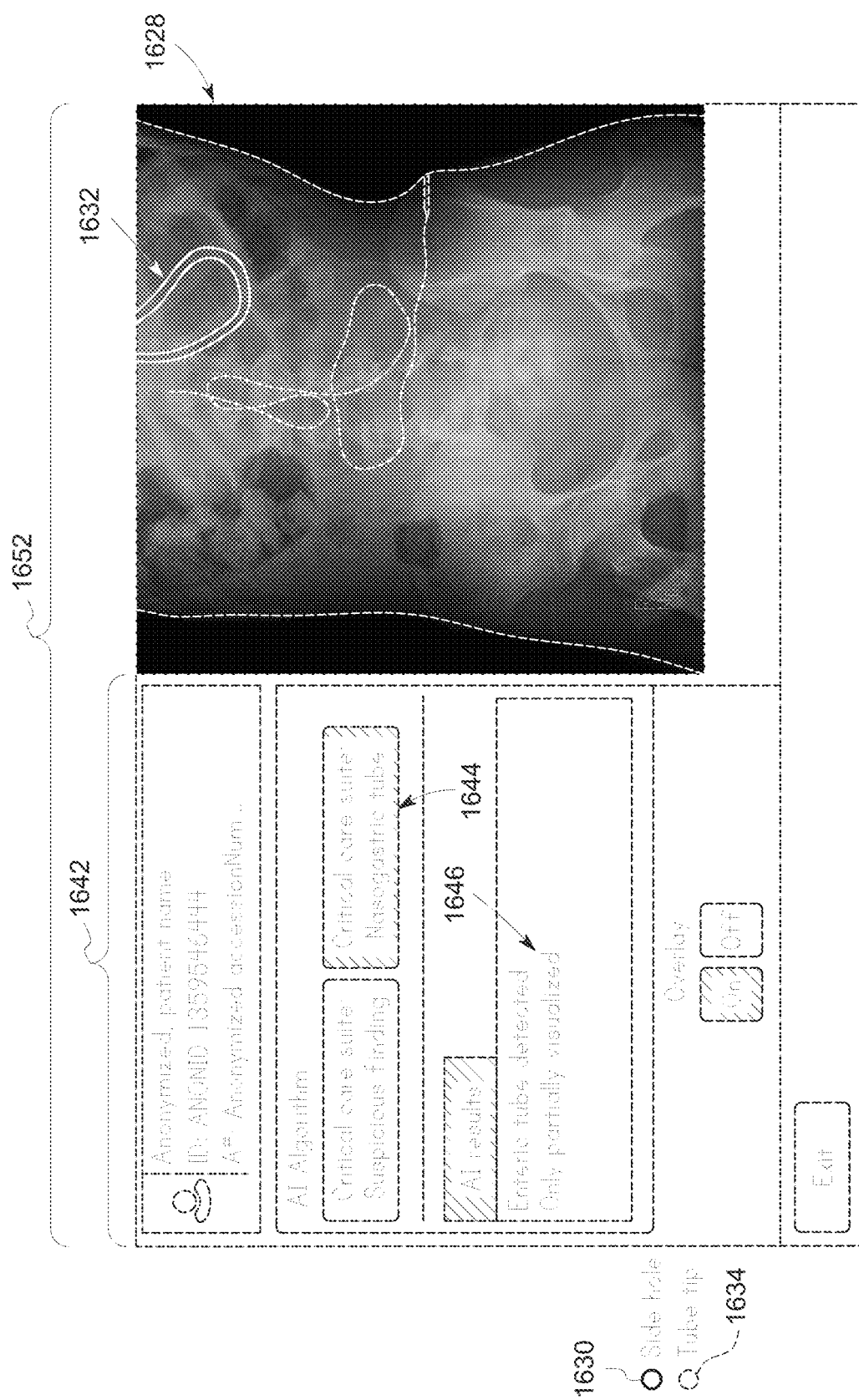
Figure 34:
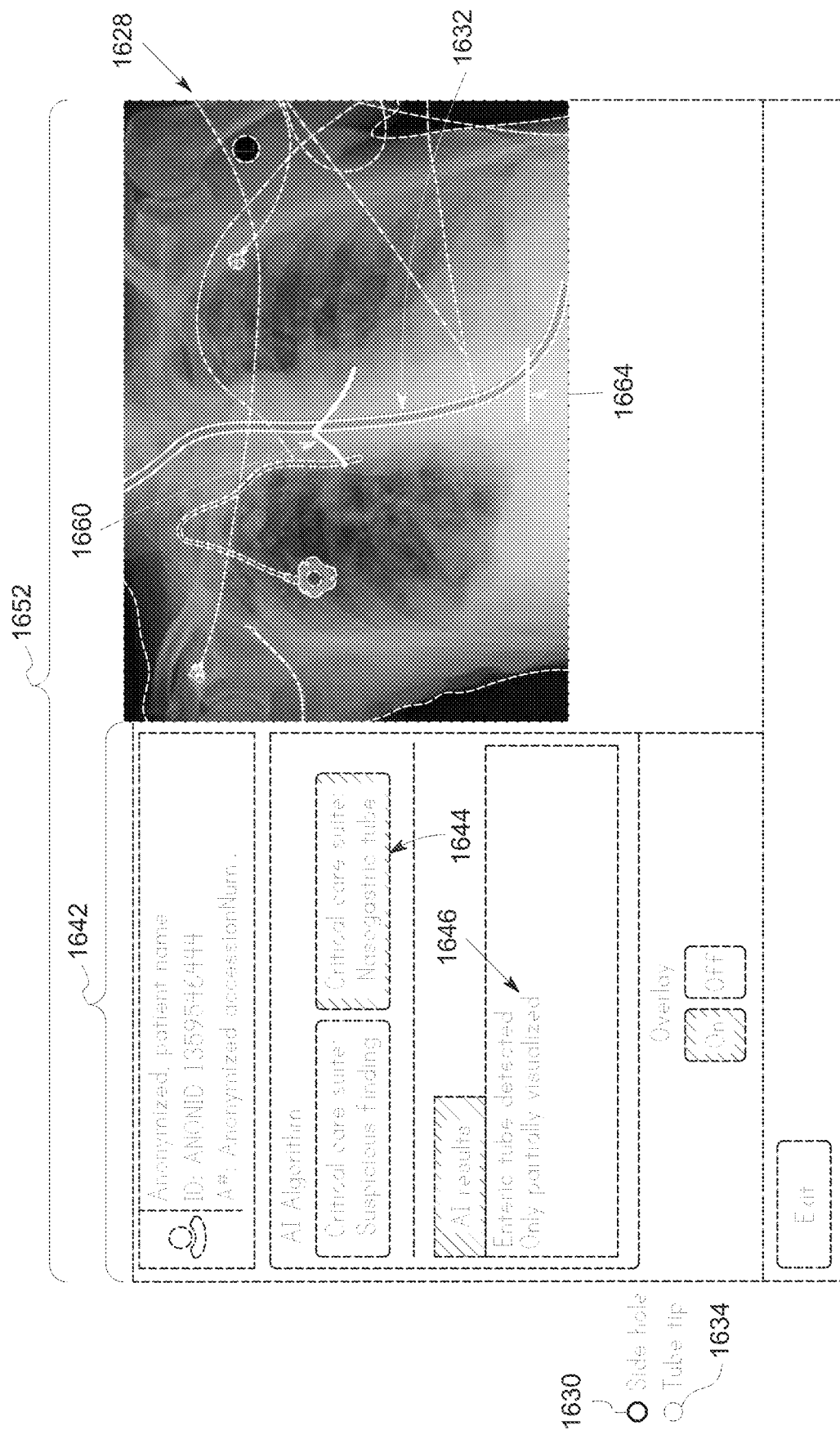

In the following examples, the tube is only partially visualized in the image data. Turning to FIG. 32, an example is displayed of results and visualization provided for one such partially visualized tube in which the tube tip is below the diaphragm but for a limited or short length. FIG. 33 depicts an example of results and visualization for a partially visualized tube where tube ascends back up from below the diaphragm to terminate out of the image. FIG. 34 depicts an example of results and visualization for a partially visualized tube where tube extends beyond the image frame.

Figure 35:
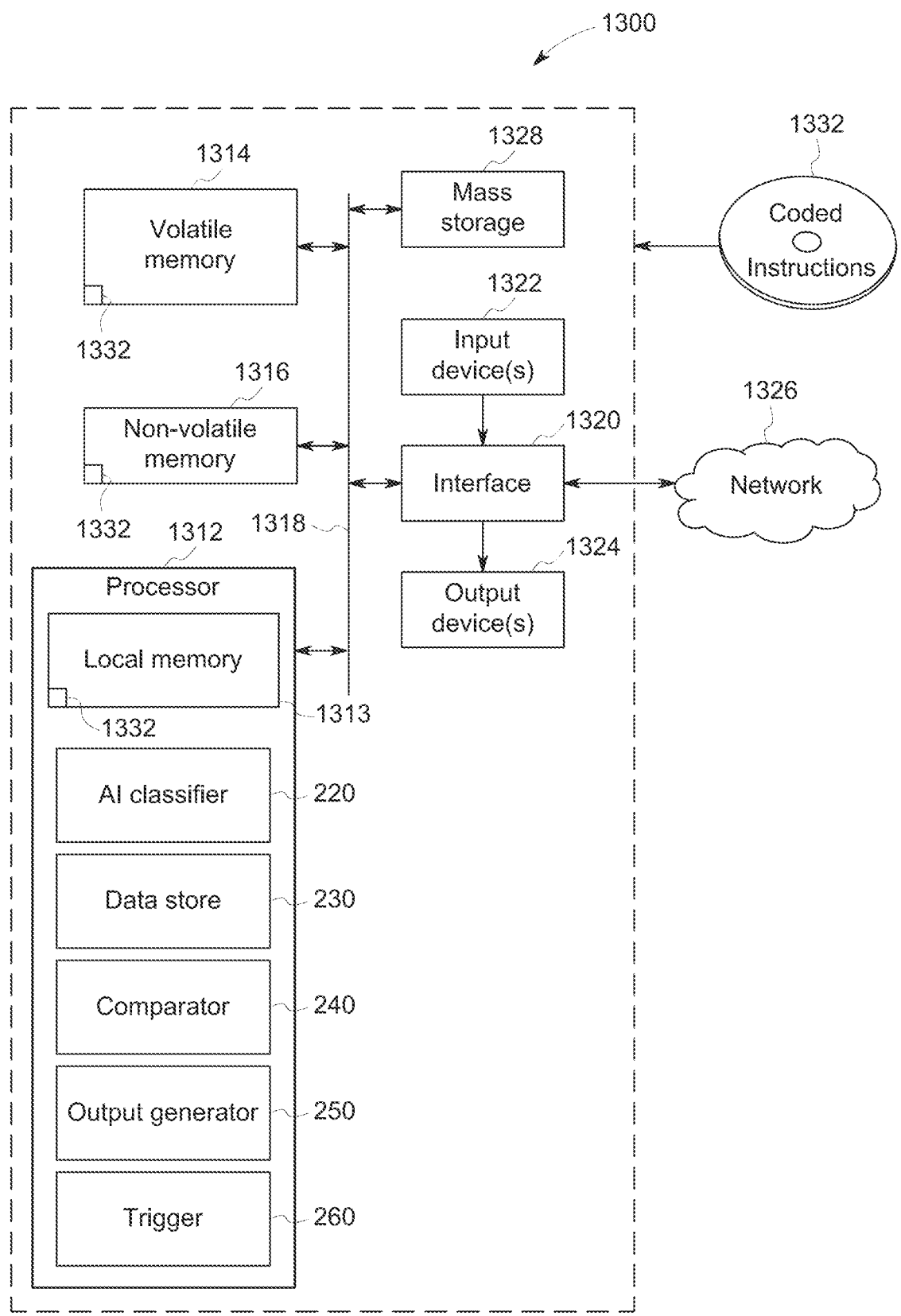
FIG. 35 is a schematic diagram of an embodiment of a processor platform structured to execute the example machine readable instructions to implement components disclosed and described herein.

FIG. 35 is a block diagram of an example processor platform 1300 structured to executing the processor-executable instructions to implement the example components disclosed and described herein. The processor platform 1300 can be, for example, a server, a personal computer, a mobile device (e.g., a cell phone, a smart phone, a tablet such as an iPad™), a personal digital assistant (PDA), an Internet appliance, or any other type of computing device.

The processor platform 1300 of the illustrated example includes a processor 1312. The processor 1312 of the illustrated example is hardware. For example, the processor 1312 can be implemented by integrated circuits, logic circuits, microprocessors or controllers from any desired family or manufacturer.

The processor 1312 of the illustrated example includes a local memory 1313 (e.g., a cache). The example processor 1312 of FIG. 35 executes processor-executable instructions to implement the systems, infrastructure, displays, and associated methods of FIGS. 1-13 such as the example data source 210, AI classifier 220, data store 230, comparator 240, output generator 250, trigger 260, etc. The processor 1312 of the illustrated example is in communication with a main memory including a volatile memory 1314 and a non-volatile memory 1316 via a bus 1318. The volatile memory 1314 may be implemented by Synchronous Dynamic Random Access Memory (SDRAM), Dynamic Random Access Memory (DRAM), RAMBUS Dynamic Random Access Memory (RDRAM) and/or any other type of random access memory device. The non-volatile memory 1316 may be implemented by flash memory and/or any other desired type of memory device. Access to the main memory 1314, 1316 is controlled by a clock controller.

The processor platform 1300 of the illustrated example also includes an interface circuit 1320. The interface circuit 1320 may be implemented by any type of interface standard, such as an Ethernet interface, a universal serial bus (USB), and/or a PCI express interface.

In the illustrated example, one or more input devices 1322 are connected to the interface circuit 1320. The input device(s) 1322 permit(s) a user to enter data and commands into the processor 1312. The input device(s) can be implemented by, for example, a sensor, a microphone, a camera (still or video, RGB or depth, etc.), a keyboard, a button, a mouse, a touchscreen, a track-pad, a trackball, isopoint and/or a voice recognition system.

One or more output devices 1324 are also connected to the interface circuit 1320 of the illustrated example. The output devices 1324 can be implemented, for example, by display devices (e.g., a light emitting diode (LED), an organic light emitting diode (OLED), a liquid crystal display, a cathode ray tube display (CRT), a touchscreen, a tactile output device, and/or speakers). The interface circuit 1320 of the illustrated example, thus, typically includes a graphics driver card, a graphics driver chip or a graphics driver processor.

The interface circuit 1320 of the illustrated example also includes a communication device such as a transmitter, a receiver, a transceiver, a modem and/or network interface card to facilitate exchange of data with external machines (e.g., computing devices of any kind) via a network 1326 (e.g., an Ethernet connection, a digital subscriber line (DSL), a telephone line, coaxial cable, a cellular telephone system, etc.).

The processor platform 1300 of the illustrated example also includes one or more mass storage devices 1328 for storing software and/or data. Examples of such mass storage devices 1328 include floppy disk drives, hard drive disks, compact disk drives, Blu-ray disk drives, RAID systems, and digital versatile disk (DVD) drives.

Coded instructions may be stored in the mass storage device 1328, in the volatile memory 1314, in the non-volatile memory 1316, and/or on a removable tangible computer readable storage medium such as a CD or DVD.

From the foregoing, it will be appreciated that the above disclosed methods, apparatus, and articles of manufacture have been disclosed to monitor, process, and improve operation of imaging and/or other healthcare systems using a plurality of deep learning and/or other machine learning techniques.

Thus, certain examples facilitate image acquisition and analysis at the point of care such as via an imaging device at the point of patient imaging. If images should be re-taken, further analysis done right away, and/or other criticality explored sooner, rather than later, the example systems, apparatus, and methods disclosed and described herein can facilitate such action to automate analysis, streamline workflow, and improve patient care.

Certain examples provide a specially-configured imaging apparatus that can acquire images and operate as a decision support tool at the point of care for a critical care team. Certain examples provide an imaging apparatus that functions as a medical device to provide and/or facilitate diagnosis at the point of care to detect radiological findings, etc.

The apparatus can trigger a critical alert for a radiologist and/or critical care team to bring immediate attention to the patient.

In certain examples, a mobile device and/or cloud product enables a vendor-neutral solution, proving point of care alerts on any digital x-ray system (e.g., fully integrated, upgrade kit, etc.). In certain examples, embedded AI algorithms executing on a mobile imaging system, such as a mobile x-ray machine, etc., provide point of care alerts during and/or in real-time following image acquisition, etc.

By hosting AI on the imaging device, a mobile x-ray system can be used in rural regions without hospital information technology networks, or even on a mobile truck that brings imaging to patient communities, for example. Additionally, if there is long latency to send an image to a server or cloud, AI on the imaging device can instead be executed and generate output back to the imaging device for further action. Rather than having the x-ray technologist moved onto the next patient and the x-ray device no longer at the patient's bedside with the clinical care team, image processing, analysis, and output can occur in real time (or substantially real time given some data transfer/retrieval, processing, and output latency) to provide a relevant notification to the clinical care team while they and the equipment are still with or near the patient. For trauma cases, for example, treatment decisions need to be made fast, and certain examples alleviate the delay found with other clinical decision support tools.

Mobile X-ray systems travel throughout the hospital to the patient bedside (e.g., emergency room, operating room, intensive care unit, etc. Within a hospital, network communication may be unreliable in "dead" zones of the hospital (e.g., basement, rooms with electrical signal interference or blockage, etc.). If the X-ray device relies on building Wi-Fi, for example, to push the image to a server or cloud which is hosting the AI model and then wait to receive the AI output back to the X-ray device, then patient is at risk of not having reliability in critical alerts when needed. Further, if a network or power outage impacts communications, the AI operating on the imaging device can continue to function as a self-contained, mobile processing unit.

Examples of alerts generated for general radiology can include critical alerts (e.g., for mobile x-ray, etc.) such as tubes and line placement, pleural effusion, lobar collapse, pneumoperitoneum, pneumonia, etc.; screening alerts (e.g., for fixed x-ray, etc.) such as tuberculosis, lung nodules, etc.; quality alerts (e.g., for mobile and/or fixed x-ray, etc.) such as patient positioning, clipped anatomy, inadequate technique, image artifacts, etc.

Thus, certain examples improve accuracy of an artificial intelligence algorithm. Certain examples factor in patient medical information as well as image data to more accurately predict presence of a critical finding, an urgent finding, and/or other issue.

Although certain example methods, apparatus and articles of manufacture have been described herein, the scope of coverage of this patent is not limited thereto. On the contrary, this patent covers all methods, apparatus and articles of manufacture fairly falling within the scope of the claims of this patent.

Technical effects of the disclosed subject matter include providing systems and methods that utilize AI (e.g., deep learning networks) to determine whether or not a medically placed tube or line is properly placed within a region of interest (e.g., relative to a reference or anatomical landmark). The systems and methods may provide feedback in real time that in a more accurate and quicker manner determine if a medically placed tube or line is misplaced. Thus, enabling fast intervention, if needed, to move the tube or line to the appropriate location for patient safety.

This written description uses examples to disclose the subject matter, including the best mode, and also to enable any person skilled in the art to practice the subject matter, including making and using any devices or systems and performing any incorporated methods. The patentable scope of the disclosed subject matter is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A medical image processing system, comprising:
    a display;
    a processor; and
    a memory storing processor-executable code that when executed by the processor causes:
        receiving structural anatomic image data associated with an enteric tube or line disposed within a region of interest comprising all or part of a chest or abdominal region of a patient;
        detecting the enteric tube or line within the structural anatomic image data;
        detecting one or more anatomic reference landmarks within the structural anatomic image data, wherein the one or more anatomical reference landmarks are within the region of interest;
        generating a combined image by superimposing one or more graphical markers on an image derived based on the structural anatomic image data, wherein the one or more graphical markers indicate one or more features of the enteric tube or line in an anatomic context determined based on the one or more anatomic reference landmarks; and
        displaying the combined image on the display.

2. The medical image processing system of claim 1, wherein generating the combined image comprises superimposing one or more anatomic graphical markers on the image that indicates the one or more anatomic reference landmarks.

3. The medical image processing system of claim 2, wherein the processor-executable code when executed by the processor causes calculating a measured position of a distal tip of the enteric tube or line relative to a respective anatomic reference landmark, and wherein generating the combined image comprises superimposing a graphical indicator on the image that indicates the measured position.

4. The medical image processing system of claim 1, wherein the processor-executable code when executed by the processor causes determining whether the enteric tube or line is wholly or partially visible within the combined image.

5. The medical image processing system of claim 1, wherein the processor-executable code when executed by the processor causes determining whether the enteric tube or line is properly placed relative to a respective anatomic reference landmark.

6. The medical image processing system of claim 5, wherein the processor-executable code when executed by the processor causes displaying an indication with the combined image when the enteric tube or line is misplaced relative to the respective anatomic reference landmark.

7. The medical image processing system of claim 1, wherein the enteric tube or line comprises a nasogastric tube, a nasoduodenal tube, a nasojejunal tube, an orogastric tube, an oroduodenal tube, or an orojejunal tube.

8. The medical image processing system of claim 1, wherein the one or more anatomic reference landmarks comprises a carina, a diaphragm, an airway, a stomach, lungs, a midline, or an edge of an airway.

9. The medical image processing system of claim 1, wherein detecting the enteric tube or line within the structural anatomic image data comprises utilizing one or more deep learning network models to detect the enteric tube or line within the structural anatomic image data.

10. The medical image processing system of claim 1, wherein generating the combined image comprises superimposing on the image a colored graphical overlay over the enteric tube or line to facilitate visualization of the enteric tube or line.

11. The medical image processing system of claim 1, wherein the one or more graphical markers are color-coded to indicate one or both of proper or improper placement of the enteric tube or line.

12. A method for medical image processing, comprising:
    receiving, via a processor, structural anatomic image data associated with an enteric tube or line disposed within a region of interest comprising all or part of a chest or abdominal region of a patient;
    detecting, via the processor, the enteric tube or line within the structural anatomic image data;
    detecting one or more anatomic reference landmarks within the structural anatomic image data, wherein the one or more anatomical reference landmarks are within the region of interest;
    generating, via the processor, a combined image by superimposing one or more graphical markers on an image derived based on the structural anatomic image data, wherein the one or more graphical markers indicate one or more features of the enteric tube or line in an anatomic context determined based on the one or more anatomic reference landmarks; and
    causing, via the processor, display of the combined image on a display.

13. The method of claim 12, comprising identifying, via the processor, a portion of the one or more anatomic reference landmarks within the region of interest as associated with a type of the enteric tube or line.

14. The method of claim 13, wherein generating the combined image comprises superimposing, via the processor, one or more anatomic graphical markers on the image that indicates the portion of the one or more anatomic reference landmarks.

15. The method of claim 14, comprises calculating, via the processor, a measured position of a distal tip of the enteric tube or line relative to a respective anatomic reference landmark, and wherein generating the combined image comprises superimposing a graphical indicator on the image that indicates the measured position.

16. The method of claim 13, comprises determining, via the processor, whether the enteric tube or line is wholly or partially visible within the combined image.

17. The method of claim 13, comprising determining, via the processor, whether the enteric tube or line is properly placed relative to a respective anatomic reference landmark.

18. The method of claim 17, comprising displaying, via the processor, an indication with the combined image when the enteric tube or line is misplaced relative to the respective anatomic reference landmark.

19. The method of claim 12, wherein detecting the enteric tube or line within the structural anatomic image data comprises utilizing, via the processor, one or more deep learning network models to detect the enteric tube or line within the structural anatomic image data.

20. A non-transitory, computer-readable medium, the computer-readable medium comprising processor-executable code configured to:
- receive structural anatomic image data associated with an enteric tube or line disposed within a region of interest comprising all or part of a chest or abdominal region of a patient;
- detect the enteric tube or line within the structural anatomic image data;
- detect one or more anatomic reference landmarks within the structural anatomic image data, wherein the one or more anatomical reference landmarks are within the region of interest;
- generate a combined image by superimposing one or more graphical markers on an image derived based on the structural anatomic image data, wherein the one or more graphical markers indicate one or more features of the enteric tube or line in an anatomic context determined based on the one or more anatomic reference landmarks; and
- display the combined image on a display.

* * * * *